(12) United States Patent
Nishizawa et al.

(10) Patent No.: US 10,391,041 B2
(45) Date of Patent: Aug. 27, 2019

(54) SHEET-SHAPED HAIR COSMETIC AND HAIR TREATMENT METHOD AND SCALP-WIPING METHOD USING SAME

(71) Applicant: Kao Corporation, Tokyo (JP)

(72) Inventors: Eiichi Nishizawa, Yokohama (JP); Azusa Kasuga, Taito-ku (JP); Keiko Ishii, Kawaguchi (JP); Rina Iikubo, Sumida-ku (JP); Kaori Kojima, Katsushika-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/781,705

(22) PCT Filed: Apr. 1, 2014

(86) PCT No.: PCT/JP2014/059631
§ 371 (c)(1),
(2) Date: Oct. 1, 2015

(87) PCT Pub. No.: WO2014/163075
PCT Pub. Date: Oct. 9, 2014

(65) Prior Publication Data
US 2016/0051452 A1    Feb. 25, 2016

(30) Foreign Application Priority Data

Apr. 1, 2013   (JP) ................... 2013-076482

(51) Int. Cl.
| | | |
|---|---|---|
| *A61K 8/02* | (2006.01) | |
| *A45D 19/16* | (2006.01) | |
| *A61Q 5/12* | (2006.01) | |
| *A61Q 5/02* | (2006.01) | |
| *A61K 8/34* | (2006.01) | |
| *A61K 8/39* | (2006.01) | |
| *A61K 8/41* | (2006.01) | |
| *A61K 8/73* | (2006.01) | |
| *A61K 8/81* | (2006.01) | |
| *A61K 8/86* | (2006.01) | |
| *A61K 8/898* | (2006.01) | |
| *A61K 8/85* | (2006.01) | |
| *A45D 19/00* | (2006.01) | |

(52) U.S. Cl.
CPC ............ *A61K 8/0208* (2013.01); *A45D 19/16* (2013.01); *A61K 8/34* (2013.01); *A61K 8/39* (2013.01); *A61K 8/41* (2013.01); *A61K 8/73* (2013.01); *A61K 8/731* (2013.01); *A61K 8/81* (2013.01); *A61K 8/85* (2013.01); *A61K 8/86* (2013.01); *A61K 8/898* (2013.01); *A61Q 5/02* (2013.01); *A61Q 5/12* (2013.01); *A45D 2019/005* (2013.01); *A61K 2800/56* (2013.01); *A61K 2800/592* (2013.01); *A61K 2800/87* (2013.01)

(58) Field of Classification Search
CPC ............ A61Q 5/02; A61Q 5/12; A45D 19/00; A45D 2019/0041–005; A61K 2800/87
See application file for complete search history.

(56) References Cited

U.S. PATENT DOCUMENTS

| | | | |
|---|---|---|---|
| 3,954,113 A * | 5/1976 | Bohrer ................ | A47K 7/03 132/200 |
| 5,686,066 A | 11/1997 | Harada et al. | |
| 6,153,208 A | 11/2000 | McAtee et al. | |
| 7,073,684 B2 * | 7/2006 | Decker ............... | A47K 10/421 221/63 |
| 7,172,801 B2 | 2/2007 | Hoying et al. | |
| 7,270,861 B2 | 9/2007 | Broering et al. | |
| 7,410,683 B2 | 8/2008 | Curro et al. | |
| 7,507,459 B2 | 3/2009 | Turner et al. | |
| 7,648,752 B2 | 1/2010 | Hoying | |
| 7,670,665 B2 | 3/2010 | Hoying et al. | |
| 7,682,686 B2 | 3/2010 | Curro et al. | |
| 7,718,243 B2 | 5/2010 | Curro et al. | |
| 7,732,657 B2 | 6/2010 | Hammons et al. | |
| 7,785,690 B2 | 8/2010 | Turner et al. | |
| 7,829,173 B2 | 11/2010 | Turner et al. | |
| 7,838,099 B2 | 11/2010 | Curro et al. | |
| 7,910,195 B2 | 3/2011 | Hammons et al. | |
| 7,938,635 B2 | 5/2011 | Heilman et al. | |

(Continued)

FOREIGN PATENT DOCUMENTS

| | | |
|---|---|---|
| CN | 1720362 A | 1/2006 |
| EP | 1 065 302 A1 | 1/2001 |

(Continued)

OTHER PUBLICATIONS

Extended European Search Report dated Sep. 1, 2016 in Patent Application No. 14778221.3.

(Continued)

*Primary Examiner* — H. Sarah Park
(74) *Attorney, Agent, or Firm* — Oblon, McClelland, Maier & Neustadt, L.L.P.

(57) ABSTRACT

A sheet-like hair care product including (A) a substrate sheet containing cellulosic fibers and having a bending resistance of 10 to 70 mm measured by the 45° cantilever method in accordance with JIS L1096:2010 and (B) a liquid cosmetic composition. The substrate sheet (A) is impregnated with 1 to 50 g of the liquid cosmetic composition (B). The substrate sheet impregnated with the liquid cosmetic composition is preferably packaged in a packaging container having an access opening with an area of 25 to 4000 mm² and an openable and closable lid sealing the contents.

25 Claims, 8 Drawing Sheets

(56) References Cited

U.S. PATENT DOCUMENTS

| | | | |
|---|---|---|---|
| 8,075,977 B2 | 12/2011 | Curro et al. | |
| 8,153,225 B2 | 4/2012 | Turner et al. | |
| 8,357,445 B2 | 1/2013 | Hammons et al. | |
| 8,697,218 B2 | 4/2014 | Turner et al. | |
| 8,795,716 B2 | 8/2014 | Warren et al. | |
| 8,877,316 B2 | 11/2014 | Hasenoehrl et al. | |
| 8,907,154 B2 | 12/2014 | Gatto et al. | |
| 9,498,794 B2 | 11/2016 | Heilman et al. | |
| 2002/0192268 A1* | 12/2002 | Alwattari | A45D 37/00 424/443 |
| 2003/0082219 A1 | 5/2003 | Warren et al. | |
| 2003/0113364 A1 | 6/2003 | McAtee et al. | |
| 2003/0206943 A1 | 11/2003 | Hammons et al. | |
| 2003/0228351 A1 | 12/2003 | Hasenoehrl et al. | |
| 2004/0000382 A1 | 1/2004 | Omura et al. | |
| 2004/0131820 A1 | 7/2004 | Turner et al. | |
| 2004/0170589 A1 | 9/2004 | Gatto | |
| 2004/0242097 A1* | 12/2004 | Hasenoehrl | A44B 18/0011 442/59 |
| 2005/0129651 A1 | 6/2005 | Gatto et al. | |
| 2005/0154362 A1 | 7/2005 | Warren et al. | |
| 2006/0062816 A1 | 3/2006 | Gatto et al. | |
| 2007/0219107 A1 | 9/2007 | Nonomura et al. | |
| 2007/0286876 A1 | 12/2007 | Warren et al. | |
| 2008/0075748 A1 | 3/2008 | Hasenoehrl et al. | |
| 2010/0003449 A1 | 1/2010 | Turner et al. | |
| 2011/0206904 A1 | 8/2011 | Heilman et al. | |
| 2014/0170367 A1 | 6/2014 | Turner et al. | |
| 2015/0073367 A1 | 3/2015 | Gatto et al. | |
| 2017/0037209 A1 | 2/2017 | Heilman et al. | |

FOREIGN PATENT DOCUMENTS

| | | |
|---|---|---|
| JP | 3-153617 A | 7/1991 |
| JP | 10-25344 A | 1/1998 |
| JP | 10-237750 A | 9/1998 |
| JP | 3065358 U | 2/2000 |
| JP | 2001 55319 | 2/2001 |
| JP | 2001 516712 | 10/2001 |
| JP | 2002 249965 | 9/2002 |
| JP | 2002 255737 | 9/2002 |
| JP | 2003-93152 A | 4/2003 |
| JP | 2003 164501 | 6/2003 |
| JP | 2004 168698 | 6/2004 |
| JP | 2005-350380 A | 12/2005 |
| JP | 2006-149444 A | 6/2006 |
| JP | 2006-181334 A | 7/2006 |
| JP | 2006-241654 A | 9/2006 |
| JP | 2006 520324 | 9/2006 |
| JP | 2006-525440 A | 11/2006 |
| JP | 2008-208491 A | 9/2008 |
| JP | 2008 208492 | 9/2008 |
| JP | 2009-197374 A | 9/2009 |
| JP | 2009-286750 A | 12/2009 |
| JP | 2010-84297 A | 4/2010 |
| JP | 2010 84317 | 4/2010 |
| JP | 2010-100543 A | 5/2010 |
| JP | 2011-37772 A | 2/2011 |
| JP | 2011 137246 | 7/2011 |
| JP | 2012-149036 A | 8/2012 |
| JP | 2013-173744 A | 9/2013 |
| JP | 2014 108306 | 6/2014 |
| JP | 2014 108307 | 6/2014 |
| KR | 10 2009 0038154 | 4/2009 |
| WO | WO 2006/013671 A1 | 2/2006 |
| WO | 2012/029753 A1 | 3/2012 |
| WO | 2012 090412 | 7/2012 |

OTHER PUBLICATIONS

International Preliminary Report on Patentability and Written Opinion dated Oct. 15, 2015 in PCT/JP2014/059631 (submitting English translation only).

"Hair Sheet Treatment", MINTEL GNPD, (May 2006), Total 6 Pages, (with English translation).

"Japanese Cosmetic Labeling Name Dictionary, the Third Edition", (Apr. 15, 2013), Total 5 Pages, (with English translation).

International Search Report dated Jun. 17, 2014 in PCT/JP14/059631 Filed Apr. 1, 2014.

Zhu Xue et al.-"Application of Surfactants in Cosmetics" China Cosmetics Review (with computer generated English translation).

* cited by examiner

SHEET-SHAPED HAIR COSMETIC AND HAIR TREATMENT METHOD AND SCALP-WIPING METHOD USING SAME

CROSS REFERENCE TO RELATED APPLICATION

This application is a 371 of PCT/JP2014/059631, filed on Apr. 1, 2014, and claims priority to Japanese Patent Application 2013-076482, filed on Apr. 1, 2013.

TECHNICAL FIELD

The present invention relates to a hair care product of sheet form and hair treatment and scalp cleaning methods using the same.

BACKGROUND ART

There are demands for removal of sebum, sweat, smell, dirt or like from hair and scalp and for hair fixing or styling in absence of sufficient water, for example, while on the go, in hospital, in a nursing home, during outdoor activities such as climbing and camping, or with water outage due to a disaster.

Fixing hair into a natural style is usually done by applying water or a hair styling products to hair, followed by drying spontaneously or using a heater such as a hair dryer. In the above described situations, however, use of water as well as a hair styling products is limited, and the desires to be clean or to keep a beautiful hairstyle are very difficult to satisfy.

The main function of a shampoo is to remove dirt from hair, and the dirt is generally washed off together with a used shampoo. On the other hand, a dry shampoo of sheet form is known, which is used to remove dirt form the hair and scalp in a situation where one cannot use water. For example, Patent Literature 1 discloses a dry shampoo sheet formed of a nonwoven fabric substrate of 500 to 900 cm² in area and 0.1 to 3 mm in thickness impregnated with a composition containing water, ethanol, and f-menthol. Patent Literature 2 discloses a dry shampoo sheet that is a liquid preparation-impregnated nonwoven fabric sheet comprising rayon and a thermobondable resin, and having an area of 450 to 550 cm². The impregnating liquid preparation contains ethanol, a moisturizer, a surfactant, and water. The dry shampoo sheet of Patent Literature 2 is intended to be used in combination with a specific tool having a number of protrusions on its surface.

Skin care products of sheet form for cleaning the skin are well known. For example, Patent Literature 3 discloses a skin cleaning sheet which is a substrate sheet having a thickness of 0.1 to 0.3 mm and a cantilever bending stiffness of 1.0 to 10.0 mN·cm in both the machine and cross-machine directions, the substrate sheet being impregnated with an aqueous medium. The skin cleaning sheet is intended for use to remove sebum and dirt from the skin. The substrate sheet used is thin and stiff in an attempt to prevent bending of the substrate sheet during use thereby to provide improved convenience of use.

CITATION LIST

Patent Literature

Patent Literature 1: JP 2001-55319A
Patent Literature 2: JP 2004-168698A
Patent Literature 3: JP 2002-255737A

SUMMARY OF INVENTION

Technical Problem

Proposed with the main aim of removing dirt from hair and/or scalp, the dry shampoo sheets of Patent Literatures 1 and 2 are insufficient in providing good hair care in outdoor usage. That is, when one wants to tame one's unruly hair, such as sticking-out hairs or flyaway hairs, or to give a treatment effect to one's hair in the absence of ample water, it is necessary to apply a sufficient amount of a liquid preparation to not only the scalp but also whole hair. The conventional dry shampoo sheets are not necessarily satisfactory in applying a sufficient amount of a liquid preparation to the whole hair while retaining the advantage of portability.

Every hair strands has an outer side and an inner side with respect to the body surface. Both the dry shampoo sheets of Patent Literatures 1 and 2 sometimes fail to sufficiently furnish the liquid preparation to the inner side of hair strands when applied from the roots to the tips of hair. In situations in which hair care tools, such as a brush, are not available, users cannot help but applying the dry shampoo sheet using their hands. In such cases, users often feel inconvenience in trying the liquid preparation to the whole hair uniformly.

When the sheet is applied to hair as attached to a tool, such as a brush, it is easy to remove dirt adhering to the outer side of exposed hair strands but difficult to remove dirt from the inner side of hair strands or unexposed strands of hair. Still more difficult is it to evenly apply a sufficient amount of liquid preparation to the whole hair.

In wiping clean a scalp thick with hair (unlike the face and body), the hair is an obstruction of wiping operation. Therefore, a skin cleaning sheet such as described in Patent Literature 3 is insufficient in cleaning scalp. Because the hair, unlike the face or body, is composed of dry proteins with a low water content and has an extremely large surface area, a skin cleaning sheet as described in Patent Literature 3 fails to provide a sufficient wiping effect and a treatment effect on account of lack of conformability to the shape of a hand and fingers and an insufficient content of a liquid preparation.

The invention provides a sheet-like hair care product free from the above described disadvantages of conventional techniques.

Solution to Problem

The inventors have conducted extensive studies seeking for solutions to the above described problems. As a result, they have found it important for a sheet-like hair care product to be easy to unfold and spread out when taken out of a container, to have good conformability to a user's hand and fingers, to be capable of being impregnated with and retaining an appropriate amount of a liquid cosmetic composition, and to have sufficient sheet strength withstanding physical forces, such as friction, so as to perform hair treatment and cleaning, and thus reached the invention.

The present invention has been completed based on the above findings. The invention provides a sheet-like hair care product including (A) a substrate sheet containing cellulosic fibers and having a bending resistance of 10 to 70 mm as measured by the 45° cantilever method in accordance with JIS L1096:2010 and (B) a liquid cosmetic composition, component (A) being impregnated with 1 g to 50 g of component (B) per sheet.

The invention also provides a sheet-like hair care product, in which the substrate sheet contains cellulosic fibers and thermoplastic resin fibers, and the sheet-like hair care product is packaged in a specific container. Specifically, the invention provides a hair care product including (A) a substrate sheet containing cellulosic fibers and having a bending resistance of 10 mm to 70 mm measured by the 45° cantilever method in accordance with JIS L1096:2010, (B) a liquid cosmetic composition containing (B-1) a mono- or polyhydric alcohol having 1 to 6 carbon atoms, (B-2) a surfactant, and (B-3) water, and (C) a packaging container including: an access opening which has an area of 25 $mm^2$ to 4000 $mm^2$ and through which the contents are dispensed; and an openable and closable lid to cover the access opening and to seal the contents. (A) is impregnated with 6 g to 25 g of (B) per sheet, and the impregnated (A) is held in (C).

The invention also provides a hair treating method using the sheet-like hair care product of the invention. The method includes the steps of (i) optionally picking up the sheet-like hair care product, which is impregnated with the liquid cosmetic composition, from the packaging container through the access opening, (ii) spreading out the sheet-like hair care product on the palmer side of a user's hand in such a manner that a part of the sheet-like hair care product hangs over the fingertips, and (iii) moving the user's hand with the sheet-like hair care product thereon from the roots to the tips of hair strands to treat the hair strands.

The invention also provides a scalp cleaning method using the sheet-like hair care product of the invention. The method includes the steps of (i) optionally (i.e., when the sheet-like hair care product is held in the packaging container) picking up the sheet-like hair care product impregnated with the liquid cosmetic composition from the packaging container through the access opening, (ii) (ii) spreading out the sheet-like hair care product on the palmer side of a user's hand in such a manner that a part of the sheet-like hair care product hangs over the fingertips, and (iii) applying the fingertips with the sheet-like hair care product thereon to the scalp and rubbing the fingers against the scalp in a to-and-fro vertical or horizontal motion.

The invention also provides a method for cleaning a scalp using the sheet-like hair care product of the invention. The method includes the steps of optionally picking up the sheet-like hair care product impregnated with the liquid cosmetic composition from the packaging container through the access opening when the sheet-like hair care product is held in the packaging container, (i) folding the sheet-like hair care product impregnated with the liquid cosmetic composition, (ii) inserting user's fingers into the fold to hold the sheet-like hair care product in the user's hand, and (iii) applying the hand holding the sheet-like hair care product to the scalp and rubbing the fingertips against the scalp via the sheet-like hair care product.

Advantageous Effects of Invention

The invention provides a portable hair care product capable of sufficiently removing dirt from both hair and a scalp and applying the ingredients of the impregnating liquid cosmetic composition to hair thinly and uniformly without using any tool and therefore allowing for hair fixing while controlling unruly hair strands.

DESCRIPTION OF EMBODIMENTS

The invention will be described based on its preferred embodiments. The sheet-like hair care product of the invention is composed of a substrate sheet impregnated with a liquid cosmetic composition. The details of the substrate sheet will be described later. The liquid cosmetic composition impregnating the substrate sheet has a composition selected as appropriate to the intended use of the sheet-like hair care product as will be described.

A first embodiment of the sheet-like hair care product of the invention will be described first. According to the first embodiment, the liquid cosmetic composition (B) contains (B-1) a mono- or polyhydric alcohol having 1 to 6 carbon atoms, (B-2) a surfactant, and (B-3) water. The sheet-like hair care product composed of a specific substrate sheet hereinafter described impregnated with the liquid cosmetic composition having ingredients (B-1) to (B-3) is capable of sufficiently removing dirt from both hair and a scalp without using any tool or device. It is also capable of applying the ingredients of the impregnating liquid cosmetic composition to hair thinly and uniformly to fix hair while controlling unruly hair strands. The sheet-like hair care product has excellent portability.

Figure 1:
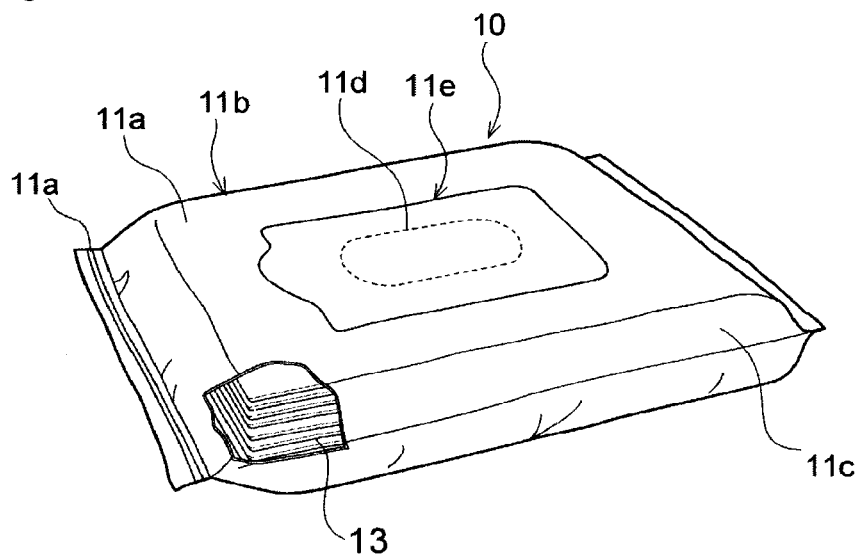
FIG. 1 is a perspective of an embodiment of the hair care product of the invention with part cut away.

FIG. 1 is a perspective of an embodiment of the hair care product of the invention with part cut away. The hair care product of this embodiment has an embodiment of the sheet-like hair care product of the invention held in a packaging container. The hair care product 10 shown in FIG. 1 has a packaging container 11. The packaging container 11 is formed by shaping a single sheet material. In detail, the container 11 is made by lap-bonding opposed sides of a sheet material (not shown) to make a cylinder and sealing each of the two ends of the cylinder by, for example, heat seals 11a. In the following description, the hair care product 10 having the sheet-like hair care product of the present embodiment held in the packaging container will also be simply referred to as "the hair care product 10 of the present embodiment".

The sheet material used to make the packaging container 11 is a water impermeable material chosen from a commonly used range of materials. It is preferred for the sheet material to be not only water impermeable but also impermeable to water vapor and ethanol vaporized from the sheet-like hair care product. Use of such a sheet material effectively prevents the liquid cosmetic composition from oozing or vaporizing from the wet sheet-like hair care product 13 in the container 11. Examples of a sheet material having the above discussed properties include aluminum-deposited thermoplastic resin film and a thermoplastic resin film laminate having an aluminum interlayer.

The packaging container 11 has an upper surface 11b, a lower surface (not shown) located opposite to the upper surface 11b. The packaging container 11 also has a first side surface 11c, and a second side surface (not shown) located opposite to the first side surface 11c. The packaging container 11 has an access opening 11d through which the contents are to be taken out which is located in substantially the center of the upper surface 11b. The shape of the access opening 11d may be, but is not limited to, a shape elongated in the longitudinal direction of the upper surface 11b. The wet substrate sheets 12 held in the container 11 are each dispensed through the access opening 11d. The shape of the access opening 11d is not particularly limited, but the access opening 11d is preferably oblong rectangular, oblong elliptic, square, generally square, circular, or generally circular, taking into consideration ease of spreading out the sheet-like hair care product 13 taken out through the access opening 11d.

Because the wet sheet-like hair care product 13 taken out of the container 11 contains a large amount of the liquid cosmetic composition as will be described infra, it tends to stick to itself and be difficult to spread out. In order to make it easier to spread out the sheet-like hair care product 13, it is preferred that the access opening 11d not be too large. Specifically, the area of the access opening 11d is advantageously 4000 $mm^2$ or less, preferably 3000 $mm^2$ or less, more preferably 2500 $mm^2$ or less. On the other hand, in order to take out the sheet-like hair care product 13 from the container 11 while retaining a sufficient amount of the impregnating liquid cosmetic composition, it is preferred for the access opening 11d not to be too small. Specifically, the area of the access opening 11d is advantageously 25 $mm^2$ or more, preferably 100 $mm^2$ or more, more preferably 200 $mm^2$ or more. For example, the area of the access opening 11d is preferably 25 $mm^2$ to 4000 $mm^2$, more preferably 100 $mm^2$ to 3000 $mm^2$, even more preferably 200 $mm^2$ to 2500 $mm^2$.

In the case where the sheet-like hair care product 13 is held in the packaging container 11 in a folded state, the folded product 13 is preferably placed in the container 11 such that the folded edge may be seen from the access opening 11d so that the wet sheet-like hair care product 13 taken out of the container 11 may be spread out easily. From the same standpoint, the sheet-like hair care product 13 is preferably put in the container 11 in a fashion that the edge of the sheet-like hair care product 13 may be seen from the access opening 11d whether or not the sheet-like hair care product 13 is folded.

An openable and closable lid 11e is placed on the upper surface 11b of the packaging container 11 so as to entirely cover the access opening 11d. Any type of lid may be used as long as the ingredients vaporized from the sheet-like hair care product, such as water vapor and ethanol, are sealed in. Examples of the lid include a hinged flip, a peel-and-reseal label, and a valve. The lid 11e used in the present embodiment is a peel-and-reseal label flap having a releasable adhesive (unshown) applied to its surface contacting the upper surface 11b of the container 11. The releasable adhesive allows the lid 11e to peel off and re-adhere to the upper surface 11b of the container 11 to cover the access opening 11d. Releasable and resealable adhesives conventionally used in the art, such as polyester, acrylic, or rubber pressure sensitive adhesives, may be used. The lid 11e covers the entire area of the access opening 11d during storage of the hair care product 10 of the present embodiment, and peeled partly or entirely from the upper surface of the access opening 11d to expose the access opening 11 when using. The wet sheet-like hair care product 13 is then picked up and taken out by hand from the container 11 through the access opening 11d.

The packaging container 11 holds a plurality of wet sheet-like hair care products 13 impregnated with the liquid cosmetic composition as individually folded into a predetermined shape or unfolded. From the viewpoint of portability of the hair care product 10, each sheet-like hair care product 13 is preferably held in the container as folded. In what follows, the term "substrate sheet" or simply "sheet" is intended to include both a wet sheet impregnated with the liquid cosmetic composition and a dry sheet that is not impregnated with the liquid cosmetic composition depending on the context. Having the sheet-like hair care products 13 impregnated with the liquid cosmetic composition held in the packaging container 11, the hair care product 10 of the present embodiment has markedly improved portability to provide high user-friendliness in a variety of situations such as being on the go.

The plan view area of the individual sheet-like hair care products 13 held in the packaging container 11 is preferably 10 $cm^2$ or more and 400 $cm^2$ or less, more preferably 300 $cm^2$ or less, even more preferably 200 $cm^2$ or less, in relation to the opening area of the access opening of the container 11, regardless of whether the sheet-like hair care product 13 is folded. For example, the plan view area of the sheet-like hair care product 13 held in the container 11 is preferably 10 $cm^2$ to 400 $cm^2$, more preferably 10 $cm^2$ to 300 $cm^2$, even more preferably 10 $cm^2$ to 200 $cm^2$.

The substrate sheet 12 may be a single layered sheet or a multi-layered sheet having two or more layers. It may also be a multi-ply sheet having two or more plies of nonwoven fabric. It may be laminated on one side thereof with a film impermeable to the liquid cosmetic composition (what we call a backsheet). The substrate sheet 12 is usually rectangular but may be otherwise shaped to be helpful in smoothly cleaning hair and a scalp.

The substrate sheet 12 preferably has high pliability and drape (the degree to which a material having fabric-like texture deforms when allowed to hang under its own weight). To be pliable for the sheet-like hair care product 13 is to be ready to comfort to the shape of the palm and fingers after being taken out of the container 11 and put on the palmer side of a user's hand and ready to impart the impregnating liquid cosmetic composition to hair thinly and uniformly. On the other hand, the sheet-like hair care product 13 is required to have moderate stiffness so as to be easy to spread out. In this regard, when the pliability of the substrate sheet before impregnation with the liquid cosmetic composition is represented in terms of bending resistance measured in accordance with JIS L1096:2010 (45-degree cantilever method), the sheet-like hair care product 13 need to have a bending resistance of 10 mm or more and preferably has a bending resistance of 30 mm or more. The bending resistance is 70 mm or less, advantageously 65 mm or less, more advantageously 60 mm or less, even more advantageously 50 mm or less. Specifically, the bending resistance is preferably 10 mm to 70 mm, more preferably 10 mm to 65 mm, even more preferably 10 mm to 60 mm. To have a bending resistance falling within that ranges is advantageous for the substrate sheet 12 to be taken out of the container 11 and spread out easily. The bending resistance of the substrate sheet 12 is obtained as an arithmetic average of the values measured in the machine direction (MD) and the cross-machine direction (CD).

The substrate sheet 12 may be a fiber sheet made up of fiber materials, such as a nonwoven fabric sheet. A substrate sheet 12 having a bending resistance in the range recited above before impregnation with the liquid cosmetic composition is obtained by properly selecting the type of the fiber making up the substrate sheet 12, the method for making the substrate sheet 12, the shape of the sheet, and the like. With respect to the type of the fiber, it is advantageous that the substrate sheet 12 contain cellulose fibers. The substrate sheet 12 containing cellulosic fibers as a constituent fiber exhibits high retention capacity for the liquid cosmetic composition. Furthermore, it is preferred for the substrate sheet 12 to contain thermoplastic resin fibers as well as cellulosic fibers in order to obtain moderate bending resistance and drape, to make finger combing easy, and to prevent the substrate sheet 12 impregnated with the liquid cosmetic composition from fuzzing or breaking during hair and scalp cleaning.

The cellulosic fiber is used to construct the substrate sheet 12 primarily for the purpose of imparting high retention capacity for the liquid cosmetic composition to the substrate sheet 12. The cellulosic fibers include hydrophilic fibers, such as natural fibers and regenerated fibers. Examples of the natural cellulosic fibers include cotton and pulp. Examples of the regenerated cellulosic fibers include rayon, cuprammonium, Lyocell, and Tencel. These cellulosic fibers may be used individually or in combination of two or more thereof The thermoplastic resin fiber is used to construct the substrate sheet 12 primarily for the purpose of imparting moderate abrasion resistance to the substrate sheet 12. Examples of the thermoplastic resin for the thermoplastic resin fiber include polyolefin resins, such as polyethylene and polypropylene; polyester resins, such as polyethylene terephthalate; acrylic resins; and polyamide resins. These resins may be used individually or in combination of two or more thereof. The thermoplastic resin fibers may be made from a single composition consisting of only one kind of resin or a polyblend of two or more kinds of resins. The thermoplastic resin fibers may be sheath/core or side-by-side conjugate fibers having two or more kinds of resins. Inter alia, fibers of polyolefin resins, such as polyethylene and polypropylene, or fibers of polyester resins, such as polyethylene terephthalate, are preferred in terms of bending resistance and mechanical strength of the substrate sheet 12.

When the substrate sheet 12 contains cellulosic fibers and thermoplastic resin fibers, the cellulosic to thermoplastic resin ratio in the substrate sheet 12 is decided with considerations given to the bending resistance and mechanical strength of the substrate sheet 12 and the liquid cosmetic composition retention capacity of the substrate sheet 12. For instance, the proportion of the cellulosic fibers in the mass of the substrate sheet 12 before impregnation with the liquid cosmetic composition is preferably 30 mass % or more, more preferably 35 mass % or more, even more preferably 40 mass % or more, still even more preferably 50 mass % or more. The proportion of the cellulosic fibers is preferably 99 mass % or less, more preferably 97 mass % or less, even more preferably 95 mass % or less. The proportion of the thermoplastic resin fibers in the mass of the substrate sheet 12 before impregnation with the liquid cosmetic composition is preferably 1 mass % or more, more preferably 3 mass % or more, even more preferably 5 mass % or more, still even more preferably 25 mass % or more. The proportion of the thermoplastic resin fibers is preferably 70 mass % or less, more preferably 65 mass % or less, even more preferably 60 mass % or less, still even more preferably 50 mass % or less. Specifically, the proportion of the cellulosic fibers is preferably 30 mass % to 99 mass %, more preferably 35 mass % to 97 mass %, even more preferably 40 mass % to 95 mass %, still even more preferably 50 mass % to 95 mass %, relative to the mass of the substrate sheet 12 before impregnation with the liquid cosmetic composition. The proportion of the thermoplastic resin fibers is preferably 1 mass % to 70 mass %, 3 mass % to 65 mass %, even more preferably 5 mass % to 60 mass %, still even more preferably 25 mass % to 50 mass %, relative to the mass of the substrate sheet 12 before impregnation with the liquid cosmetic composition. In particular, it is preferred that the proportion of the cellulosic fibers be larger than that of the thermoplastic resin fibers in the substrate sheet 12.

For easy control of bending resistance of the substrate sheet 12 in making the substrate sheet 12, the substrate sheet 12 is preferably made by a production system that does not involve bonding of fiber intersections. Such a production system can include techniques for making nonwoven fabric, such as a hydroentanglement process and a needle punching process. A hydroentanglement process is especially preferred for obtaining a substrate sheet 12 with low bending resistance and high drape. A substrate sheet 12 made by hydroentanglement is able to retain the form of nonwoven fabric only through entanglement of constituent fibers. As the case may be, the form of nonwoven fabric may be retained not only by the fiber entanglement but also by bonding part of the fiber intersections by fusion bonding or with adhesive.

When the substrate sheet 12 is made by a hydroentanglement process, the substrate sheet 12 is prepared by forming a loose web of fibers and applying jets of fluid to the web. The fluid to be jetted is preferably liquid. Gas may be used as fluid in some cases. Water is used to advantage as fluid for ease of handling. The degree of fiber entanglement to be achieved by hydroentanglement is adjustable by adjusting the pressure and the like in striking the jets of fluid into the web, whereby the bending resistance of the resulting substrate sheet 12 may be adjusted.

In order for the substrate sheet 12 to retain an ample amount of the liquid cosmetic composition for cleaning both hair and scalp and to perform the hair and scalp cleaning operation smoothly, the apparent area of the substrate sheet 12 is preferably 50 $cm^2$ or more, more preferably 100 $cm^2$ or more, even more preferably 200 $cm^2$ or more. From the same point of view, the apparent area is preferably 1600 $cm^2$ or less, more preferably 900 $cm^2$ or less, even more preferably 700 $cm^2$ or less. Specifically, the apparent area of the substrate sheet 12 is preferably 50 $cm^2$ to 1600 $cm^2$, more preferably 100 $cm^2$ to 900 $cm^2$, even more preferably 200 $cm^2$ to 700 $cm^2$. As used herein, the term "apparent area" means the area of the region defined by the outline of a sheet spread out and placed flat. Therefore, even if a substrate sheet 12 has a three-dimensional texture or perforations, this does not influence the apparent area of the substrate sheet 12.

The mass of the substrate sheet 12 before being impregnated with the liquid cosmetic composition is also influential on the impregnation retention capacity of the substrate sheet 12 and ease of hair and scalp cleaning operation. From this viewpoint, the mass of the substrate sheet 12 before impregnation with the liquid cosmetic composition is preferably 0.5 g or more, more preferably 1.0 g or more, even more preferably 1.5 g or more, and preferably 8.0 g or less, more preferably 6.0 g or less, even more preferably 4.0 g or less. Specifically, the mass of the substrate sheet 12 before impregnation with the liquid cosmetic composition is preferably 0.5 g to 8.0 g, more preferably 1.0 g to 6.0 g, even more preferably 1.5 g to 4.0 g.

In connection with the mass of the substrate sheet 12, the substrate sheet 12 before impregnation with the liquid cosmetic composition preferably has a basis weight of 10 g/m² or more, more preferably 15 g/m² or more, even more preferably 20 g/m² or more, still even more preferably 25 g/m² or more, with the object of imparting moderate bending resistance (or drape) to provide improved operationality in hair treatment by finger combing and securing sufficient retention capacity for the liquid cosmetic composition. With the same object, the basis weight of the substrate sheet 12 before impregnation with the liquid cosmetic composition is preferably 200 g/m² or less, more preferably 150 g/m² or less, even more preferably 100 g/m² or less, still even more preferably 80 g/m² or less. Specifically, the basis weight of the substrate sheet 12 before impregnation with the liquid cosmetic composition is preferably 10 g/m² to 200 g/m², more preferably 15 g/m² to 150 g/m², even more preferably 20 g/m² to 100 g/m², still even more preferably 25 g/m² to 80 g/m².

With respect to the thickness of the substrate sheet 12 before impregnation with the liquid cosmetic composition, it is preferred that the substrate sheet 12 before impregnation with the liquid cosmetic composition be thin in the interests of portability but be thick in the interests of retention capacity for the liquid cosmetic composition and also in terms of abrasion resistance. With the balance of these factors taken into consideration, the thickness of the substrate sheet 12 before impregnation with the liquid cosmetic composition is preferably more than 0.3 mm, more preferably 0.4 mm or more, even more preferably 0.5 mm or more, still even more preferably 0.7 mm or more, yet even more preferably 0.8 mm or more. With the same object, the thickness of the substrate sheet 12 before impregnation with the liquid cosmetic composition is preferably 5 mm or less, more preferably 4 mm or less, even more preferably 3 mm or less, still even more preferably 1.3 mm or less. Specifically, the thickness of the substrate sheet 12 before impregnation with the liquid cosmetic composition is preferably more than 0.3 mm and not more than 5 mm, more preferably 0.4 mm to 4 mm, even more preferably 0.5 mm to 3 mm, still even more preferably 0.7 mm to 3 mm. The thickness of the substrate sheet 12 is measured according to the "Methods for measuring thickness of fabrics and textile products" specified in JIS L1096:2010. The measurement is made under a load of 0.3 kPa using, for example, a thickness gauge FS-60DS available from Daiei Kagaku Seiki.

In order to control the bending resistance and impregnation retention capacity of the substrate sheet 12, the substrate sheet 12 may be provided on one or both sides thereof with a three-dimensional texture or may be perforated.

The substrate sheet 12 having a three-dimensional textured surface is advantageous in that (1) cushioning properties are imparted to reduce physical irritation to hair or scalp during hair cleaning and (2) the substrate sheet 12 is made more pliable and, when put on a hand to cover the fingers, more conformable to the hand. The three-dimensional textured surface may include raised portions and/or recessed portions arranged in dots discretely or in lines extending in a specific direction in the plane of the substrate sheet 12. With a view to uniformly applying the liquid cosmetic composition to hair to provide better hair fixing, it is preferred that the three-dimensional texture extends in a plurality of lines in one direction in the plane of the substrate sheet 12. This is because, the inventors believe, hair strands will fit into the recessed portions extending in one direction when treated or cleaned with the substrate sheet 12 by finger combing thereby acquiring an increased contact area with the sheet-like hair care product and enjoying more uniform application of the liquid cosmetic composition. Furthermore, because of the sheet form of the sheet-like hair care product, the palmer side of a user's hand is in contact with the liquid cosmetic composition for a long time during the cleaning/treating operation. Therefore, if the liquid cosmetic composition contains an ingredient that tends to feel sticky, such as a polymer, the user is likely to feel the liquid cosmetic composition sticky on their hand. To alleviate such an unpleasant feel, the substrate sheet 12 is preferably provided with a three-dimensional texture on not only its side to be applied to hair but also the opposite side to be contacted by the hand of a user, namely, on both sides thereof. When the substrate sheet 12 is provided with a three-dimensional texture on both sides thereof, wherever the surface of one side of the substrate sheet 12 is recessed, the corresponding surface on the other side may be either raised or recessed. Likewise, wherever the surface of one side is raised, the corresponding surface on the other side may be either raised or recessed.

In the case when the substrate sheet 12 has a three-dimensional textured surface on both sides thereof, it is preferred that the locations of raised portions on one side substantially correspond to the locations of raised portions on the other side in a plan view from the standpoint of controlling the release of the liquid cosmetic composition and applying the liquid cosmetic composition to hair thinly and uniformly. With the liquid cosmetic composition applied to hair thinly and uniformly by the use of such a three-dimensionally textured substrate sheet 12, the hair is made manageable into a natural style without unruly strands of hair under control.

When the substrate sheet 12 has a three-dimensional textured surface on both sides thereof, it is preferred that the thickness of the substrate sheet 12 not be uniform from the viewpoint of controlling the release of the liquid cosmetic composition and applying the liquid cosmetic composition to hair thinly and uniformly. For example, when the height difference $D_a$ from the bottom of a recessed portion to the top of a raised portion on one side and that $D_b$ on the other side are measured (see FIG. 3), the side having a larger height difference is designated a first side. It is preferred that the thickness of the sheet measured at the raised portion on the first side be larger than that measured at the recessed portion on the first side. The thickness at the raised portion and the thickness at the recessed portion are thicknesses of portions where fibers actually exist. The thicknesses at these portions are measured by cutting the substrate sheet with a razor and observing the section under a microscope.

The three-dimensionally textured substrate sheet 12 preferably has different basis weights between the raised portions and the recessed portions in terms of retention capacity for the liquid cosmetic composition and release of the liquid cosmetic composition. Specifically, the basis weight at the raised portions is preferably larger than that at the recessed portions so as to retain a large amount of the liquid cosmetic composition and easily release the liquid cosmetic composition under the wiping pressure. With reference to the basis weight, the raised portions preferably have a larger basis weight than the recessed portions with the same object.

The basis weights of the raised portions and the recessed portions can be obtained by separately cutting out raised portions and recessed portions, measuring the mass and the area of the cutout raised portions and the cutout recessed portions, and dividing the mass by the area. The areas of the raised portions and the recessed portions may be obtained by using a hereinafter described image analysis system or by the method below. When recessed portions have perforations, the basis weight of the recessed portions is calculated based on the area of the recessed portions exclusive of the perforations. On the other hand, the overall basis weight of the substrate sheet 12 is calculated based on the area inclusive of the area of the perforations, namely the apparent area of the sheet.

Method for calculating basis weights of raised portions and recessed portions:

(1) A 10 cm by 10 cm piece is cut out of a substrate sheet.
(2) The cut piece is cut into raised portions and recessed portions. The total mass (g) of the cutout raised portions and the total mass (g) of the cutout recessed portions are measured precisely to the tenth of a milligram.
(3) A 10 cm by 10 cm square sheet of mounting paper is provided for use as a standard area sheet. All the pieces cut out of the substrate sheet as raised portions (all the cutout raised portions) are duplicated on a copier, and so is the standard area sheet. The image of the standard area sheet and the image of the individual cutout raised portions are cut out from their copies. Each of the cutout copy of the standard area sheet and a group of cutout pieces of the copy of individual raised portions is weighed precisely to the tenth of a milligram. The total area of all the cutout raised portions is calculated from expression:

[Total area (m$^2$) of all cutout raised portions]=[mass (g) of all pieces cut out of the copy of raised portions]/[mass (g) of cutout copy of standard area sheet]/100.

(4) The basis weight of the raised portions is calculated from expression:

[Basis weight (g/m$^2$) of raised portions]=[total mass (g) of raised portions]/[total area (m$^2$) of all cutout raised portions].

(5) The total area (m$^2$) of all the cutout recessed portions and the basis weight (g/m$^2$) of the recessed portions are calculated similarly, provided that the area of perforations, if any, is excluded.

To perforate the recessed portion provides the following advantage: the recessed portion having a hole (perforation) has a decreased relative area so that the impregnating liquid cosmetic composition held by the substrate sheet 12 is apt to be localized in the raised portions and is readily delivered or transferred to hair on being compressed by wiping pressure. When the substrate sheet 12 is a perforated sheet, the perforations may be arranged in a dot pattern in the raised and the recessed portions or localized in a specific region in the plane of the substrate sheet 12. The shape of the perforation may be isotropic, such as circular or regular polygonal, or anisotropic, such as elliptic. The perforation may go through the thickness of the substrate sheet 12 or may not go through but allow part of the fibers constituting the substrate sheet 12 to remain to form a thin film or a low-basis weight region.

It is desirable for the sheet-like hair care product of the invention to retain a large amount of the liquid cosmetic composition so as to achieve sufficient hair cleaning and/or making hair manageable by controlling unruly hair by what we call a water set effect. For example, the substrate sheet 12 preferably has a maximum water retention of 700 mass % or more, more preferably 800 mass % or more, even more preferably 900 mass % or more, still even more preferably 1000 mass % or more. While the upper limit is not particularly limited, it is preferably, for example, 2000 mass % or less, more preferably 1500 mass % or less, even more preferably 1300 mass % or less. The maximum water retention is determined by "Test methods for nonwovens: 6.9.2 Water retention" specified in JIS L1913:2010. The thus obtained maximum water retention is multiplied by the mass of the substrate sheet 12 to give the maximum water content.

Figure 2:
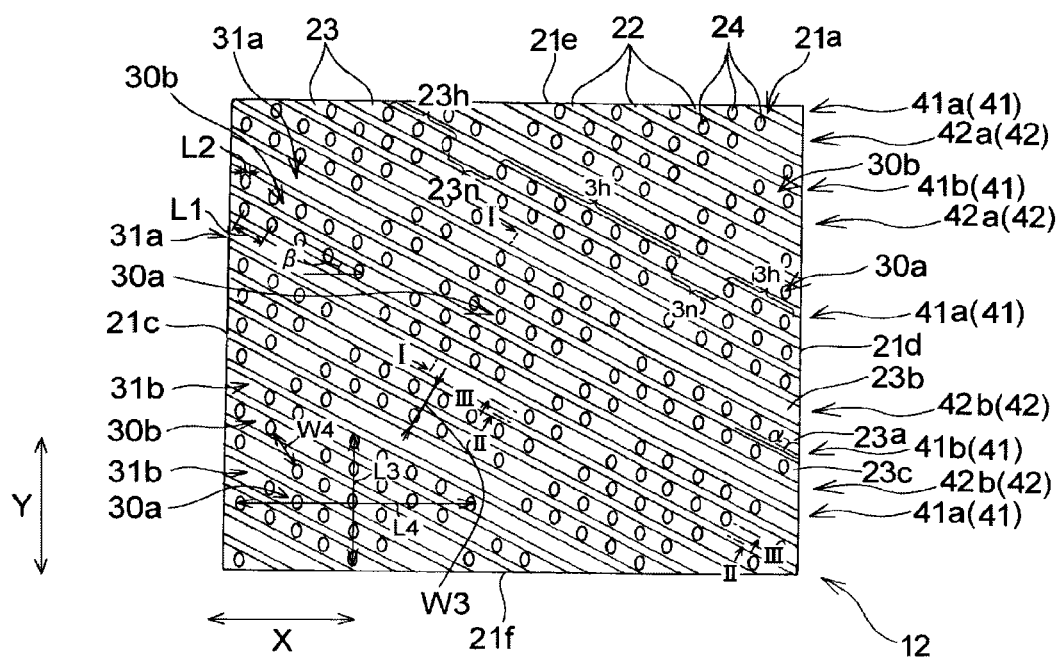
FIG. 2 is a plan of an example of the substrate sheet suitably used in the invention.

In FIG. 2 is shown an example of the substrate sheet 12 suited for use in the sheet-like hair care product of the present embodiment. The substrate sheet 12 includes raised portions, recessed portions, and perforations. The substrate sheet 12 has a first side 21a and a second side 21b located opposite to the first side 21a. The substrate sheet 12 has alternating ridges 22 as protrusions and grooves 23 as depressions formed on the first side 21a and the second side 21b at mutually corresponding locations. By the phrase "at mutually corresponding locations" is meant that the locations of the ridges 22 and the grooves 23 on the first side 21a are coincident with those on the second side 21b. The ridges 22 and the grooves 23 on both sides 21a and 21b extend in parallel to one another in a direction intersecting two parallel sides 21c and 21 d of the substrate sheet 12. The substrate sheet 12 has a rectangular shape defined by four straight sides; a pair of parallel opposite sides 21d and 21d (right and left in FIG. 2) and a pair of parallel opposite sides 21e and 21f (upper and lower in FIG. 2). The right and left sides 21d and 21c and the upper and lower sides 21e and 21f are perpendicular to each other. The direction of the right and left sides 21d and 21c will be designated as direction Y, and the direction of the upper and lower sides 21e and 21f as direction X.

The ridges 22 and the grooves 23 on the first side 21a alternate with each other in a parallel relationship over the entire area of the substrate sheet 12. Each of the ridges 22 and the grooves 23 intersects each of the parallel opposite sides 21c and 21d at an angle α. The angle α is preferably 30° or greater, more preferably 45° or greater, and preferably 80° or smaller, and is preferably 30° to 80°, more preferably 45° to 80°, from the standpoint of a wiping property of the hair sweat, fat dirt or the like.

Figure 3:
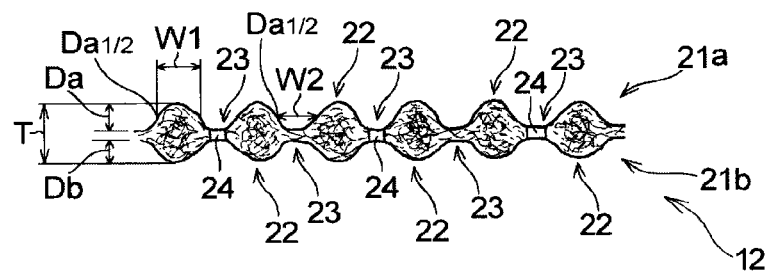
FIG. 3 is a cross-sectional view taken along line I-I in FIG. 2.
Figure 4A:
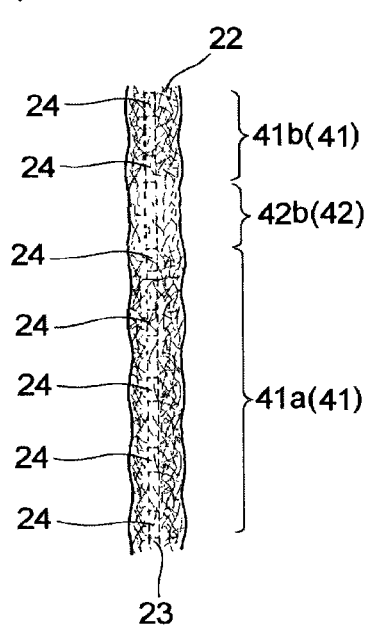
FIG. 4(a) is a cross-sectional view taken along line II-II in FIG. 2.

As is apparent from FIG. 3 illustrating a vertical cross-section of the substrate sheet 12, each ridge 22 on the first side 21a has an upwardly convex profile, and the ridges 22 of the same shape and size are arranged at substantially regular intervals in direction X in FIG. 3. As shown in FIG. 4(a), each ridge 22 on the first side 21a has an almost constant thickness along its extending direction. As shown in FIG. 3, each groove 23 on the first side 21a is formed between every pair of adjacent ridges 22. Although there is no distinct boundary between a ridge 22 and a groove 23, the boundary is defined as follows for convenience. Taking the first side 21a for instance, the position $D_{a1/2}$ at half the height difference $D_a$ at the top of the ridge 22 (i.e., the distance between the top of the ridge 22 and the bottom of the groove except a perforation 24 described infra) is taken as the position of the boundary (see FIG. 3). In the cross-section of FIG. 3, each ridge 22 on the second side 21b, which has a smaller height difference than that on the first side 21a, has a downwardly convex profile, and the ridges 22 of the same shape and size are arranged at substantially regular intervals in the lateral direction in FIG. 3. As shown in FIG. 4(a), each ridge 22 on the second side 21b has an almost constant thickness along its extending direction similarly to the ridge 22 on the first side 21a. Every groove 23 on the second side 21b is formed between every pair of adjacent ridges 22 similarly to the grooves 23 on the first side 21a. Accordingly, in the cross-section of FIG. 3, the thickness of the substrate sheet 12 has a periodically changing thickness in the lateral direction. The term "thickness (or height)" as used herein with respect to the ridges 22 on each of the first side 21a and the second side 21b refers to, when focusing on the first side 21a, the distance from "the position $D_{a1/2}$ (in the case of the first side 21a) at half the height difference $D_a$ (in the case of the first side 21a) at the top of the ridge 22)" to "the top of the ridge 22".

Each ridge 22 of the substrate sheet 21 has a width W1 in the lateral direction in FIG. 3. In the interests of operationality on use, the width W1 is preferably 0.5 mm or more, more preferably 0.8 mm or more, preferably 3.0 mm or less, specifically preferably 0.5 mm to 3.0 mm, more preferably 0.8 mm to 3.0 mm. Each groove 23 of the substrate sheet 21 has a width W2 in the lateral direction in FIG. 3. In view of removed dirt retaining properties, the width W2 is preferably 2.0 mm or more, more preferably 2.2 mm or more, and preferably 6.0 mm or less, more preferably 5.5 mm or less, specifically preferably 2.0 mm to 6.0 mm, more preferably 2.2 mm to 5.5 mm.

The height difference $D_a$ at the top of the ridge 22 on the first side 21a (see FIG. 3) is preferably 0.2 mm or more, preferably 1.2 mm or less, more preferably 1.0 mm or less, specifically preferably 0.2 mm to 1.2 mm, and more preferably 0.2 mm to 1.0 mm, from the viewpoint of hair/scalp cleaning operationality. The height difference $D_b$ at the top of the ridge 22 on the second side 21b (see FIG. 3) is preferably 0.1 mm or more, preferably 1.2 mm or less, more preferably 1.0 mm or less, specifically preferably 0.1 mm to 1.2 mm, and more preferably 0.1 mm to 1.0 mm, from the same viewpoint. The height differences $D_a$ and $D_b$ are measured on a cross-sectional image of the substrate sheet 12 acquired using a microscope VH-8000 from Keyence at a magnification of 50 to 200. A cross-section of the substrate sheet 12 is prepared by cutting in direction X using a razor FAS-10 from Feather Safety Razor Co., Ltd.

As shown in FIGS. 2 and 3, the substrate sheet 12 has perforations 24 going through the grooves 23 on both sides 21a and 21b. Each groove 23 consists of alternating perforated portions 23h having a perforation and non-perforated portions 23n in a plan view as shown in FIG. 2. Specifically, each perforated portion 23h has alternating perforated portions 23h and non-perforated portions 23n along its extending direction, and each perforated portion 23h has one to seven perforations 24. Out of the perforated portions 23h possessed by one groove 23, those having two or more perforations 24 have the perforations 24 at regular intervals in their extending direction.

Each perforation 24 is preferably formed by pushing aside and rearranging the fibers constituting the substrate sheet 12. The perforations 24 may take on various shapes in a plan view. The plan view shape of the perforations 24 is not particularly limited and includes, for example, circular, elongated circular, elliptic, triangular, rectangular, and hexagonal shapes or combinations thereof.

With a view of localizing the liquid cosmetic composition in the raised portions to improve transfer to hair and achieving moderate bending resistance while maintaining mechanical strength, the distance L1 (see FIG. 2) between adjacent perforations 24 in the extending direction of the groove 23 is preferably 4.0 mm or more and 15.0 mm or less, more preferably 8.0 mm or less, specifically preferably 4.0 mm to 15.0 mm, more preferably 4.0 mm to 8.0 mm. From the viewpoint of release of the liquid cosmetic composition, the diameter (or the minor axis length) L2 (see FIG. 2) of the individual perforations 24 is preferably 0.7 mm or more, more preferably 0.75 mm or more, preferably 3.0 mm or less, more preferably 2.70 mm or less. For example, the diameter L2 is preferably 0.7 mm to 3.0 mm, more preferably 0.75 mm to 2.70 mm. With a view to mechanical strength and bending resistance, the ratio of the diameter L2 (see FIG. 2) of the perforation 24 to the width W2 (see FIG. 3) of the groove 23, L2×100/W2, is preferably 20% or more, more preferably 30% or more, preferably 90% or less, preferably 20% to 90%, more preferably 30% to 90%.

With a view to release of the liquid cosmetic composition, the size of the individual perorations 24 is preferably 0.5 $mm^2$ or more, more preferably 1 $mm^2$ or more, preferably 20 $mm^2$ or less, more preferably 10 $mm^2$ or less, specifically preferably 0.5 $mm^2$ to 20 $mm^2$, more preferably 1 $mm^2$ to 10 $mm^2$, in terms of a plan-view projected area. The size of the perforations 24 can be measured using an image analysis system. Specifically, a picture of the substrate sheet 12 is scanned into a computer using a light source (Sunlight SL-230K2 from LPL), a copy stand (Copy Stand CS-5 from LPL), a lens (24 mm/F2.8D Nikkor Lens from Nikon Corp.), a CCD camera (HV-37 from Hitachi Electronics Co., Ltd., with the lens connected thereto via an F mount), and a video card (Spectra 3200 from Canopus Co., Ltd.). The acquired image is processed by image analysis software NEW QUBE (ver. 4.20) from NEXUS to binarize the image of the perforations 24. An average of the areas of the individual perforations 24 obtained from the binarized image is taken as the size of the perforations 24.

The length of the non-perforated portions 23n in the extending direction of the groove 23 is preferably longer than the shortest distance between adjacent perforations 24 in the extending direction of the groove 23. In other words, the distance between the two perforations 24 located nearest to both ends of the non-perforated portion 23n is preferably longer than the distance between adjacent perforations 24 in the perforated portion 23h.

The pattern of arranging the perforated portions 23h and the non-perforated portions 23n of the grooves 23 is different between one groove 23 and the adjacent groove 23. Taking a groove 23a shown in FIG. 2 for instance, the groove 23a has, from the lower right to the upper left (from the side 21d to the side 21c), a perforated portion 23h having six perforations 24, a non-perforated portion 23n, a perforated portion 23h having five perforations 24, a non-perforated portion, a perforated portion 23h having two perforations, and a non-perforated portion. A groove 23b shown in FIG. 2, which is upwardly adjacent to the groove 23a, has, from the lower right to the upper left (from the side 21d to the side 21c), a non-perforated portion 23n, a perforated portion 23h having five perforations 24, a non-perforated portion 23n, a perforated portion 23h having two perforations 24, a non-perforated portion 23n, and a perforated portion 23h having five perforations 24. A groove 23c shown in FIG. 2, which is downwardly adjacent to the groove 23a, has, from the lower right to the upper left (from the side 21d to the side 21c), a perforated portion 23h having seven perforations 24, a non-perforated portion 23n, a perforated portion 23h having five perforations 24, a non-perforated portion 23n, and a perforated portion 23h having six perforations 24. In that way, the arrangement pattern of perforated portions 23h and non-perforated portions 23n in the groove 23a and those in the upwardly and downwardly adjacent grooves 23b and 23c are all different from one another.

In its whole plan view, the substrate sheet 12 includes: perforated regions 41 each having a group of perforated portions 23h of a plurality of grooves 23; and non-perforated regions 42 each having a group of non-perforated portions 23n of a plurality of grooves 23. The perforated regions 41 and the non-perforated regions 42 are arranged in their respective patterns. For example, the perforated regions 41 are arranged in a periodically repetitive pattern of specific shapes, such as diamond shapes and V shapes, in the extending direction of the perforated regions 41 (direction X). The non-perforated regions 42 are arranged in a periodically repetitive pattern of specific shapes, such as V shapes in the extending direction of the non-perforated regions 42 (direction X). More specifically, in the whole plan view of the substrate sheet 12, the perforated regions 41 include first perforated subregions 41a and second perforated subregions 41b. As shown in FIG. 2, the first perforated subregion 41a is composed of a plurality of diamond-shaped groups 30a including perforated portions 23h of a plurality of grooves 23 (hereinafter referred to as diamond-shaped, perforated portion group(s) 30a), the plurality of diamond-shaped, perforated portion groups 30a being arranged in direction X at a given interval. The second perforated subregion 41b is composed of a plurality of V-shaped groups 30b including perforated portions 23h of a plurality of grooves 23 (hereinafter referred to as V-shaped, perforated portion group(s) 30b), the plurality of V-shaped, perforated portion groups 30b being repeatedly arranged in direction X. The first perforated subregions 41a and the second perforated subregions 41b alternate in direction Y at a given interval. Still more specifically, a second perforated subregion 41b and the adjacent second perforated subregion 41b in direction Y are offset by a half pitch in direction X. Between a V-shaped, perforated portion group 30b of a second perforated subregion 41b and an adjacent inverted V-shaped, perforated portion group 30b which is offset by a half pitch in direction Y (a half pitch-offset V-shaped, perforated portion group 30b) is arranged a diamond-shaped, perforated portion group 30a of the first perforated subregion 41a. Thus, the perforated region 41 repeatedly alternates in direction Y, which is perpendicular to the extending direction of the perforated region 41 (direction X), so as to sandwich the non-perforated region 42. Every pair of the perforated regions 41 having a specific shape, such as a diamond or V shape, that are adjacent to each other in direction Y are offset with respect to each other by a half pitch. The non-perforated region 42 alternates in direction Y, which is perpendicular to the extending direction of the non-perforated region 42 (direction X), so as to sandwich with the perforated region 41. The non-perforated region 42 having a specific shape, such as a V shape, is offset from at least one of the adjacent non-perforated regions 42 in direction Y by a half pitch.

From the standpoint of mechanical strength and bending resistance, the diamond-shaped, perforated portion groups 30a forming the first perforated subregion 41a each preferably have a dimension L3 (see FIG. 2) in direction Y of 20 mm or more, more preferably 25 mm or more, preferably 110 mm or less, more preferably 100 mm or less, specifically preferably 20 mm to 110 mm, more preferably 25 mm to 100 mm, and a dimension L4 (see FIG. 2) in direction X of 20 mm or more, more preferably 25 mm or more, preferably 60 mm or less, more preferably 50 mm or less, specifically preferably 20 mm to 60 mm, more preferably 25 mm to 50 mm.

The V-shaped, perforated portion group 30b forming the second perforated subregion 41b has a constant width. From the standpoint of mechanical strength and bending resistance, the width W3 (see FIG. 2) of the V-shaped, perforated portion group 30b is preferably 8 mm or more, preferably 20 mm or less, more preferably 15 mm or less, specifically preferably 8 mm to 20 mm, more preferably 8 mm to 15 mm. One of the two diagonal portions of the V-shaped, perforated portion group 30b makes an angle β with a straight line extending in direction X. The angle β is preferably 10° to 40°. The other diagonal portion of the V-shaped, perforated portion group 30b is symmetrical to the first said diagonal portion about a line extending in direction Y. The second perforated subregion 41b consists of a repetition of the so formed V-shaped, perforated portion group 30b in direction X to take on a zigzag shape extending in direction X.

As described, the substrate sheet 12 has a pattern in which the first perforated subregions 41a and the second perforated subregions 41b alternate in direction Y at a given interval. The given interval corresponds to the non-perforated region 42 consisting of the non-perforated portions 23n of a plurality of grooves 23. The non-perforated region 42 is thus formed between every first perforated subregion 41a consisting of a plurality of diamond-shaped, perforated portion groups 30a arranged in direction X and every adjacent second perforated subregion 41b consisting of a plurality of V-shaped, perforated portion groups 30b connected in direction X as shown in FIG. 2. The non-perforated regions 42 of the substrate sheet 12 include first non-perforated subregions 42a and second non-perforated subregions 42b. The first non-perforated subregions 42a and second non-perforated subregions 42b are arranged to surround every diamond-shaped, perforated portion group 30a of the first perforated subregions 41a. The first non-perforated subregion 42a consists of a repetition of a V-shaped group 31a of the non-perforated portions 23n of a plurality of the grooves 23 (hereinafter referred to as a V-shaped, non-perforated portion group 31a) in direction X. The second non-perforated subregion 42b consists of a repetition of an inverted V-shaped group 31b of the non-perforated portions 23n of a plurality of the grooves 23 (hereinafter referred to as an inverted V-shaped, non-perforated portion group 31b). The second non-perforated subregion 42b is symmetrical to the first non-perforated subregion 42a about a bisector of the diamond-shaped, perforated portion group 30a in direction X. To put it another way, the first non-perforated subregion 42a and the second non-perforated subregion 42b are offset from each other by a half pitch in direction X. Similarly to the diagonal portion of the V-shape, perforated portion group 30b, one of the two diagonal portions of each V-shaped, non-perforated portion group 31a, which forms the first non-perforated subregion 42a, makes an angle β (see FIG. 2) with a straight line extending in direction X. The other diagonal portion of the V-shaped, non-perforated portion group 31a is symmetrical to the first said diagonal portion about a line extending in direction Y. The first non-perforated subregion 42a consists of a repetition of the so formed V-shaped, non-perforated portion group 31a in direction X to take on a zigzag shape extending in direction X similarly to the second perforated subregion 41b. Likewise, the second non-perforated subregion 42b consists of a repetition of the inverted V-shaped non-perforated portion group 31b in direction X so as to take on a zigzag shape extending in direction X.

The first non-perforated subregion 42a and the second non-perforated subregion 42b have the same width W4. Both the first non-perforated subregion 42a and the second non-perforated subregion 42b have a constant width W4. The width W4 is larger than the distance L1 (see FIG. 2) between adjacent perforations 24 in the extending direction of the groove 23. In view of mechanical strength and bending resistance, the width W4 (see FIG. 2) is preferably 5 mm or larger, more preferably 10 mm or larger, preferably 20 mm or less, specifically preferably 5 mm to 20 mm, more preferably 10 mm to 20 mm.

The perforated regions 41 (inclusive of subregions 41a and 41b) and the non-perforated regions 42 (inclusive of subregions 42a and 42b) are arranged in a manner such that the extending direction of the perforated regions 41 and the extending direction of the non-perforated regions 42 intersect the extending directions of the ridges 22 and grooves 23. Specifically, the perforated regions 41 including the first perforated subregions 41a and the second perforated subregions 41b extend in direction X. The non-perforated regions 42 including the first non-perforated subregions 42a and the second non-perforated subregions 42b extend in direction X, too. Both the perforated regions 41 and non-perforated regions 42 intersect the extending direction of the ridges 22 and the grooves 23.

Focusing on one ridge 22, as shown in FIG. 4(a), the portion of the ridge 22 that intersects a perforated region 41 (subregion 41a or 41b) and the portion of the ridge 22 that intersects a non-perforated region 42 (subregion 42a or 42b) have different basis weights. The portion of the ridge 22 that intersects a perforated region 41 (subregion 41a or 41b) has a greater basis weight than the portion of the ridge 22 that intersects a non-perforated region 42 (subregion 42a or 42b). From the viewpoint of maintaining a feeling of gripping by fingers, and the like, the basis weight of the portion of the ridge 22 that intersects the perforated region (subregion 41a or 41b) is preferably 60 $g/m^2$ or more, more preferably 65 $g/m^2$ or more, preferably 500 $g/m^2$ or less, more preferably 200 $g/m^2$ or less, specifically preferably 60 $g/m^2$ to 500 $g/m^2$, more preferably 65 $g/m^2$ to 200 $g/m^2$. From the viewpoint of mechanical strength and retention capacity for the liquid cosmetic composition, the basis weight of the portion of the ridge 22 that intersects the non-perforated region (subregion 42a or 42b) is preferably 40 $g/m^2$ or more, preferably 440 $g/m^2$ or less, more preferably 150 $g/m^2$ or less, specifically preferably 40 $g/m^2$ to 440 $g/m^2$, more preferably 40 $g/m^2$ to 150 $g/m^2$.

Figure 4B:
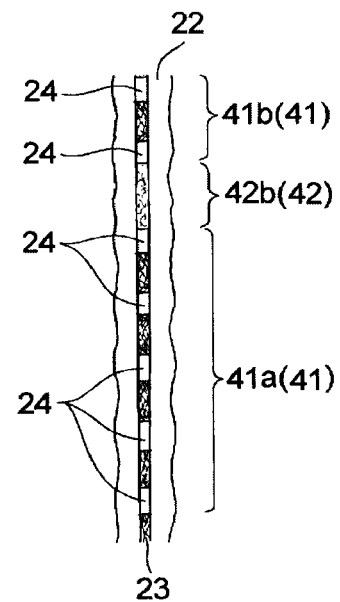
FIG. 4(b) is a cross-sectional view taken along line in FIG. 2.

Focusing on one groove 23 as shown in FIG. 4(b), the portion of the groove 23 that intersects a perforated region 41 (subregion 41a or 41b) and the portion of the groove 23 that intersects a non-perforated region 42 (subregion 42a or 42b) have different basis weights. The portion of the groove 23 that intersects a perforated region 41 (subregion 41a or 41b) has a greater basis weight than the portion of the groove 23 that intersects a non-perforated region 42 (subregion 42a or 42b). From the standpoint of maintaining the strength of the substrate sheet 12, the basis weight of the portion of the groove 23 that intersect the perforated region 41 (subregion 41a or 41b) is preferably 40 $g/m^2$ or more, preferably 210 $g/m^2$ or less, more preferably 110 $g/m^2$ or less, specifically preferably 40 $g/m^2$ to 210 $g/m^2$, more preferably 40 $g/m^2$ to 110 $g/m^2$. From the standpoint of the nonwoven fabric strength and liquid absorptivity, the basis weight of the portion of the groove 23 that intersects the non-perforated region 42 (subregion 42a or 42b) is preferably 20 $g/m^2$ or more, more preferably 25 $g/m^2$ or more, preferably 180 $g/m^2$ or less, more preferably 90 $g/m^2$ or less, specifically preferably 20 $g/m^2$ to 180 $g/m^2$, more preferably 25 $g/m^2$ to 90 $g/m^2$.

The above described substrate sheet 12 can be prepared by a hydroentanglement process in which a loose web is placed on a stainless steel or plastic wire having openings the shape and size of which correspond to those of the perforations 24 and which are arranged in alignment with the perforated regions 41 inclusive of subregions 41a and 41b.

The liquid cosmetic composition that impregnates the substrate sheet 12 will next be described. The liquid cosmetic composition is preferably made of a liquid capable of removing dirt from hair or scalp. In terms of handling and safety, the liquid cosmetic composition is preferably an aqueous solution containing water as a base. With the object of keeping the amount of the liquid cosmetic composition transferred from the substrate sheet 12 to hair constant, the liquid cosmetic composition preferably has a low viscosity. Taking these into consideration, it is preferred for the liquid cosmetic composition to contain water as a major component, an alcohol, and a surfactant. More preferably, the liquid cosmetic composition preferably contains ingredients (B-1), (B-2), and (B-3) as previously stated. These components will then be described in sequence.

The alcohol as ingredient (B-1) can be a monohydric or polyhydric alcohol. The monohydric alcohol may be chosen from saturated or unsaturated aliphatic alcohols preferably having 1 to 6 carbon atoms, more preferably 2 to 5 carbon atoms. The polyhydric alcohol may be chosen from saturated or unsaturated aliphatic alcohols preferably having 2 to 6 carbon atoms, more preferably 2 to 5 carbon atoms. These mono- and polyhydric alcohols may be used either individually or in combination of two or more thereof. Preferred alcohols include ethanol, propanol, isopropyl alcohol, 1,3-butylene glycol, dipropylene glycol, and glycerol.

The surfactant as ingredient (B-2) can be selected from those commonly used to clean hair and scalp. Such surfactants include cationic surfactants, anionic surfactants, amphoteric surfactants, and nonionic surfactants. Preferred of them are cationic surfactants with the object of smoothing the glide of the impregnated sheet-like hair care product on hair and easily applying the liquid cosmetic composition to hair. With a view to improving hair fixing performance, amphoteric surfactants or nonionic surfactants are preferred. From standpoint of facilitating uniform application of the liquid cosmetic composition to hair and improving hair fixing performance without leaving a sticky feel, a combination of a cationic surfactant and an amphoteric surfactant or a combination of a cationic surfactant and a nonionic surfactant is more preferred.

Examples of the cationic surfactant include alkyltrimethylammonium salts, alkoxyalkyltrimethylammonium salts, dialkyldimethylammonium salts, alkyldimethylamines and their salts, alkoxyalkyldimethylamines and their salts, and alkylamidoalkyldimethylamines and their salts.

Examples of the anionic surfactant include alkylbenzene sulfonates, alkyl or alkeny ether sulfates, alkyl or alkenyl sulfates, olefin sulfonates, alkane sulfonates, saturated or unsaturated fatty acid salts, alkyl or alkenyl ether carboxylates, α-sulfo fatty acid salts, N-acylamino acid surfactants, phosphoric mono- or diester surfactants, and sulfosuccinic esters.

Examples of the amphoteric surfactant include imidazoline surfactants, carbobetaine surfactants, amidobetaine surfactants, sulfobetaine surfactants, hydroxysulfobetaine surfactants, amidosulfobetaine surfactants, and amine oxide surfactants.

Examples of the nonionic surfactant include polyoxyalkylene alkyl ethers, polyoxyalkylene alkenyl ethers, higher fatty acid sucrose esters, polyglycerol fatty acid esters, higher fatty acid mono- or diethanolamides, polyoxyethylene hydrogenated castor oil, polyoxyethylene sorbitan fatty acid esters, polyoxyethylene sorbitol fatty acid esters, alkyl saccharide surfactants. These surfactants can be used either individually or in combination of two or more thereof.

The alcohol content of the liquid cosmetic composition is preferably 1 mass % or more, more preferably 5 mass % or more, even more preferably 10 mass % or more, preferably 45 mass % or less, more preferably 35 mass % or less, even more preferably 30 mass % or less. For example, the alcohol content in the liquid cosmetic composition is preferably 1 mass % to 45 mass %, more preferably 5 mass % to 35 mass %, even more preferably 10 mass % to 30 mass %.

The content of the surfactant in the liquid cosmetic composition is preferably 0.1 mass % or more, more preferably 0.2 mass % or more, even more preferably 0.3 mass % or more, preferably 5 mass % or less, more preferably 4 mass % or less, even more preferably 3 mass % or less, still even more preferably 2 mass % or less. For example, the surfactant content in the liquid cosmetic composition is preferably 0.1 mass % to 5 mass %, more preferably 0.2 mass % to 4 mass %, even more preferably 0.3 mass % to 3 mass %.

The liquid cosmetic composition may contain other ingredients enhancing various performances of the hair care product in addition to the alcohol, surfactant, and water. Such ingredients include (B-4) a silicone that will render hair easy to comb and provides increased comfort of use. Examples of useful silicones include polysiloxanes, modified silicones (e.g., amino-, oxazoline-, fluorine-, alcohol-, polyether-, epoxy-, or alkyl-modified silicones), and cyclic polysiloxanes. These silicones may be used either individually or in combination of two or more thereof. Inter alia, it is preferred to use one or more of polysiloxanes, polyether-modified silicones, oxazoline-modified silicones, and amino-modified silicones. Commercially available silicone products are useful as well. Examples of commercially available silicones include polysiloxanes, such as SH200 Fluid 1,000,000CS, BY11-026, and FZ-2231 (all from Dow Corning Toray Co., Ltd.) and TSF-451-100Ma (from Momentive Performance Materials Japan); polyether-modified silicones, such as TSF4440 (from Momentive Performance Materials Japan), KF-6005 and KF-6012 (both from Shin-Etsu Chemical Co., Ltd.), and SS-2910 (from Dow Corning Toray); amino-modified silicones, such as XF42-B8922 and XF42-C0330 (both from Momentive Performance Materials Japan), SF8451C, SF8452C, SF8457C, and SM8704C (all from Dow Corning Toray), and KF-867 (from Shin-Etsu Chemical); and a mixture of a polysiloxane and an amino-modified silicone, such as KF-1046 (from Shin-Etsu Chemical).

The liquid cosmetic composition preferably contains a silicone in an amount of 0.1 mass % or more, more preferably 0.2 mass % or more, even more preferably 0.3 mass % or more. The liquid cosmetic composition preferably contains a silicone in an amount of 5 mass % or less, more preferably 4 mass % or less, even more preferably 3 mass % or less, still even more preferably 1 mass % or less. For example, the liquid cosmetic composition preferably contains a silicone in an amount of 0.1 mass % to 5 mass %, more preferably 0.2 mass % to 4 mass %, even more preferably 0.3 mass % to 3 mass %.

The liquid cosmetic composition may further contain a cooling agent imparting a cooling sensation, such as menthol, a warming agent, a powder imparting smoothness and silkiness to the hair, a deodorant, an antiseptic, a fragrance, a chelating agent, and so forth.

The amount of the liquid cosmetic composition in the hair care product of the present embodiment is larger than in conventional sheet-like skin care cosmetics. This is because the hair care product of the present embodiment is aimed at cleaning both hair and scalp and also at causing a sufficient amount of the liquid cosmetic composition to penetrate hair to fix the hair while controlling unruly hair by what we call a water set effect. The amount of the liquid cosmetic composition is at least 1 g per sheet (substrate sheet 12). To have a sufficient amount of the liquid cosmetic composition penetrate the whole hair, the amount is preferably 6 g or more, more preferably 7 g or more, even more preferably 8 g or more, per sheet. The amount of the liquid cosmetic composition is 50 g or less, preferably 30 g or less, more preferably 25 g or less, even more preferably 20 g or less, still even more preferably 15 g or less, per sheet. For example, the total amount of the liquid cosmetic composition is preferably 1 g to 50 g, more preferably 6 g to 30 g, even more preferably 7 g to 25 g, still even more preferably 7 g to 20 g, yet even more preferably 8 g to 15 g, per sheet.

With the object of obtaining high retentivity of the substrate sheet 12 for the liquid cosmetic composition and increasing the amount of the liquid cosmetic composition delivered to the hair, the content of the liquid cosmetic composition of the substrate sheet 12 is preferably 5 mass % or more, more preferably 10 mass % or more, even more preferably 20 mass % or more, and preferably 90 mass % or less, more preferably 85 mass % or less, even more preferably 80 mass % or less, still even more preferably 60 mass % or less, relative to the maximum water content of the substrate sheet 12. The maximum water content of the substrate sheet 12 is calculated from the maximum water retention of the sheet 12. The maximum water content of the substrate sheet 12 is calculated from the maximum water retention. The maximum water retention is determined by "Test methods for nonwovens: 6.9.2 Water retention" specified in JIS L1913:2010. The thus obtained maximum water retention is multiplied by the mass of the substrate sheet 12 to give the maximum water content.

The thus constituted hair care product of the present embodiment is useful to handle perspiration or to fix hair after doing sports on the go or commuting; to remove cigarette or broiled meat odor from hair; to combat hay fever in the pollen season; to combat dry hair in the winter or frizzy and unruly hair in humidity weather; to substitute for hair washing in situations in which ample water is not available, such as in hospital, in a nursing home, during outdoor activities like climbing and camping, or a water outage; and to make hair manageable while controlling unruly strands of hair in such water shortage situations.

Sheet-like hair care products according second to sixth embodiments will then be described. Unless the context is specifically otherwise, the description of the first embodiment applies equally to the second to sixth embodiments.

In the second embodiment, the liquid cosmetic composition (B) contains (B-3) water and (B-5) a film-forming resin. Ingredient (B-5) is present in the liquid cosmetic composition in an amount of 0.01 mass % to 20 mass %.

As used herein, the term "film-forming resin" refers to a resin having a scratch hardness (by pencil test) of 6B to 3H as measured in accordance with JIS K5600-5-4. The term "scratch hardness (by pencil test)" refers to a film hardness determined in accordance with JIS 5600-5-4:1999, which is obtained by preparing a coating of a film-forming resin and pushing a pencil to the horizontal coating at a fixed angle of 45 degrees and constant load of 750 g. The scratch hardness (by pencil test) is reported in the range of 6B to 6H. A film with a scratch hardness (by pencil test) of 6B is graded "softest", and a film with a scratch hardness (by pencil test) of 6H is graded "hardest".

The second embodiment is more advantageous than conventional hairstyling product in that problems associated with conventional hair styling products such as mists and sprays are eliminated. That is, the second embodiment exhibits hairstyling performance as well as hair cleaning performance and hardly leaves its cosmetic ingredient on the hand of a user needlessly so that the user is less likely to feel any cosmetic ingredient sticky on the hand during or after use.

Because a conventional hair styling product is directly applied to the hair and then spread over therearound, there will be a portion of hair with a large amount of the preparation applied and a portion short of the preparation. Furthermore, when a user tries to uniformly spread the applied hair styling product to the neighboring hair strands, there is always time lab between application of the preparation and spreading of the applied preparation. Consequently, the water or alcohol content in the preparation can penetrate inside the hair or vaporize during the lagged time, making it difficult to uniformly spread the preparation wherever the preparation is applied, for example, from front to back or left to right of the scalp hair, from roots to tips of a bunch of hair, or from the outside to inside of a bunch of hair. Therefore, it has been difficult for a user to fix the whole hair into a natural style without an elaborate hair arrangement.

Furthermore, in the above described situations in which using water or a hair styling product is restricted, it has not been easy to satisfy the consumers' desires to fix messy hair or do up their hair beautifully.

Conventional dry shampoo sheets (e.g., those disclosed in Patent Literatures 1 and 2 cited supra) aim at cleaning hair, i.e., removal of sebum, sweat, smell or like dirt from hair and are designed without an intention to positively leave any active ingredient on the surface of hair strands. Accordingly, although they are excellent in effectively performing dirt removal, it is more likely that they fail to make a sufficient amount of a hairstyling ingredient, a sensory ingredient, and the like to remain on the hair as they are more effective in dirt removal. They are thus unsatisfactory in terms of fixing messy hair, styling the hair, and imparting a good feeling or touch to the hair. Mere application of known liquid cosmetic preparations, such as mists and sprays, to conventional dry shampoo sheets in an attempt to impart hairstyling capabilities to the dry shampoo sheets will result in an uncomfortable sensation of stickiness of the hand and will not sufficiently fulfill the consumers' desire to use the products in situations with restrictions on the use of water.

The second embodiment aims at the provision of a sheet-like hairstyling product that has hairstyling performance as well as hair cleaning performance and leaves no needless cosmetic ingredients on the user's hand so that the user may not feel stickiness or discomfort on the hand during or after use. The sheet-like hair care product of the present embodiment composed of the specific substrate sheet impregnated with the above described liquid cosmetic composition makes it possible for a user to apply and spread the liquid cosmetic composition on the hair while removing dirt from the hair. The film-forming resin is thereby applied to the hair thinly and uniformly to make the hair manageable and fix the hair in a natural way. The liquid cosmetic composition does not remain unnecessarily on the hand during and even after use and causes no sticky feeling. Therefore, the sheet-like hair care product of the present embodiment is particularly suited for hairstyling. The sheet-like hair care product of the present invention will also be called a sheet-like hairstyling product.

The sheet-like hairstyling product of the present embodiment, which has the substrate sheet impregnated with the liquid cosmetic composition containing ingredient (B-5), is capable of forming a thin and uniform film of ingredient (B-5) on the strands of hair, thereby enabling the user to fix the hair in a natural style without an elaborated hair arrangement. Since the liquid cosmetic composition contains ingredient (B-3), ingredient (B-5) is easily imparted to the hair. Because hydrogen bonds in hair are broken by ingredient (B-3), and in that state, ingredient (B-5) is imparted to the hair, the style of the hair lasts long easily. In other words, ingredient (B-3) not only acts as a solvent for ingredient (B-5) but functions to cleave the hydrogen bonds thereby to facilitate hairstyling.

The film-forming resin as ingredient (B-5) is capable of forming a coating film on hair strands upon being applied thereto. The coating film formed of the film-forming resin preferably has a scratch hardness (by pencil test) of lower (softer) than 3H, more preferably lower than 2H, even more preferably lower than H. Specifically, the scratch hardness (by pencil test) of the coating film is preferably 6B to 3H, more preferably 6B to H, even more preferably 6B to H. To use a resin capable of forming a film with a scratch hardness (by pencil test) falling in that range enables a user to fix the hair into a desired style. The coating film subjected to the pencil test in determining the scratch hardness is prepared by applying 2 g of a 10 mass % ethanolic solution of the film-forming resin to an area of 3 cm by 4 cm of a PET film and drying the applied resin solution at 25° C. and 50% RH for at least 24 hours.

The film-forming resin may be selected from those commonly used in the art as a hairstyling agent. Film-forming resins are classified according to chemical structure into cationic resins, anionic resins, nonionic resins, and amphoteric resins. Preferred of them are cationic resins for their non-stickiness on fingers and a hand. Cationic resins are also preferred for their capability of rendering hair moist, soft, and silky. Anionic resins are preferred with a view to creating a hair bunch texture of hair after use and imparting particularly high styling performance to the product. Nonionic resins are preferred with a view to reducing the friction between the hair and the sheet-like hairstyling product 13 thereby to improve the glide of the product on hair during use. Amphoteric resins are preferred with a view to giving a clean feeling to the hair. A nonionic resin, an amphoteric resin, and a combination thereof are preferred with a view to adding body and bounce to the hair after drying.

Examples of cationic resins that can be used in the invention include a vinylpyrrolidone-dimethylaminoethyl methacrylate copolymer diethylsulfate (e.g., H•C Polymer IS(M) and H•C Polymer 2, both from Osaka Organic Chemical Industry Co., Ltd.), a vinylpyrrolidone-dimethylaminopropylmethacrylamide-lauryldimethylaminopropylmethacrylamide copolymer (e.g., Styleze W-20 from ISP), poly(dimethylmethylenepiperidinium chloride) (e.g., Marquat 100 from Nalco Co.), a dimethyldiallylammonium chloride-acrylamide copolymer (e.g., Marquat 550 from Nalco Co.), vinylpyrrolidone-N,N-dimethylaminoethyl methacrylate copolymer diethylsulfate (e.g., Gafquat 734 from ISP), a vinylpyrrolidone-dimethylaminoethyl methacrylate copolymer (e.g., Gafquat 440 from ISP), an N,N-dimethylaminoethyl methacrylate diethylsulfate-N,N-dimethylacrylamide-polyethylene glycol dimethacrylate copolymer (e.g., Sofcare KG-101W-E and Sofcare KG-301P both from Kao Corp.), ammonium-modified hydroxyethyl cellulose (e.g., SofCat SL-30 Polymer from Kao Corp.), and an N-propionylpolyethyleneimine methylpolysiloxane copolymer (e.g., Elastomer OS from Kao Corp.). Preferred of them are a dimethyldiallylammonium chloride-acrylamide copolymer, a vinylpyrrolidone-N,N-dimethylaminoethyl methacrylate copolymer diethylsulfate, an N,N-dimethylaminoethyl methacrylate diethylsulfate-N,N-dimethylacrylamide-polyethylene glycol dimethacrylate copolymer, ammonium-modified hydroxyethyl cellulose, and an N-propionylpolyethyleneimine-methylpolysiloxane copolymer, with a view to further reducing a sticky feel on the hand or fingers during use and further improving hair moistness, softness, and silkiness.

Examples of useful anionic resins include an alkyl acrylate-diacetoneacrylamide copolymer (e.g., Plascize L-9540B, Plascize L-53P, and Plascize L-9909B, all from Goo Chemical Co., Ltd.), an alkyl acrylate-octylacrylamide copolymer (e.g., Dermacryl 79 from Akzo Nobel), a vinyl acetate-crotonic acid-vinyl neodecanoate copolymer (e.g., Resyn 28-2930, from Akzo Nobel), an acrylic acid-acrylamide-ethyl acrylate copolymer (e.g., Ultrahold 8 and Ultrahold Strong, both from BASF), an alkyl acrylate copolymer (e.g., Aniset NF-1000 and Aniset HS-300, both from Osaka Organic Chemistry), a polyethylene glycol-polypropylene glycol-25-dimethicone-acrylates copolymer (e.g., Lubiflex SILK, from BASF), and an isophorone diisocyanate-dimethylolpropionic acid-(polyoxyethylene-polyoxypropylene) 4,4'-isopropylidenediphenol copolymer (e.g., DynamX from Akzo Nobel). From the viewpoint of creating more attractive hair bundle texture after use and imparting particularly high styling performance to the product, preferred of them are an alkyl acrylate-diacetoneacrylamide copolymer, a vinyl acetate-crotonic acid-vinyl neodecanoate copolymer, and an isophorone diisocyanate-dimethylolpropionic acid-(polyoxyethylene-polyoxypropylene) 4,4'-isopropylidenediphenol copolymer.

Examples of the nonionic resins include polyvinylpyrrolidone (e.g., Luviskol K17, Luviskol K30, and Luviskol K90, all from BASF), vinylpyrrolidone-vinyl acetate copolymers (e.g., Luviskol VA73E and Lubiskol 37E, both from BASF), vinyl methyl ether-alkyl maleate copolymers (e.g., Gantrez A-425 and Gantrez ES-225, both from ISP), vinylpyrrolidone-methacrylamide-vinylimidazole copolymers (e.g., Luviset Clear from BASF), and polyvinylcaprolactam (e.g., Lubiskol Plus from BASF). From the viewpoint of securing smooth glide between hair and the sheet during use and adding body and bounce to the hair after drying, preferred of them are polyvinylpyrrolidone, vinylpyrrolidone-vinyl acetate copolymers, and vinyl methyl ether-alkyl maleate copolymers.

Examples of amphoteric resins include acrylates-lauryl acrylate-stearyl acrylate-ethylamine oxide methacrylate copolymers (e.g., Diaformer Z651 from Mitsubishi Chemical Corp.), methacryloyloxyethylcarboxybetaine-alkyl methacrylate copolymers (e.g., Yukaformer M75 and Yukaformer R205, both from Mitsubishi Chemical), octylacrylamide-hydroxypropyl acrylate-butylaminoethyl methacrylate copolymers (e.g., Amphomer 28-4910 from Akzo Nobel), and octylacrylamide-hydroxypropyl acrylate-butylaminoethyl methacrylate copolymers (e.g., Amphomer SH30 from Akzo Nobel). With a view to further increasing a fresh and clean feeling of the hair and adding body and bounce to the hair after drying, preferred of them acrylates-lauryl acrylate-stearyl acrylate-ethylamine oxide methacrylate copolymers, methacryloyloxyethylcarboxybetaine-alkyl methacrylate copolymers methacryloyloxyethylcarboxybetaine-alkyl methacrylate copolymers, acylacrylamide-hydroxypropyl acrylate-butylaminoethyl methacrylate copolymers.

The film forming resins described above can be used either individually or in combination of two or more thereof. The content of the film forming resin in the liquid cosmetic composition is 0.01 mass % or more, preferably 0.05 mass % or more, more preferably 0.1 mass % or more, with a view to improving hairstyling performance; and 20 mass % or less, preferably 10 mass % or less, more preferably 5 mass % or less, with a view to reducing a sticky feeling on the fingers and hand during application while retaining the hairstyling performance and reducing the feel of the liquid cosmetic composition remaining on the fingers and hand after application and drying. The film forming resin content in the liquid cosmetic composition in that range allows for (1) easily shaping or placing the hair into a desired style and (2) imparting an appropriate viscosity to the liquid cosmetic composition to enable a sufficient amount of the liquid cosmetic composition to be infiltrated into the substrate sheet. The film forming resin imparts a sufficient viscosity to the liquid cosmetic composition to prevent the liquid cosmetic composition from dripping off the substrate sheet. Water as ingredient (B-3) makes up the rest.

In addition to the film forming resin and water, the liquid cosmetic composition used in the second embodiment may further contain at least one of the aforementioned surfactant (B-2) and the aforementioned alcohol (B-1). These ingredients may be used as a viscosity modifier for the liquid cosmetic composition, a plasticizer for an ingredient of the liquid cosmetic composition, and/or a feel improver for the hairstyling product on use.

The surfactant (B-2) may be any of those commonly used in hair care cosmetic compositions, including cationic surfactants, anionic surfactants, amphoteric surfactants, and nonionic surfactants. Examples of these surfactants are the same as those recited above. With the view of improving the glide of the impregnated sheet-like hair care product hairstyling product 13 on hair to facilitate hair treatment by finger combing and to apply the liquid cosmetic composition to hair easily, it is preferred to use (B-2-1) a cationic surfactant. With a view to improving hair setting performance, it is preferred to use an amphoteric surfactant or a nonionic surfactant. With a view to easily applying the liquid cosmetic composition impregnating the substrate sheet 12 to hair and improving hair setting performance, it is preferred to use a combination of a cationic surfactant and an amphoteric surfactant or nonionic surfactant.

The content of the surfactant in the liquid cosmetic composition is preferably 0.1 mass % or more, more preferably 0.2 mass % or more, even more preferably 0.3 mass %, and preferably 5 mass % or less, more preferably 4 mass % or less, even more preferably 3 mass % or less, even more preferably 2 mass % or less. For example, the surfactant content in the liquid cosmetic composition is preferably 0.1 mass % to 5 mass %, more preferably 0.2 mass % to 4 mass %, even more preferably 0.3 to 3 mass %.

The alcohol as ingredient (B-1) may be chosen from those usable in the liquid cosmetic composition of the first embodiment. Preferred of them are ethanol, propanol, isopropyl alcohol, 1,3-butylene glycol, dipropylene glycol, and glycerol. In order to ensure solution or dispersion stability of the liquid cosmetic composition, water and ethanol are preferred. In order to reduce the sticky feel without impairing hairstyling performance, dipropylene glycol and glycerol are preferred.

The content of the alcohol in the liquid cosmetic composition is preferably 1 mass % or more, more preferably 5 mass % or more, even more preferably 10 mass % or more, and preferably 45 mass % or less, more preferably 35 mass % or less, even more preferably 30 mass % or less. For example, the alcohol content in the liquid cosmetic composition is preferably 1 mass % to 45 mass %, more preferably 5 mass % to 35 mass %, even more preferably 10 mass % to 30 mass %.

In addition to the alcohol (B-1), the surfactant (B-2), and water (B-3), the liquid cosmetic composition may further contain the above described silicone as ingredient (B-4) so as to reduce the stickiness of the film forming resin per se and the scratchiness of the hairstyling product felt during use due to the incorporated film forming resin and to impart smoothness and silkiness to hair. It is particularly preferred to use (B-4-1) an amino-modified silicone. The ratio of the amino-modified silicone content (g) to the film forming resin content (g), the amino-modified silicone content (g)/the film forming resin content (g), is preferably 0.01 or higher, more preferably 0.02 or higher, even more preferably 0.045 or higher, and preferably 14 or lower, more preferably 5 or lower, even more preferably 3 or lower, still even more preferably 1.5 or lower. Examples of the amino-modified silicone include XF42-B8922 and XF42-C0330 (both from Momentive Performance Materials Japan); SF8451C, SF8452C, SF857C, and SM8704C (all from Dow Corning Toray); KF-867 (from Shin-Etsu Chemical); and a polysiloxane-amino-modified silicone mixture (e.g., KF-1046 from Shin-Etsu Chemical).

If desired, the liquid cosmetic composition may contain ingredients for enhancing various performance properties of the sheet-like hairstyling product in addition to the alcohol, surfactant, and water described above. Such ingredients include (B-4) a silicone other than the amino-modified silicone (B-4-1) to render hair easy to comb and provide increased comfort of use. Examples of such a silicone are polysiloxanes, modified silicones (e.g., fluorine-, alcohol-, polyether-, epoxy-, or alkyl-modified silicones), and cyclic polysiloxanes. These silicones may be used individually or in combination of two or more thereof. Inter alia, one or more of polysiloxanes and polyether-modified silicones are preferred. Commercially available silicone products may be used. Examples of commercially available silicones include polysiloxanes, such as SH200 Fluid 1,000,000CS, BY11-026, and FZ-2231 (all from Dow Corning Toray Co., Ltd.) and TSF-451-100MA (from Momentive Performance Materials Japan), and polyether-modified silicones, such as TSF4440 (from Momentive Performance Materials Japan), KF-6005 and KF-6012 (both from Shin-Etsu Chemical), and SS-2910 (from Dow Corning Toray).

The content of the silicone other than the amino-modified silicone in the liquid cosmetic composition is preferably 0.1 mass % or more, more preferably 0.2 mass % or more, even more preferably 0.3 mass % or more, and preferably 5 mass % or less, more preferably 4 mass % or less, even more preferably 3 mass % or less. For example, the content of the silicone other than the amino-modified silicone in the liquid cosmetic composition is preferably 0.1 mass % to 5 mass %, more preferably 0.2 mass % to 4 mass %, even more preferably 0.3 mass % to 3 mass %.

The liquid cosmetic composition may further contain a cooling agent imparting a cooling sensation, such as menthol, a warming agent, a powder imparting smoothness and silkiness to hair, a deodorant, an antiseptic, a fragrance, a chelating agent, and so on.

When the liquid cosmetic composition is infiltrated into the substrate sheet in an amount sufficient to be delivered to hair, it can drip off and spatter on the face or clothes or otherwise cause inconveniences of use. If a hair setting polymer capable of forming a firm coating film or with tackiness is incorporated into the liquid cosmetic composition in high concentrations with intent to impart hairstyling performance while preventing the liquid cosmetic composition from dripping down, the polymer would be transferred not only to the hair but also the hand when applied, which makes such problems prominent as an unpleasant feeling of having the sticky substance on the hand or an unpleasant sticky feel of the hand. Then, in the present embodiment, the amount of the liquid cosmetic composition is preferably 1 g or more per sheet (substrate sheet 12). With a view toward spreading the liquid cosmetic composition all over the hair, in particular, it is preferably 6 g or more, more preferably 7 g or more, even more preferably 8 g or more, per sheet. With the object of preventing the liquid cosmetic composition from excessively wetting the hair and from spattering onto the face or clothes, the amount of the liquid cosmetic composition is 50 g or less, preferably 30 g or less, more preferably 25 g or less, even more preferably 20 g or less, still even more preferably 15 g or less, per sheet. For example, the amount of the liquid cosmetic composition is preferably 1 g to 50 g, more preferably 6 g to 30 g, even more preferably 7 g to 25 g, still even more preferably 7 g to 20 g, yet even more preferably 8 g to 15 g, per sheet. With that amount of the infiltrated liquid cosmetic composition, a sufficient amount of the liquid cosmetic composition is delivered to the hair, and the sheet-like hairstyling product is convenient to use, causing little dripping off. The above recited amount of the liquid cosmetic composition is larger than that generally used by conventional sheet-like skin-care products. This is because, for one thing, the sheet-like hairstyling product of the present embodiment is designed to apply a sufficient amount of the liquid cosmetic composition to hair to exhibit high hair setting performance and, for another, it is designed to infiltrate a sufficient amount of the liquid cosmetic composition into hair thereby to make hair manageable while controlling unruly strands of hair.

The thus constituted sheet-like hairstyling product of the present embodiment is useful to fix hair after doing sports on the go or commuting; to combat dry hair in the winter or frizzy and unruly hair in humidity weather; and to make hair manageable while controlling unruly hair strands.

In the third embodiment, the liquid cosmetic composition (B) contains (B-1-1) ethanol, (B-3) water, and (B-6) a polysaccharide. The concentration of ingredient (B-1-1) in the liquid cosmetic composition is preferably 10 mass % to 45 mass %. The concentration of ingredient (B-6) in the liquid cosmetic composition is preferably 0.01 mass % to 0.4 mass %.

The hair care product of the third embodiment offers advantages of alleviated irritation to the eyes and nose during cleaning operation, a smooth glide on hair during cleaning operation, and excellent smoothness in finger combing after cleaning, a highly clean feel of scalp and hair after cleaning and capability to add fluffy light finish to hairstyle after cleaning.

A dry shampoo sheet has a large surface area, from which the impregnating liquid preparation vaporizes, and is used near the user's eyes and nose. When a conventional dry shampoo sheet (e.g., Patent Literatures 1 or 2) incorporates into the impregnating liquid preparation a sufficient amount of ethanol for removing dirt from the scalp and hair, cases have been sometimes met with in which ethanol smells too strong or strongly irritates the eyes during the use of the sheet-like dry shampoo.

A conventional dry shampoo sheet is likely to not only wipe sebum off the scalp but also strip the hair of its natural oils, resulting in problems, such as a creaky or squeaky feel of hair, a reduced glide of the shampoo sheet on hair, and hair tangles. Additionally, the scratchiness between the hair and the sheet or among hairs can make the hair messy, so that it has been very difficult to accomplish hair fixing or styling while sufficiently cleaning the hair and scalp.

Fluffy and light hairstyles are recently popular, but a conventional dry shampoo sheet, while capable of removing dirt from the scalp and hair, has difficulty in creating a fluffy and light hairstyle by making hair strands to rise from their roots.

The third embodiment aims at the provision of a sheet-like hair care product that hardly irritates the eyes and nose, has a smooth glide on hair strands, provides ease in running fingers through hair during cleaning operation, and, after use, gives a user a highly clean feel of scalp and hair and provides a fluffy and light hairstyle in a dry state. The sheet-like hair care product of the present embodiment composed of the specific substrate sheet impregnated with the above described liquid cosmetic composition has an excellent glide on hair and allows fingers to run through the hair during hair and scalp cleaning operation. The sheet-like hair product of the present embodiment gives a user a highly clean feel of scalp and hair after the cleaning operation despite of its low irritation to the eyes and nose during the cleaning operation and enables a user to do a fluffy and light hairstyle in a dry state.

Containing ingredient (B-1-1), the sheet-like hair care product of the present embodiment is capable of removing dirt from hair and scalp. Although the sheet-like hair care product impregnated with the liquid cosmetic composition has a large surface area because of its sheet form, from which the volatile ingredient (B-1-1) is allowed to vaporize, the presence of ingredient (B-6) alleviates the irritation to the eyes and nose even when the impregnated sheet is used near the user's nose and eyes. The sheet-like hair care product containing ingredient (B-6) exhibits improved glide on hair strands being cleaned and allows fingers to run easily through the hair being cleaned. That is, the sheet-like hair care product of the present embodiment achieves hair and scalp cleaning without making a user feel friction between the sheet and the hair being cleaned or feel the hair being cleaned creaky when the user glides their fingers through the hair, and imparts smoothness and slipperiness to the hair when fingers are run through during cleaning operation. Since the liquid cosmetic composition is applied to hair while removing dirt from the hair, ingredient (B-6) is spread on the hairs thinly and uniformly. If ingredient (B-6) remains on the surface of hairs, it does not cause a feeling of residue that might ruin the clean feeling of the scalp and hair, and a fluffy hairstyle can be done after drying with a pleasant touch on the treated hair. Hydrogen bonds of hair are broken in the presence of ingredient (B-3), and because ingredient (B-6) is given to the hair while the hair is in that state, an improved fluffy feel can be felt after drying.

Naturally-occurring polysaccharides, naturally-derived polysaccharides, and modified products thereof are used as the polysaccharide (B-6) with the object of buffering the nose and eyes from any irritant ingredient, especially ethanol, vaporizing from the surface of the substrate sheet during use, improving the glide between the hair and the impregnated substrate sheet, reducing the creaky feel of hair when fingers are run therethrough during use, and, after use, enabling a user to achieve a fluffy hairstyle and imparting a pleasant touch to the hair. Specifically, the polysaccharide as ingredient (B-6) is preferably selected from those composed of glucose, galactose, mannose, or glucuronic acid as a repeating unit.

The polysaccharides may be used either individually or in combination of two or more thereof. With the view of buffering the eyes and nose from the irritant ingredient, especially ethanol, vaporizing from the sheet surface, improving the glide on the strands of hair being wiped clean, and improving smoothness in running fingers through the hair being wiped clean, the content of the polysaccharide in the liquid cosmetic composition is 0.01 mass % or more, preferably 0.02 mass % or more, more preferably 0.05 mass % or more, even more preferably 0.07 mass % or more, still even more preferably 0.1 mass % or more. With a view to improving the glide on hair and the smoothness in running fingers through the hair during use without impairing the clean sensation after use and imparting a pleasant touch to the hair after drying, the content of the polysaccharide in the liquid cosmetic composition is 0.4 mass % or less, preferably 0.35 mass % or less, more preferably 0.3 mass % or less, even more preferably 0.25 mass % or less, still even more preferably 0.15 mass % or less. Specifically, the polysaccharide content in the liquid cosmetic composition is 0.01 mass % to 0.4 mass %, preferably 0.01 mass % to 0.35 mass %, more preferably 0.02 mass % to 0.3 mass %. When the liquid cosmetic composition contains the above recited amount of the polysaccharide, the liquid cosmetic composition acquires a viscosity enough to sufficiently impregnate the substrate sheet and to avoid dripping.

The polysaccharides as ingredient (B-6) are classified according to chemical structure into cationic polysaccharides, anionic polysaccharides, and nonionic polysaccharides. Cationic polysaccharides and nonionic polysaccharides are preferred for the improvement on the glide of the sheet on hair during use. Cationic polysaccharides and nonionic polysaccharides are also preferred for the prevention of creating a creaky feel of hair felt when fingers are run therethrough during cleaning operation. Anionic polysaccharides are preferred in terms of better clean sensation during use. Cationic polysaccharides are preferred with the object of imparting smoothness in finger combing after drying. Cationic polysaccharides are also preferred in terms of adding body and bounce to hair. Cationic polysaccharides and nonionic polysaccharides are preferred for imparting stylability into a fluffy hairstyle after drying.

A cationic polysaccharide is generally incorporated into liquid shampoos in order that it is combined with an anionic surfactant (the main ingredient of the shampoo) to form a complex when the shampoo is rinsed off thereby to prevent hair from creaking during rinsing and make hair smooth and silky. In the sheet-like hair care product 13 of the invention, as long as a cationic polysaccharide is used in the hereinafter described range and is not rinsed off after use, it is able to be applied to hair thinly and uniformly to protect the hair from getting creaky and allow fingers to run smoothly through the hair during cleaning operation, and after drying, enables a user to do a fluffy hairstyle and adds a pleasant touch to the hair.

From the standpoint of clean sensation after use, the cationic charge density of the cationic polysaccharide is preferably 0.1 meq/g or more, more preferably 0.2 meq/g or more, even more preferably 0.5 meq/g or more. With a view to obtaining a smooth glide between the sheet and hair as well as the clean sensation after use, the cationic charge density of the cationic polysaccharide is 3.0 meq/g or less, more preferably 2.5 meq/g or more, even more preferably 2.0 meq/g, still even more preferably 1.7 meq/g or more. As used herein, the terminology "cationic charge density" refers to the milligram equivalents (meq/g) of cationic charges in the monomer unit that constitutes a polymer. Examples of the cationic polysaccharide include cationic guar gum, cationic cellulose, cationic starch, cationic locust bean gum, cationic tara gum, cationic fenugreek gum, and their derivatives.

Specific examples of the cationic guar gum include Jaguar C-13S, Jaguar C-14S, Jaguar EXCEL C-17, and Jaguar C-500 (all from Rhodia); Catinal CG-100 (from Toho Chemical Industry); and Rhaball Gum CG-8M and Rhaball Gum CG-M7L (both from DSP Gokyo Food & Chemical). Examples of the cationic cellulose include Poise C-150L, Poise C-80M, ad Poise C-60H (all from Kao), and Catinal LC-100 and Catinal HC-200 (both from Toho Chemical Industry). Examples of the cationic starch include Sensomer CL-50 from Lubrizol. Examples of the cationic locust bean gum include Catinal CLB-100 (from Toho Chemical Industry). Examples of the cationic tara gum include Catinal CTR-100 (from Toho Chemical Industry). Examples of the cationic fenugreek gum include Catinal CF-100 (from Toho Chemical Industry).

Of the cationic polysaccharides, cationic guar gum is preferred in terms of imparting moistness to hair after drying, and cationic cellulose is preferred in terms of imparting a silky feeling to hair after drying.

The nonionic polysaccharides include water soluble natural polysaccharides, such as starch, guar gum, locust bean gum, and glucomannan, and water soluble hydroxylakylated polysaccharides obtained by causing an alkylene oxide to react with cellulose, starch, guar gum, locust bean gum, and so on. Examples of the nonionic polysaccharides are HEC Daicel SE850 from Daicel Corp., HPC—H from Nippon Soda Co., Ltd., and Structure Cell 12000M from Akzo Nobel.

The anionic polysaccharides include naturally occurring carboxyl-containing polysaccharides, such as xanthan gum and hydroxypropylxanthan gum, and sulfate group-containing polysaccharides, such as carrageenan.

The weight average molecular weight of the polysaccharide as ingredient (B-6) is preferably 50,000 or more, more preferably 100,000 or more, even more preferably 250,000 or more, still even more preferably 500,000 or more, yet still even more preferably 1,000,000 or more, with a view to obtaining both the clean feeling after use and the silky feeling of hair after drying; and preferably 2,000,000 or less, more preferably 1,800,000 or less, even more preferably 1,700,000 or less, with a view to obtain an improved glide on hair. The weight average molecular weight as referred to herein is a polystyrene equivalent weight average molecular weight determined by gel permeation chromatography.

Ethanol is used as ingredient (B-1-1) to remove dirt from hair and scalp. The ethanol content in the liquid cosmetic composition is 10 mass % or more and 45 mass % or less, preferably 35 mass % or less, even more preferably 30 mass % or less. For example, the ethanol content in the liquid cosmetic composition is 10 mass % to 45 mass %, preferably 10 mass % to 35 mass %, more preferably 10 mass % to 30 mass %.

The liquid cosmetic composition for use in the present embodiment may further contain (B-2-4) a nonionic surfactant in addition to the polysaccharide (B-6), ethanol (B-1-1), and water (B-3) to increase the ability to remove sebum (hereinafter referred to as sebum cleansing ability) and improving the hair texture or touch after use and after drying.

Examples of the nonionic surfactant as ingredient (B-2-4) include polyoxyalkylene alkyl ethers, polyoxyalkylene alkenyl ethers, higher fatty acid sucrose esters, polyglycerol fatty acid esters, higher fatty acid mono- or diethanolamides, polyoxyethylene hydrogenated castor oil, polyoxyethylene sorbitan fatty acid esters, polyoxyethylene sorbitol fatty acid esters, and alkyl saccharide surfactants. These surfactants can be used either individually or in combination of two or more thereof. Preferred of them are polyoxyethylene alkyl ethers and polyoxyethylene alkenyl ethers for their sebum cleansing ability. The nonionic surfactant content in the liquid cosmetic composition is 0.01 mass % or more, preferably 0.02 mass % or more, even more preferably 0.05 mass % or more, in terms of sebum cleansing ability; and 0.5 mass % or less, preferably 0.2 mass % or less, more preferably 0.1 mass % or less, in terms of obtaining both the sebum cleansing ability and a good texture of the treated hair.

In addition to the polysaccharide (B-6), ethanol (B-1-1), and water (B-3), the liquid cosmetic composition for use in the present embodiment may further contain (B-2-2) an anionic surfactant to further increase the sebum cleansing ability. The content of the anionic surfactant in the liquid cosmetic composition is 0.1 mass % or less, preferably 0.05 mass % or less, more preferably 0.01 mass % or less, so as to secure cleansing ability without causing foaming during use of the liquid cosmetic composition-impregnated substrate sheet 12 and without causing a feeling of any residue on the hair. While there is no particular lower limit of the anionic surfactant content, the lower limit is preferably, for example, 0.00001 mass %, more preferably zero.

Examples of useful anionic surfactants include alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, α-sulfo fatty acid salts, N-acylamino acid surfactants, phosphoric mono- or diester surfactants, and sulfosuccinic esters.

The liquid cosmetic composition used in the present embodiment may contain a cooling agent imparting a cooling sensation to sculp, such as menthol. The lower limit of the cooling agent content in the liquid cosmetic composition is 0.01 mass %, preferably 0.05 mass %, more preferably 0.1 mass %. The upper limit of the cooling agent content in the liquid cosmetic composition is 1.0 mass %, preferably 0.5 mass %.

The liquid cosmetic composition for use in the invention may further contain a powder imparting smoothness and silkiness to hair, a deodorant, an antiseptic, a fragrance, a chelating agent, a warming agent, and so forth.

The viscosity of the thus designed liquid cosmetic composition is preferably 5 mPa·s or more, more preferably 10 mPa·s or more, at 30° C. with the view of improving the glide between the sheet and hair and ease of running fingers through hair during cleaning operation. The upper limit of the viscosity the thus designed liquid cosmetic composition is preferably 5,000 mPa·s, more preferably 2,000 mPa·s, even more preferably 1000 mPa·s to leave no excessive sticky feeling on the user's hand after using. Specifically, the viscosity of the thus designed liquid cosmetic composition is preferably 5 mPa·s to 5,000 mPa·s, more preferably 10 mPa·s to 1,000 mPa·s. The viscosity of the liquid cosmetic composition at 30° C. is measured with a Brookfield viscometer. The measuring conditions are selected as appropriate to the viscosity of the liquid. As far as the viscosity of the liquid cosmetic composition used in the invention is concerned, measurement is usually taken using a rotor No. M2 up to viscosities of 1,000 mPa·s and a rotor No. M3 for viscosities above 1,000 mPa·s. The number of rotation of the rotor is 60 rpm up to viscosities of 500 mPa·s, 30 rpm between 500 mPa·s and 4,000 mPa·s, and 12 rpm for viscosities above 4,000 mPa·s.

The thus constituted hair care product 10 of the present embodiment is useful to handle perspiration or to fix hair after doing sports on the go or commuting; to remove cigarette or broiled meat odor from hair; to combat hay fever in the pollen season; to combat dry hair in the winter or frizzy and unruly hair in humidity weather; to substitute for hair washing in situations in which ample water is not available, such as in hospital, in a nursing home, during outdoor activities like climbing and camping, or a water outage; and to make hair manageable while controlling unruly strands of hair in such water shortage situations.

In the fourth embodiment, the liquid cosmetic composition (B) contains ingredients (B-2-3), (B-3), (B-4-1), and (B-8) described below. The concentration of ingredient (B-2-3) in the liquid cosmetic composition is 0.1 mass % to 2 mass %.

(B-4-1) Organopolysiloxane represented by general formula (1):

[Chem. 1]

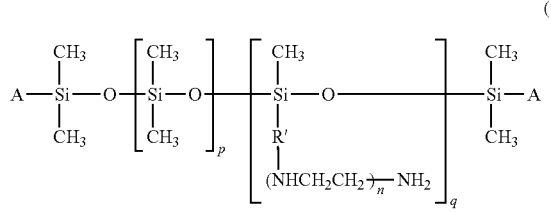

wherein A represents —R, —R—(NHCH$_2$CH$_2$)$_n$NH$_2$—, —OR, or hydroxyl; R represents an optionally substituted monovalent hydrocarbon group having 1 to 20 carbon atoms; R' represents a divalent hydrocarbon group having 1 to 8 carbon atoms; n represents an integer of 0 to 3; p and q each represent a number that satisfies the relationship: 50≤(p+q+2)≤20,000, wherein (p+q+2) is a number-average total number of silicon atoms; and the amino equivalent is 500 to 100,000 g/mol.

(B-8) Fragrance
(B-2-3) Polyoxyalkylene-added nonionic surfactant
(B-3) Water

The fourth embodiment offers the following advantages: (1) fingers easily run through hair in wiping the hair with the sheet-like hair care product, (2) wiping with the sheet gives a very clean and fresh sensation to the scalp, (3) wiping with the sheet renders hair manageable into a natural hairstyle with a soft touch, and (4) the sheet-like hair care product gives a pleasant smell to the hair after use while the smell when the sheet is spread out is not too strong.

When hair is cleaned using a conventional dry shampoo sheet impregnated with a hair care composition containing ethanol, because ethanol strips away a substance that imparts slipperiness between hair strands, hair becomes less smooth to run fingers through, and consequently, the hair to which the hair care composition has been applied is not given softness, and the use of the dry shampoo sheet is less-than-comfortable.

Because the dry shampoo sheet of Patent Literature 1 is primarily intended to remove dirt from hair and/or scalp, it does not adequately meet the consumers' need of leaving a conditioning ingredient on the surface of hair strands to impart a conditioning effect or leaving a hairstyling ingredient to fix the hair. It is a generally followed practice to add a fragrance to a hair care product to make hair smell good after removal of dirt from hair and/or scalp, i.e., after cleaning. However, if the liquid preparations of the dry shampoo sheets of Patent Literatures 1 and 2 are combined with a sufficient amount of a fragrance to add a good smell to hair after use, the smell of the dry shampoo sheet when spread out and used is too strong because the fragrance easily volatilizes from the spread out sheet. Therefore, the dry shampoo sheet is far from suitable for use close to the face.

The fourth embodiment is designed to provide a sheet-like hair care product that allows for easy and smooth running of fingers in wiping hair therewith, gives a very clean and fresh sensation to the scalp after wiping hair therewith, makes hair manageable into a natural hairstyle with a soft touch, and adds a pleasant smell to the hair after use while the smell emitted from the product when spread out is not too strong.

In an attempt to increase the smoothness in running fingers through hair in treating hair with the sheet-like hair care product as well as to make the treated hair feel soft after drying, the inventors have tried adding an amino-modified silicone. It has been revealed as a result that a fragrance vaporizes rapidly, resulting in too strong a smell or a failure to add a pleasant scent to hair sufficiently. To overcome the problem, they have conducted extensive studies and found that the liquid cosmetic composition to be infiltrated into the substrate sheet exhibits improved storage stability with time by using a fragrance in combination with a specific silicone and a specific nonionic surfactant even when the specific silicone is combined with a fragrance. They have also found that a sheet-like hair care product prepared by impregnating a substrate sheet with the liquid cosmetic composition containing a fragrance, the specific silicone, and the specific nonionic surfactant in a specific compounding ratio and thereby having improved storage stability exhibits a high hair conditioning effect and gives off a moderate smell for an extended period of time.

The sheet-like hair care product of the present embodiment allows fingers to easily run through hair in wiping hair therewith, makes hair feel soft after wiping hair therewith, gives off a moderate scent of a fragrance when spread out, which scent lasts long, exhibits a high hair conditioning effect, and makes the hair manageable into a natural hairstyle after wiping hair therewith.

The organopolysiloxane (B-4-1) of the liquid cosmetic composition for use in the present embodiment is used to improve the slide of fingers through hair in cleaning hair with the sheet-like hair care product of the present embodiment and to make hair feel soft after cleaning the hair with the sheet-like hair care product of the present embodiment and drying. The organopolysiloxane (B-4-1) is commonly termed an amino-modified silicone and will hereinafter be also called an amino-modified silicone.

To use the compound of general formula (1) as an amino-modified silicone brings about a further improved glide of fingers through air in wiping hair with the sheet-like hair care product of the invention and makes hair feel much softer after wiping the hair with the sheet-like hair care product of the invention.

In general formula (1) representing the amino-modified silicone, the monovalent group as A is preferably —R or a hydroxyl group for ready availability of the compound. When the monovalent group A is R or contains R, R is a hydrocarbon group having at least one carbon atom and 20 or fewer, preferably 12 or fewer, more preferably 8 or fewer, even more preferably 4 or fewer, carbon atoms. In general formula (1), a plurality of A's may be the same or different.

In formula (1), the divalent hydrocarbon group as R' has 1 or greater, preferably 2 or greater, more preferably 3 or greater, carbon atoms, and 8 or fewer, preferably 7 or fewer, more preferably 6 or fewer, even more preferably 5 or fewer, carbon atoms. n is 0 or greater, preferably 1 or greater, and 3 or fewer, preferably 2 or fewer.

The molecular weight of the amino-modified silicone represented by formula (1) is such that the total number of silicon atoms (p+q+2) is in the range of from 50 to 20,000, preferably 100 or greater, more preferably 300 or greater, even more preferably 500 or greater, still even more preferably 800 or greater, yet even more preferably 1000 or greater, and preferably 10,000 or smaller, more preferably 5000 or smaller, even more preferably 3000 or smaller, still even more preferably 2000 or smaller.

The amino equivalent of the amino-modified silicone of formula (1) is preferably 500 g/mol or more, 1000 g/mol or more, more preferably 2000 g/mol or more, even more preferably 4000 g/mol or more, still even more preferably 10,000 g/mol or more, and is preferably 100,000 g/mol or less, 80,000 g/mol or less, more preferably 50,000 g/mol or less, even more preferably 20,000 g/mol or less.

The amino-modified silicone of formula (1) may be incorporated in the form of emulsion. The amino-modified silicone emulsion is prepared mechanically (by high-shear mixing the amino-modified silicone with water) and/or chemically (emulsifying the amino-modified silicone in water using an emulsifying agent) or by emulsion polymerization. In carrying out chemical emulsification, various surfactants may be used as an emulsifying agent.

The amino-modified silicones of formula (1) may be used either individually or in combination of two or more thereof. In order to secure a smooth glide of the sheet-like hair care product on hair strands, the amino-modified silicone content nn in the liquid cosmetic composition is 0.01 mass % or more, preferably 0.02 mass % or more, more preferably 0.05 mass % or more, even more preferably 0.07 mass % or more, still even more preferably 0.1 mass % or more, and is 1 mass % or less, preferably 0.5 mass % or less, more preferably 0.2 mass % or less, with a view to minimizing sticky feel of hair after drying. Specifically, the content $n_A$ in the liquid cosmetic composition is preferably 0.01 mass % to 1 mass %, more preferably 0.01 mass % to 0.5 mass %, even more preferably 0.02 mass % to 0.5 mass %. When the amino-modified silicone content in the liquid cosmetic composition is in the range recited, the sheet-like hair care product 13 has an improved glide in wiping hair therewith by fingers and gives a soft touch to the hair after the wiping.

The fragrance as ingredient (B-8) is used to provide a user with a pleasurable fragrance during and after the use of the sheet-like hair care product of the present embodiment. Fragrances conventionally used in cosmetics or medical products are useful as ingredient (B-8). Specifically, those described, e.g., in Arctanger, Stephan, Perfume and Flavor Chemicals; Akaboshi, Ryoichi, The Chemical Society of Japan (ed.), Koryo no Kagaku, Sangyo Kagaku Series; Endo, Gen-ichi, Gosei Koryo: Kagaku to Shohin Chisiki, The Chemical Daily Co., Ltd.; and Nakajima, Motoki, Koryo to Cyoko no Jissai Chisiki, Sangyo Tosho Publishing Co., Ltd. These fragrances may be used either individually or in the form of a composition of two or more thereof.

In view of application to hair and with the object of making a user feel a moderate smell during and for a while after application, it is preferred to use a combination of (a) a fragrance material having a vapor pressure of 0.01 mmHg or higher and lower than 5.0 mmHg at 25° C. and (b) a fragrance material having a vapor pressure of 0.0001 mmHg or higher and lower than 0.01 mmHg. The fragrance material (a) to fragrance material (b) mass ratio is preferably 1/100 to 100/1, more preferably 1/10 to 10/1, in terms of balance of fragrance. The total content of the fragrance materials (a) and (b) in the liquid cosmetic composition is preferably at least 0.0001 mass %, more preferably 0.01 mass % or more, with intent to have the sheet-like hair care product giving off a pleasant smell when spread out and to have the treated hair smelling good. The upper limit of the total content of the fragrance materials (a) and (b) in the liquid cosmetic composition is preferably 0.5 mass %, more preferably 0.2 mass %, even more preferably 0.1 mass %, so as to avoid emission of too strong a smell when the sheet-like hair care product is spread out. Specifically, the total content of the total content of the fragrance materials (a) and (b) in the liquid cosmetic composition is 0.0001 mass % to 0.5 mass %, preferably 0.01 mass % to 0.2 mass %, more preferably 0.01 mass % to 0.1 mass %.

As a result of the inventors' study, it turned out that, when a liquid cosmetic composition prepared by mixing ingredient (B-4-1) and ingredient (B-8) with water is infiltrated into a substrate sheet to make a sheet-like hair care product containing the fragrance as ingredient (B-8) in an amount sufficient to add a pleasant smell to the hair after use, the resulting product allows the fragrance to volatilize easily when the sheet-like product is spread out on use, thereby emitting too strong a smell. On the other hand, when the liquid cosmetic composition is formulated to give off a moderate smell when the sheet is spread out on use, addition of the smell to hair to be felt after use is found insufficient. To settle this problem, it has been ascertained that, when a polyoxyalkylene-added nonionic surfactant (B-2-3) is added to the liquid cosmetic composition containing ingredient (B-4-1), ingredient (B-8), and water to increase the storage stability of the composition, the sheet impregnated with the resulting liquid cosmetic composition is very effectively prevented from allowing the fragrance as ingredient (B-8) to volatilize at once from the liquid cosmetic composition. The above described formulation thus allows for emission of a moderate pleasant smell of the fragrance during and after use.

Examples of the polyoxyalkylene-added nonionic surfactant (B-2-3) include polyoxyalkylene alkyl ethers, polyoxyalkylene alkenyl ethers, polyoxyalkylene sorbitan fatty acid esters, polyoxyalkylene sorbitol fatty acid esters, polyoxyalkylene fatty acid esters, polyoxyalkylene castor oils, polyoxyalkylene hydrogenated castor oils, and polyoxyalkylene alkylamines. These surfactants may be used individually or in combination of two or more thereof. It is preferred to use, as ingredient (B-2-3), at least one of ingredient (B-2-3-1)

and ingredient (B-2-3-2) described below with the view of imparting further improved storage stability to the liquid cosmetic composition.

(B-2-3-1) At least one member selected from polyoxyalkylene monoalkyl ethers and polyoxyalkylene monoalkenyl ethers.

(B-2-3-2) At least one member selected from polyoxyalkylene castor oils and polyoxyalkylene hydrogenated castor oils.

With the intension of causing a moderate pleasant smell to be emitted when the sheet-like product is spread out in a broad range of temperature of use, e.g., 0° to 35° C., it is preferred for ingredient (B-2-3) to contain both ingredient (B-2-3-1) and ingredient (B-2-3-2).

The polyoxyalkylene moiety of the surfactant (B-2-3-1) is at least one of polyoxyethylene, polyoxypropylene, and polyoxybutylene, preferably at least one of polyoxyethylene and polyoxypropylene, more preferably polyoxyethylene. The degree of polymerization of the polyoxyalkylene is 3 or more, preferably 5 or more, more preferably 10 or more, even more preferably 20 or more, still even more preferably 30 or more, in view of the storage stability of the composition and smell emission characteristics; and 70 or less, preferably 60 or less, more preferably 50 or less, even more preferably 40 or less, in view of the storage stability of the composition.

The alkyl and alkenyl moieties may be straight or branched. The number of carbon atoms of the alkyl and alkenyl moieties is 10 or greater, preferably 12 or greater, more preferably 12 or greater, even more preferably 16 or greater, from the viewpoint of the storage stability of the composition, and 30 or smaller, preferably 26 or smaller, more preferably 22 or smaller, even more preferably 20 or smaller, still even more preferably 18 or smaller, in view of the storage stability of the composition.

The polyoxyalkylene monoalkyl ether and the polyoxyalkylene monoalkenyl ether may be used individually or in combination thereof. Two or more polyoxyalkylene monoalkyl ethers may be used in combination. Two or more polyoxyalkylene monoalkenyl ethers may be used in combination.

With a view to maintain the liquid cosmetic composition stably irrespective of the variations in temperature at which the hair care products are stored, to impart a moderate smell during use, and to give off a long lasting smell, it is preferred to use a combination of a secondary alcohol alkoxylate and a primary alcohol alkoxylate.

The polyoxyalkylene moiety of the surfactant (B-2-3-2) is at least one of polyoxyethylene, polyoxypropylene, and polyoxybutylene, preferably at least one of polyoxyethylene and polyoxypropylene, more preferably polyoxyethylene. The degree of polymerization of the polyoxyalkylene is 20 or more, preferably 30 or more, more preferably 40 or more, even more preferably 50 or more, in view of the storage stability of the composition; and 100 or less, preferably 80 or less, more preferably 70 or less, in view of the storage stability of the composition. The polyoxyalkylene castor oil and the polyoxyalkylene hydrogenated castor oil may be used individually or in combination thereof. Two or more polyoxyalkylene castor oils may be used in combination. Two or more polyoxyalkylene hydrogenated castor oils may be used in combination.

The content $n_{Ca}$ of ingredient (B-2-3) in the liquid cosmetic composition is preferably 0.05 mass % or more, preferably 0.1 mass % or more, even more preferably 0.5 mass % or more, in view of the storage stability of the liquid cosmetic composition and smell emission characteristics; and preferably 2 mass % or less, more preferably 1.5 mass % or less, even more preferably 1 mass % or less, in view of the storage stability of the liquid cosmetic composition and the touch of treated hair after drying. Specifically, the content $n_{Ca}$ of ingredient (B-2-3) in the liquid cosmetic composition is preferably 0.05 mass % to 2 mass %, more preferably 0.1 mass % to 1.5 mass %, even more preferably 0.5 mass % to 1 mass %. When the content of ingredient (B-2-3) of the liquid cosmetic composition is in the range recited above, the liquid cosmetic composition exhibits improved storage stability.

Water as ingredient (B-3) makes up the rest of the liquid cosmetic composition. The water content in the liquid cosmetic composition is preferably 50 mass % or more, more preferably 60 mass % or more, even more preferably 65 mass %, still even more preferably 70 mass % or more, and preferably 95 mass % or less, more preferably 90 mass % or less, even more preferably 85 mass % or less, still even more preferably 80 mass % or less.

In order to ensure the increased storage stability of the liquid cosmetic composition for use in the invention, to further prolong the effect in imparting a pleasant smell of ingredient (B-8) to hair after use of the sheet-like hair care product without giving off the smell too strongly on spreading out the sheet-like product, and to further increase the stability of ingredient (B-4-1) in the liquid cosmetic composition, the inventors have found it important to properly adjust the contents of ingredients (B-4-1), (B-8), and (B-2-3) in the liquid cosmetic composition. That is, considering the ratio of the sum of the content $n_A$ (mass %) of ingredient (B-4-1) and the content ns8 (mass %) of ingredient (B-8) to the content $n_{Ca}$ (mass %) of ingredient (B-2-3), $[n_A+n_{B8}]/n_{Ca}$, it is advantageous to decide the contents of these three ingredients so that the ratio may be 0.05 or higher, preferably 0.075 or higher, more preferably 0.1 or higher and 0.65 or lower, preferably 0.5 or lower, more preferably 0.3 or lower. Specifically, it is advantageous to decide these contents so that $[n_A+n_{B8}]/n_{Ca}$ may be 0.05 to 0.65, preferably 0.075 to 0.5, more preferably 0.1 to 0.3.

In order to further increase the storage stability of the liquid cosmetic composition, to prolong the effect in imparting a pleasant smell of ingredient (B-8) to hair after use of the sheet-like hair care product without giving off the smell too strongly on spreading out the sheet-like product, and to further increase the stability of ingredient (B-4-1) in the liquid cosmetic composition, the value of the sum $[n_A+n_{B8}]$ is 0.01 or greater, preferably 0.1 or greater, and 1 or smaller, preferably 0.5 or smaller, provided that $[n_A+n_{B8}]/n_{Ca}$ is in the above recited range. In the case where ingredients (B-2-3-1) and (B-2-3-2) are used in combination, the ratio of the content of ingredient (B-2-3-1) to the content of ingredient (B-2-3-2), $n_{C-1}/n_{C-2}$, is preferably 0.1 or higher, more preferably 0.2 or higher, even more preferably 0.5 or higher, and preferably 10 or lower, more preferably 2 or lower, with the object of having the sheet-like hair care product emit the moderate, pleasant smell when spread out in a likely broad range of temperature of use, e.g., from 0° to 35° C.

In addition to the above discussed ingredients, the liquid cosmetic composition that can be used in the invention may contain other ingredients with the view of enhancing various performance properties of the sheet-like hair care product 13 of the invention. Such other ingredients include the above described alcohol (B-1).

Ingredient (B-1) is used to adjust the viscosity of the liquid cosmetic composition. It is also useful as a solubilizer for an ingredient incorporated in the liquid cosmetic composition. It is also useful to remove dirt using the sheet-like hair care product of the invention. Suitable alcohols include ethanol, propanol, isopropyl alcohol, 1,3-butylene glycol, dipropylene glycol, and glycerol. Ethanol is preferred for its giving a fresh feeling during use. Even when the sheet-like hair care product of the present embodiment contains ethanol, the product retains the property of emitting a moderate fragrance without making a user feel the odor of ethanol.

The lower limit of the content of ingredient (B-1) in the liquid cosmetic composition is 1 mass %, preferably 5 mass %, more preferably 10 mass %, even more preferably 15 mass %, and the upper limit is 50 mass %, preferably 40 mass %, more preferably 30 mass %, even more preferably 25 mass %. For example, the content of ingredient (B-1) in the liquid cosmetic composition is preferably 1 mass % to 50 mass %, more preferably 5 mass % to 40 mass %, even more preferably 10 mass % to 30 mass %.

The liquid cosmetic composition may further contain surfactants other than ingredient (B-2-3). Preferred as a surfactant other than ingredient (B-2-3) is the cationic surfactant as ingredient (B-2-1) with a view to reducing the friction between the liquid cosmetic composition-impregnated sheet-like hair care product and hair in wiping thereby to facilitate application of the liquid cosmetic composition to the hair. Examples of suitable cationic surfactants include alkyltrimethylammonium salts, alkoxyalkyltrimethylammonium salts, dialkyldimethylammonium salts, alkyldimethylamines and salts thereof, alkoxyalkyldimethylamines and salts thereof, alkylamidoalkyldimethylamines and salts thereof.

The content of the cationic surfactant, if used, in the liquid cosmetic composition is preferably 0.01 mass % or more, more preferably 0.05 mass % or more, even more preferably 0.1 mass % or more, and preferably 1 mass % or less, more preferably 0.5 mass % or less, even more preferably 0.3 mass or less.

The liquid cosmetic composition may further contain a warming agent, a powder imparting smoothness and silkiness to hair, a deodorant, an antiseptic, a cooling agent, a chelating agent, and so on.

The thus constituted sheet-like hair care product of the present embodiment is useful to clean or fix hair after doing sports on the go or commuting; to combat dry hair in the winter or frizzy and unruly hair in humidity weather; and to make hair manageable by controlling unruly hair strands. During and after use, the sheet-like hair care product of the present embodiment imparts the smell of the fragrance (B-8) to the user. Emission of the fragrant smell is prolonged effectively by the action of ingredient (B-2-3).

In the fifth embodiment, the liquid cosmetic composition as component (B) contains ingredients (B-2-3-1), (B-2-3-2), (B-3), (B-4-1), and (B-7) described below. The ratio of the sum of the content $n_A$ (mass %) of ingredient (B-4-1) and the content $n_{B7}$ (mass %) of ingredient (B-7) to the sum of the content $n_C$ (mass %) of ingredient (B-2-3-1) and the content nn (mass %) of ingredient (B-2-3-2), $[n_A+n_{B7}]/[n_C+n_D]$, is 0.01 or higher, preferably 0.05 or higher, more preferably 0.1 or higher, and 1 or lower, preferably 0.8 or lower, more preferably 0.6 or lower, even more preferably 0.4 or lower, still even more preferably 0.3 or lower.

(B-4-1) Organopolysiloxane represented by general formula (1).
(B-7) Cooling agent.
(B-2-3-1) At least one member selected from polyoxyalkylene monoalkyl ethers and polyoxyalkylene monoalkenyl ethers.
(B-2-3-2) At least one member selected from polyoxyalkylene castor oils and polyoxyalkylene hydrogenated castor oils.
(B-3) water The sheet-like hair care product of the fifth embodiment is excellent in cooling effect and conditioning effect and has an additional advantage of no irritating odor nor irritation to the user's eyes despite of the large surface area in the nature of its sheet form.

When hair is cleaned using a conventional dry shampoo sheet impregnated with a hair care composition containing ethanol, because ethanol strips away a substance that imparts slipperiness between hair strands, hair becomes less smooth to run fingers through, and consequently, the hair to which the hair care composition has been applied is not given softness, and the use of the dry shampoo sheet is less-than-comfortable.

Because the dry shampoo sheet of Patent Literature 1 is primarily intended to remove dirt from hair and/or scalp, it does not adequately meet the consumers' need of leaving a conditioning ingredient on the surface of hair strands to impart a conditioning effect or leaving a hairstyling ingredient to fix the hair. The dry shampoo sheet of Patent Literature 2 is unsatisfactory in fulfilling the consumers' desire to arrange their hair style. Unlike hair cosmetic preparations such as mists and sprays, sheet-like cosmetics such as dry shampoo sheets have a large surface area and are therefore liable to allow l-menthol to volatilize easily when spread out, resulting in emission of an irritating odor or strong irritation to the eyes. Therefore, the dry shampoo sheet is far from suitable for use close to the face.

The fifth embodiment is designed to provide a hair care product that allows for easy and smooth miming of fingers in wiping hair, gives a very clean and cooling sensation that lasts long to the hair and scalp.

In an attempt to improve the glide of fingers through hair in treating hair with the sheet-like hair care product as well as to make the treated hair feel soft upon drying, the inventors have tried adding an amino-modified silicone. They have found, however, that this results in an remarkable increase of the irritation of a cooling agent volatilizing from the surface of the sheet-like hair care product to the eyes and nose. To overcome this problem, they have conducted extensive studies and ascertained that the liquid cosmetic composition infiltrated into the substrate sheet exhibits improved storage stability with time by using a cooling agent in combination with a specific silicone and a specific nonionic surfactant in a specific ratio even when a cooling agent is used in combination with the specific silicone. They have also found that a sheet-like hair care product prepared by impregnating a substrate sheet with the liquid cosmetic composition containing a cooling agent, the specific silicone, and the specific nonionic surfactant in a specific compounding ratio and thereby having improved storage stability leaves a high clean and fresh sensation on the scalp and gives a high hair conditioning effect with reduced irritating odor and reduced irritation to the eyes.

The sheet-like hair care product of the present embodiment has an improved glide on hair strands in wiping hair therewith by finger combing, makes the hair feel soft after wiping therewith, and leaves a very clean and cooling sensation on the hair and scalp, which sensation lasts long. In spite of the prolonged cooling sensation attributed to the cooling agent, the possible irritating odor or irritation to the eyes caused by the cooling agent vaporized from the surface of the sheet-like hair care product are minimized. Additionally, the sheet-like hair care product of the present embodiment exhibits a high hair conditioning effect and enables a user to fix their hair into a natural hairstyle after wiping their hair therewith.

The organopolysiloxane as ingredient (B-4-1) of the liquid cosmetic composition for use in the present embodiment may be the same as the one described with reference to the fourth embodiment. The content of the organopolysiloxane in the liquid cosmetic composition may also be the same as in the fourth embodiment.

The cooling agent as ingredient (B-7) is used to impart a cooling sensation to the user during or after the use of the sheet-like hair care product of the present embodiment thereby to increase the feeling of the hair and scalp having been cleaned or the clean feeling of the hair and scalp. The cooling agent to be used is a substance capable of being absorbed subcutaneously by a human body to give a cooling sensation and is selected from those commonly employed in cosmetics and pharmaceuticals. Examples of useful cooling agents include 1-menthol; menthol derivatives, such as menthyl acetate, menthyl lactate, 1-menthyl glycerol ether, and menthylpyrrolidonecarboxylic acid; menthol analogues, such as N-ethyl-p-menthane-carboxyamide, dl-camphor, isopulegol, cineol, borneol, thymol, and their derivatives. In addition, 3-1-methoxypropanediol and menthol-containing essential oils, such as Japanese mint oil and peppermint oil are also useful. These cooling agents may be used individually or in combination of two or more thereof. Inter alia, it is preferred to use 1-menthol, methylpyrrolidone carboxylate, menthyl lactate, or N-ethyl-p-menthane-carboxyamide for their cooling effect. It is particularly preferred to use a combination of 1-menthol and at least one of the other cooling agents listed with the view of obtaining a sufficiently increased, long-lasting cooling effect and in view of the promptness of the cooling effect.

The content $n_{B7}$ of the cooling agent (B-7) in the liquid cosmetic composition is 0.01 mass % or more, preferably 0.02 mass % or more, more preferably 0.03 mass % or more, from the viewpoint of imparting a clean and fresh feeling, and 0.5 mass % or less, preferably 0.2 mass % or less, more preferably 0.1 mass % or less, from the viewpoint of minimizing the irritating odor or irritation to the eyes at the time of using the sheet-like hair care product. Specifically, the content $n_{Br}$ of the cooling agent (B-7) in the liquid cosmetic composition is preferably 0.01 mass % to 0.5 mass %, more preferably 0.01 mass % to 0.2 mass %, even more preferably 0.02 mass % to 0.2 mass %. When the content of the cooling agent in the liquid cosmetic composition falls within that range, the product imparts a moderate cooling sensation to the user.

As a result of the inventors' study, it turned out that, when a liquid cosmetic composition prepared by mixing ingredient (B-4-1) and ingredient (B-7) with water is infiltrated into a substrate sheet to make a sheet-like hair care product containing the cooling ingredient (B-7) in an amount sufficient to add a sufficient clean and fresh feeling to the hair after use, the resulting sheet-like product allows the cooling agent (B-7) to volatilize when spread out on use to cause an excessively strong irritating odor or irritation to the eyes. On the other hand, if the amount of ingredient (B-7) is reduced to control the irritating odor or the irritation to the eyes, the resulting product imparts an insufficient clean and fresh feeling during use. Then, the inventors have tried using the aforementioned ingredients (B-2-3-1) and (B-2-3-2) in addition to ingredients (B-4-1) and (B-7) and impregnating a substrate sheet with the resulting liquid cosmetic composition. It has been revealed, as a result, that the storage stability of the liquid cosmetic composition containing ingredients (B-4-1), (B-7), and water improves, and the irritating odor and irritation to the eyes ascribed to ingredient (B-7) vaporizing from the surface of the substrate sheet decrease, and the clean and fresh feeling lasts after use of the product.

Ingredient (B-2-3-1) and ingredient (B-2-3-2) for use in the present embodiment may be the same as those usable in the liquid cosmetic composition of the fourth embodiment.

The content $n_C$ of ingredient (B-2-3-1) in the liquid cosmetic composition is 0.01 mass % or more, preferably 0.05 mass % or more, more preferably 0.1 mass % or more, even more preferably 0.2 mass % or more, still even more preferably 0.4 mass % or more, in terms of storage stability of the composition, control of the irritating odor and irritation to the eyes, and a fresh feeling after use; and 1 mass % or less, preferably 0.8 mass % or less, more preferably 0.7 mass % or less, even more preferably 0.6 mass % or less, in terms of storage stability of the composition and the pleasant touch of the hair after use. Specifically, the content $n_C$ of ingredient (B-2-3-1) in the liquid cosmetic composition is preferably 0.01 mass % to 1 mass %, more preferably 0.05 mass % to 0.8 mass %, even more preferably 0.2 mass % to 0.6 mass %. When the content of ingredient (B-2-3-1) in the liquid cosmetic composition is in that range, ingredient (B-2-3-1) is capable, in cooperation with ingredient (B-2-3-2), of effectively alleviating excessive irritation caused by the cooling agent (B-7) and increasing the stability of ingredient (B-4-1) in the liquid cosmetic composition.

The content $n_D$ of ingredient (B-2-3-2) in the liquid cosmetic composition is 0.01 mass % or more, preferably 0.05 mass % or more, more preferably 0.1 mass % or more, even more preferably 0.5 mass % or more, still even more preferably 0.7 mass % or more, in terms of storage stability of the composition, control of the irritating odor and irritation to the eyes, and a fresh feeling after use; and 2 mass % or less, preferably 1.5 mass % or less, more preferably 1.0 mass % or less, even more preferably 0.8 mass % or less, in terms of storage stability of the composition and the pleasant touch of the hair after drying. Specifically, the content $n_D$ of ingredient (B-2-3-2) in the liquid cosmetic composition is preferably 0.01 mass % to 1.5 mass %, more preferably 0.1 mass % to 1.5 mass %, even more preferably 0.5 mass % to 1.0 mass %. When the content of ingredient (B-2-3-2) in the liquid cosmetic composition is in that range, ingredient (B-2-3-2) is capable, in cooperation with ingredient (B-2-3-1), of effectively alleviating excessive irritation caused by the cooling agent (B-7) and increasing the stability of ingredient (B-4-1) in the liquid cosmetic composition.

Water as ingredient (B-3) makes up the rest of the liquid cosmetic composition. The water content of the liquid cosmetic composition is preferably 50 mass % or more, more preferably 60 mass % or more, even more preferably 65 mass %, still even more preferably 70 mass % or more, and preferably 95 mass % or less, more preferably 90 mass % or less, even more preferably 85 mass % or less, still even more preferably 80 mass % or less.

In order to further increase the storage stability of the liquid cosmetic composition for use in the invention thereby to further alleviate the irritating odor and irritation to the eyes caused by the cooling agent (B-7) as well as to impart a pleasant touch to the hair after use, the inventors have found it important to properly adjust the contents of the ingredients. Specifically, considering the ratio of the sum of the content $n_A$ (mass %) of ingredient (B-4-1) and the content $n_{B7}$ (mass %) of ingredient (B-7) to the sum of the content $n_C$ (mass %) of ingredient (B-2-3-1) and the content $n_D$ (mass %) of ingredient (B2-3-2), $[n_{A}+n_{B7}]/[n_{C}+n_{D}]$, it is advantageous to decide the contents of these ingredients so that the value $[n_A+n_{B7}]/[n_C+n_D]$ may be 0.01 or higher, preferably 0.05 or higher, more preferably 0.1 or higher, and 1 or lower, preferably 0.8 or lower, more preferably 0.6 or lower, even more preferably 0.4 or lower, still even more preferably 0.3 or lower, yet even more preferably 0.2 or lower. For example, the value $[n_A+n_{B7}]/[n_C+n_D]$ is 0.01 to 1.0, preferably 0.05 to 0.6, more preferably 0.1 to 0.3.

With the object of further increasing the storage stability of the liquid cosmetic composition thereby further alleviating the excessive irritating odor and irritation to the eyes caused by the cooling agent (B-7) as well as to impart a pleasant touch to the hair after use, the value $n_C/n_D$ is 0.01 or greater, preferably 0.1 or greater, more preferably 0.3 or greater, even more preferably 0.5 or greater, still even more preferably 0.6 or greater. With the object of imparting a pleasant touch to the hair after use, the value $n_C/n_D$ is 0.95 or smaller, preferably 0.9 or smaller, more preferably 0.8 or smaller, even more preferably 0.75 or smaller.

In addition to the above discussed ingredients, the liquid cosmetic composition that can be used in the present embodiment may contain other ingredients with the view of enhancing various performance properties of the sheet-like hair care product of the present embodiment. For example, the above described alcohol (B-1) may be added.

Ingredient (B-1) is used to adjust the viscosity of the liquid cosmetic composition. It is also useful as a solubilizer for an ingredient incorporated in the liquid cosmetic composition. It is also useful to remove dirt using the sheet-like hair care product of the invention. Suitable alcohols include ethanol, propanol, isopropyl alcohol, 1,3-butylene glycol, dipropylene glycol, and glycerol.

The lower limit of the content of ingredient (B-1) in the liquid cosmetic composition is 1 mass %, preferably 5 mass %, more preferably 10 mass %, even more preferably 15 mass %, and the upper limit is 50 mass %, preferably 40 mass %, more preferably 30 mass %, even more preferably 25 mass %. For example, the content of ingredient (E) in the liquid cosmetic composition is preferably 1 mass % to 50 mass %, more preferably 5 mass % to 40 mass %, even more preferably 10 mass % to 30 mass %.

The liquid cosmetic composition may further contain surfactants other than ingredients (B-2-3-1) and (B-2-3-2). Preferred as a surfactant other than ingredients (B-2-3-1) and (B-2-3-2) is a cationic surfactant with a view to reducing the friction between the hair and the impregnated sheet-like hair care product thereby to facilitate wiping hair with the product and to facilitate application of the liquid cosmetic composition to the hair. Examples of suitable cationic surfactants include alkyltrimethylammonium salts, alkoxyalkyltrimethylammonium salts, dialkyldimethylammonium salts, alkyldimethylamines and salts thereof, alkoxyalkyldimethylamines and salts thereof, alkylamidoalkyldimethylamines and salts thereof.

The content of the cationic surfactant, if used, in the liquid cosmetic composition is preferably 0.01 mass % or more, more preferably 0.05 mass % or more, even more preferably 0.1 mass % or more, and preferably 1 mass % or less, more preferably 0.5 mass % or less, even more preferably 0.3 mass % or less.

The liquid cosmetic composition may further contain a warming agent, a powder imparting smoothness and silkiness to hair, a deodorant, an antiseptic, a fragrance, a chelating agent, and so forth.

The thus constituted sheet-like hair care product of the present embodiment is useful to clean or fix hair after doing sports on the go or commuting; to combat dry hair in the winter or frizzy and unruly hair in humidity weather; and to make hair manageable by controlling unruly hair strands. During and after use, the sheet-like hair care product of the present embodiment imparts a fresh and clean feeling or a cooling sensation to the user by the action of the cooling agent (B-7). Any irritations associated with the clean feeling and cooling sensation are controlled effectively by the action of ingredients (B-2-3-1) and (B-2-3-2).

In the sixth embodiment, the liquid cosmetic composition (B) contains ingredients (B-9), (B-10), (B-7), and (B-3) described below. The liquid cosmetic composition has a pH of 6 to 9.5 and a viscosity of 5 to 5,000 mPa·s at 30° C.

(B-9) Polyhydroxylamine represented by general formula (2) shown below and/or a salt thereof, (B-9) Polyhydroxylamine being used in an amount of 0.01 mass % to 2 mass %.

[Chem. 2]

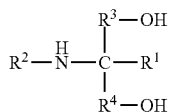

(2)

wherein $R^1$ represents a hydrogen atom, an alkyl group having 1 to 5 carbon atoms, or a hydroxyalkyl group having 1 to 5 carbon atoms; $R^2$ represents a hydrogen atom, an alkyl group having 1 to 6 carbon atoms, or a hydroxyalkyl group having 1 to 5 carbon atoms; $R^3$ and $R^4$, which may be the same or different, each represent an alkylene group having 1 to 5 carbon atoms.

(B-10) Anionic thickening polymer
(B-7) Cooling agent
(B-3) Water

The sixth embodiment is advantageous in that: a liquid cosmetic composition containing a polyhydroxylamine can be applied adequately and uniformly to both the entire scalp and the whole hair thereby to produce an excellent deodorant effect; an increased clean feeling is imparted to the scalp and hair; an improved hair conditioning effect is obtained; the fresh feeling imparted to the scalp lasts long; and a fluffy light finish is added to the hairstyle.

A liquid preparation of conventional dry shampoo sheets is primarily intended to remove dirt from hair and/or scalp. Although it is capable of removing dirt components such as sebum, it is unsatisfactory in terms of deodorant effect with no considerations given to odor components on the skin. While it makes a user feel fresh or cool immediately after wiping hair therewith, the cooling sensation does not last.

Unlike the face or body, the scalp has hair on it. Therefore, odor components generated on the scalp migrate to the hair easily and exist on both the scalp and hair. In order to obtain a sufficient deodorant effect, a polyhydroxylamine and like ingredients should be applied uniformly to the entire scalp and the whole hair in a sufficient amount. However, because the hair, unlike the face or body, is composed of dry proteins with a low water content and has an extremely large surface area, simply applying a liquid preparation containing a polyhydroxylamine to a dry shampoo sheet to wipe clean the scalp results in difficulty in sufficiently and uniformly deliver the polyhydroxylamine and the like to both the entire scalp and the whole hair, so that the resulting deodorant effect is insufficient. This is because the liquid preparation is absorbed into the inside of hair bunches or inside of individual hair strands before it reaches the entire scalp and the whole hair. Depending on the formulation of the liquid preparation, an ingredient of the deodorant composition may remain on the hair to cause discomfort, such as unwanted bunching up of hair strands or a heavy feeling of sticky residue on hair, which makes the product unsuited for use to wipe clean.

A skin-care sheet impregnated with a cosmetic composition containing tris(hydroxymethylaminomethane) is known. The cosmetic composition-impregnated skin-care sheet is described as optionally containing a thickener having an acidic group. However, if the thickener-containing skin care sheet is applied to hair, it can cause such disadvantages as bunching up of hair strands after drying or an unnatural feeling of residue on the hair after use, like a heavy, sticky feeling, unlike when it is applied to the skin. Therefore, the technique of the skin-care sheet is not necessarily effective on hair care products that are required to give a clean and fresh feeling without being washed away, such as dry shampoos, and encounters difficulty in enabling consumers to fix their hairdo with a fluffy light finish added as recently demanded.

The sixth embodiment is designed to provide a sheet-like hair care product that is capable of uniformly applying a sufficient amount of a liquid cosmetic composition containing a polyhydroxylamine and others to both the entire scalp and the whole hair thereby to produce an excellent deodorant effect; imparting an increased clean feeling to the scalp and hair, imparting an improved hair conditioning effect, affording a fresh feeling to the scalp for a prolonged time, and adding a fluffy light feeling to a hairstyle.

The inventors have found it effective to adjust the viscosity of the liquid cosmetic composition appropriately in order to achieve both prolongation of the cooling sensation created by a cooling agent and uniform application of the liquid cosmetic composition to both the scalp and hair. It has been difficult, nevertheless, to appropriately increase the viscosity of the liquid cosmetic composition by addition of various thickeners when the liquid cosmetic composition contains a polyhydroxylamine because the liquid cosmetic composition containing a polyhydroxylamine shows a very unusual thickening behavior. That is, addition of a varied amount of a thickener can result in no change in viscosity, or a very slight increase in amount of a thickener to be added can often result in an abrupt rise in viscosity. Such a thickening behavior has made it difficult to stably adjust the viscosity. Even when thickening is possible, the resulting liquid cosmetic composition can make the user's hand sticky during wiping or leave a sticky feel on the hand after wiping, impair the touch of the hair after drying, or reduce the clean feeling of the scalp. To address these problems, the inventors have tried using a specific thickener and found it effective in appropriately adjusting the viscosity. Also, they have unexpectedly found that the resulting liquid cosmetic composition infiltrated into a substrate sheet and applied to hair leaves a reduced feeling of the thickener remaining on the hair and that a cooling agent added to the liquid cosmetic composition not only improves the clean feeling but exhibits a prolonged duration of the cooling sensation obtained thereby and adds a fluffy finish to the hairstyle.

The present embodiment provides a sheet-like hair care product having a deodorant effect on the scalp and hair after wiping clean is provided. The present embodiment provides a sheet-like hair care product having a smooth glide on hair to provide smooth running of fingers through hair being treated in a hair and scalp cleaning operation. The present embodiment provides a sheet-like hair care product giving a high clean feeling of the scalp and hair after wiping therewith and, after drying, gives a fluffy finish to the hairstyle. The present embodiment provides a sheet-like hair care product that leaves a reduced feeling of a thickener residue and gives a fresh and cooling sensation to the scalp and hair during cleaning operation. After the cleaning operation, the cooling sensation lasts long.

The liquid cosmetic composition that can be used in the present embodiment contains a polyhydroxylamine and/or a salt thereof as ingredient (B-9). Although the presence of ingredient (B-9) in a liquid preparation makes it difficult to increase the viscosity of the liquid preparation, incorporating the specific ingredient (B-10) allows for adjusting the viscosity of the liquid preparation within a proper range, whereby the liquid preparation containing ingredient (B-9) can be applied uniformly to the whole hair and scalp. By the viscosity adjustment, the cooling sensation effect of ingredient (B-7) is allowed to last long. When the liquid cosmetic composition is infiltrated into a substrate sheet, and the resulting impregnated sheet is used to clean hair and scalp, ingredient (B-9) is uniformly delivered to the whole hair and scalp, whereby the dirt is removed from the hair and scalp, and the odor of the hair and scalp is eliminated. Furthermore, the liquid cosmetic composition of the present embodiment improves the glide between the sheet and the hair and the smoothness of running fingers through hair in wiping operation and adds a fluffy finish to the hair after drying. That is, ingredient (B-10) is used to uniformly deliver component (B-9) to hair and scalp so that the ingredient (B-9) may exhibit its capabilities of efficiently removing dirt from hair and scalp and efficiently eliminate the odor of hair and scalp.

The polyhydroxylamine as ingredient (B-9) is represented by general formula (2) shown supra. The polyhydroxylamine of formula (2) and/or its salt as ingredient (B-9) will hereinafter be inclusively referred to as a polyhydroxylamine compound. In general formula (2), $R^1$ is a hydrogen atom, an alkyl group having 1 to 5 carbon atoms, or a hydroxyalkyl group having 1 to 5 carbon atoms. The C1-C5 alkyl group may be straight or branched and includes methyl, ethyl, n-propyl, isopropyl, butyl (any isomer), and pentyl (any isomer). The C1-C5 hydroxyalkyl group includes hydroxymethyl, 2-hydroxyethyl, 2-hydroxypropyl, 3-hydroxypropyl, 2-hydroxybutyl, 3-hydroxybutyl, and 4-hydroxybutyl. In view of deodorizing effect and ready availability of the compound, $R^1$ is preferably hydrogen, methyl, ethyl, hydroxymethyl, or 2-hydroxyethyl, more preferably hydrogen, hydroxymethyl, or 2-hydroxyethyl.

$R^2$ is a hydrogen atom, an alkyl group having 1 to 6 carbon atoms, or a hydroxyalkyl group having 1 to 5 carbon atoms. The C1-C6 alkyl group may be straight, branched, or cyclic. Examples of the alkyl group include methyl, ethyl, n-propyl, isopropyl, butyl (any isomer), pentyl (any isomer), hexyl (any isomer), cyclopentyl, and cyclohexyl. Examples of the C1-C5 hydroxyalkyl group are the same as those enumerated above. From the standpoint of deodorizing effect and availability of the compound, $R^2$ is preferably hydrogen, C1-C3 alkyl, or hydroxyethyl, more preferably hydrogen.

$R^3$ and $R^4$ each independently represent an alkylene group having 1 to 5 carbon atoms. $R^3$ and $R^4$ may be the same or different. The C1-C5 alkylene group may be straight or branched. Examples thereof include methylene, ethylene, trimethylene, propylene, and butylene (any isomer), with methylene being preferred.

Examples of the polyhydroxylamine compound as ingredient (B-9) include one or more compounds selected from tris(hydroxymethyl)aminomethane, 2-amino-1,3-propanediol, 2-amino-2-methyl-1,3-propanediol, 2-amino-2-ethyl-1, 3-propanediol, 2-amino-2-hydroxymethyl-1,3-propanediol, and 2-amino-2-hydroxyethyl-1,3-propanediol; and salts of these compounds with hydrochloric acid, sulfuric acid, nitric acid, phosphoric acid, carbonic acid, and so on. Preferred of them are tris(hydroxymethyl)aminomethane and its salt formed with hydrochloric acid in view of their deodorizing performance. The polyhydroxylamine compounds can be prepared in a usual manner.

With the object of imparting a satisfactory deodorizing effect, the content of ingredient (B-9) in the liquid cosmetic composition is 0.01 mass % or more, preferably 0.02 mass % or more, more preferably 0.05 mass % or more, even more preferably 0.07 mass % or more. With the object of obtaining both the deodorizing effect and the good touch of the hair after use, the content of ingredient (B-9) in the liquid cosmetic composition is 2 mass % or less, preferably 1 mass % or less, more preferably 0.5 mass % or less. Specifically, the content of ingredient (B-9) in the liquid cosmetic composition is 0.01 mass % to 1 mass %, preferably 0.05 mass % to 0.5 mass %. When the content of the polyhydroxylamine compound in the liquid cosmetic composition is in that range, both the deodorizing effect and the pleasant touch of the hair after use can be achieved.

The anionic thickening polymer as ingredient (B-10) is preferably a thickening polymer composed of at least one monomer having an anionic group selected from a carboxyl group and a sulfo group per molecule, more preferably a thickening polymer composed of at least one monomer selected from acrylic acid and methacrylic acid and cross-linked by one or more polyhydroxy compound allyl ethers, even more preferably a thickening polymer including at least one polymer selected from acrylate polymers and taurate polymers. Examples of the anionic thickening polymer include naturally occurring polymers, such as xanthan gum, carrageenan, and alginic acid; semi-synthetic polymers, such as hydroxyethyl xanthan gum, hydroxypropyl xanthan gum, and sodium carboxymethyl cellulose; and synthetic polymers, such as acrylate polymers and taurate polymers. Preferred of them are acrylate polymers and taurate polymers for their capabilities of imparting a clean feeling after use, deodorizing, and imparting a pleasant touch to the hair.

Examples of the acrylate thickening polymers include carbomers, which are acrylic acid polymers crosslinked by an allyl ether of pentaerythritol, an allyl ether of sucrose, or an allyl ether of propylene (e.g., Carbopol 910, Carbopol 934, Carbopol 940, Carbopol 941, Carbopol 980, Carbopol 981, Carbopol Ultrez 10, and Carbopol Ultrez 30, all from Lubrizol); acrylates/C10-C30 alkyl acrylate crosspolymers, which are copolymers of at least one of acrylic acid and methacrylic acid and a C10-C30 alkyl acrylate, crosslinked with an allyl ether of sucrose or an allyl ether of pentaerythritol (e.g., Carbopol Ultrez 20, Carbopol Ultrez 21, Carbopol ETD 2020, Pemulen TR-1, and Pemulen TR-2, all from Lubrizol); acylates/steareth-20 methacrylate copolymers, which are copolymers of at least one monomer selected from acrylic acid, methacrylic acid, and their simple esters and an ester of methacrylic acid and a C10-C30 polyoxyalkylene ether (e.g., Aculyn 22, Aculyn 88, both from The Dow Chemical Co.); acrylates/beheneth-25 methacrylate copolymers (e.g., Aculyn 28, from The Dow Chemical); acrylates/vinyl neodecanoate crosspolymers, which are copolymers of vinyl neodecanoate and at least one monomer selected from acrylic acid, methacrylic acid, and their simple esters, crosslinked with an allyl ether of trimethylolpropane or an allyl ether of pentaerythritol (e.g., Aculyn 38, from The Dow Chemical); and polyacrylate crosspolymer-3, which is methacrylic acid crosslinked with trimethylolpropane triacrylate or trimethylolpropane diallyl ether. Preferred of them are carbomers and acrylates/C10-C30 alkyl acrylate crosspolymers.

Examples of the taurate synthetic polymers include ammonium acryloyldimethyltaurate/beheneth-25 methacrylate crosspolymers (e.g., Aristoflex HMB, from Clariant Japan), hydroxyethyl acrylate/sodium acryloyldimethyltaurate copolymers (e.g., Sepinov EMT10 and Simulgel NS, both from Seppic), ammonium aryloyldimethyltaurate/VP copolymers (e.g., Aristoflex AVC, from Clariant Japan), ammonium acryloyldimethyltaurate/carboxyethylammonium acrylate crosspolymer (e.g., Aristoflex TAC, from Clariant Japan), acrylamide/sodium acryloylmethyltaurate/acrylic acid copolymers (e.g., Acudyne SCP, from The Dow Chemical), acrylamide/sodium acryloyldimethyltaurate copolymers (e.g., Simulgel 600, from Seppic), dimethylacrylamide/sodium acryloyldimethyltaurate crosspolymer (e.g., SU Polymer G-1, from Toho Chemical Industry), sodium acrylate/acryloyldimethyltaurate/dimethylacrylamide crosspolymers (e.g., Sepinov P88, from Seppic), sodium acryloyldimethyltaurate/methacrylamide laurate copolymers (e.g., AMO-51, from Daito Kasei Kogyo), sodium acryloyldimethyltaurate/VP crosspolymers (e.g., Aristoflex AVS, from Clariant Japan), poly(ammonium acryloyldimethyltaurate) (e.g., Gransil APL-1, from Grant Industries), sodium acrylate/sodium acryloyldimethyltaurate copolymers (e.g., Spinov EG-P, from Seppic), and poly(sodium acryloyldimethyltaurate) (e.g., Simulgel 800, from Seppic). Preferred of them are (ammonium acryloyldimethyltaurate/beheneth-25 methacrylate crosspolymers, hydroxyethyl acrylate/sodium acryloyldimethyltaurate copolymers, and ammonium acryloyldimethyltaurate/VP copolymers. Ammonium acryloyldimethyltaurate/beheneth-25 methacrylate copolymers are more preferred.

The anionic thickening polymers may be used either individually or in combination of two or more thereof as ingredient (B-10). The content of ingredient (B-10) in the liquid cosmetic composition is preferably 0.01 mass % or more, more preferably 0.02 mass % or more, even more preferably 0.05 mass % or more, in terms of smooth glide between the sheet and hair during cleaning operation, smoothness in running fingers through hair, and uniform application of the liquid cosmetic composition to the whole hair and scalp for imparting a deodorant effect, and preferably 1 mass % or less, more preferably 0.7 mass % or less, even more preferably 0.5 mass % or less, with the view of adding a fluffy finish to the hairstyle after drying, imparting a pleasant touch to the hair, and obtaining a strong clean feeling while reducing a feeling of residue during cleaning operation. Specifically, the content of ingredient (B-10) in the liquid cosmetic composition is preferably 0.01 mass % to 1 mass %, more preferably 0.02 mass % to 0.7 mass %, even more preferably 0.05 mass % to 0.5 mass %. When the anionic thickening polymer content in the liquid cosmetic composition is in the range recited above, the liquid cosmetic composition acquires a sufficient viscosity to be infiltrated into the substrate sheet in a necessary and sufficient amount and to be prevented from dripping from the substrate sheet. Having a suitable viscosity, the liquid cosmetic composition containing the polyhydroxylamine compound (B-9) can be applied to the hair and scalp uniformly.

The cooling agent (B-7) is used with the object of preventing ingredient (B-10) in the liquid cosmetic composition from causing a feeling of residue of the liquid cosmetic composition after use, inhibiting reduction of a clean feeling due to the liquid cosmetic composition remaining on the scalp, and imparting a fresh feeling. The liquid cosmetic composition for use in the present embodiment can be formulated so as to prolong the clean and fresh feeling by incorporating a combination of the specific ingredient (B-10) and ingredient (B-7) and by adjusting the viscosity to a hereinafter described proper range.

The cooling agent as ingredient (B-7) may be the same as used in the liquid cosmetic composition of the fifth embodiment.

The content of the cooling agent (B-7) in the liquid cosmetic composition is 0.01 mass % or more, preferably 0.05 mass % or more, more preferably 0.1 mass % or more, and 1.0 mass % or less, preferably 0.5 mass % or less.

The pH of the liquid cosmetic composition used in the present embodiment is 6 or higher, preferably 6.5 or higher, more preferably 6.8 or higher, in terms of a satisfactory deodorizing effect, and 9.5 or lower, preferably 9.0 or lower, more preferably 8.5 or lower, in terms of low irritation to the scalp as well as a satisfactory deodorizing agent.

In order for the liquid cosmetic composition used in the present embodiment to provide a smooth glide between the substrate sheet and hair during cleaning operation, to make the hair easy to run fingers through, and to be uniformly applied to the whole hair and scalp for obtaining satisfactory deodorizing effect and achieving a long-lasting fresh feeling, the solution viscosity of the liquid cosmetic composition at 30° C. is 5 mPa·s or higher, preferably 10 mPa·s or higher, more preferably 50 mPa·s or more, even more preferably 100 mPa·s or more. In order for the liquid cosmetic composition to impart a pleasant touch to the hair after use, to leave no excessive sticky feeling on the user's hand and fingers, to impart a clean feeling with reduced feeling of residue of the liquid cosmetic composition, and to prolong the fresh feeling, the solution viscosity of the liquid cosmetic composition at 30° C. is 5,000 mPa·s or lower, preferably 3,000 mPa·s or lower, more preferably 1000 mPa·s or lower. Specifically, the solution viscosity of the liquid cosmetic composition is 5 mPa·s to 5,000 mPa·s, preferably 10 mPa·s to 3,000 mPa·s, more preferably 50 mPa·s to 1,000 mPa·s. The solution viscosity of the liquid cosmetic composition at 30° C. is measured using a Brookfield viscometer. The measuring conditions are selected as appropriate to the viscosity of the liquid. As far as the viscosity of the liquid cosmetic composition used in the invention is concerned, measurement is usually taken using a rotor No. M2 up to viscosities of 1,000 mPa·s and a rotor No. M3 for viscosities above 1,000 mPa·s. The number of rotation of the rotor is 60 rpm up to viscosities of 500 mPa·s, 30 rpm between 500 mPa·s and 4,000 mPa·s, and 12 rpm for viscosities above 4,000 mPa·s.

In addition to the aforementioned ingredients, the liquid cosmetic composition for use in the present embodiment may contain the alcohol (B-1) with the object of ensuring removal of dirt from hair and scalp. Preferred alcohols include ethanol, propanol, isopropyl alcohol, 1,3-butylene glycol, dipropylene glycol, and glycerol. Preferred of them are ethanol, propanol, and isopropyl alcohol in terms of reducing a feeling of the liquid cosmetic composition remaining on the hair thereby ensuring the clean feeling.

The content of the alcohol (B-1) in the liquid cosmetic composition is preferably 5 mass % or more, more preferably 10 mass % or more, even more preferably 20 mass % or more, to secure removal of hair and scalp dirt, and preferably 60 mass % or less, more preferably 50 mass % or less, even more preferably 40 mass % or less, still even more preferably 35 mass % or less, to control the irritation to the skin as well as to secure hair and scalp dirt removal. Specifically, the content of the alcohol (B-1) in the liquid cosmetic composition is preferably 5 mass % to 60 mass %, more preferably 10 mass % to 50 mass %, even more preferably 20 mass % to 35 mass %. In particular, in order to reduce a feeling of the liquid cosmetic composition remaining on the hair and to provide an increased clean feeling, it is preferred to restrict the content of a polyhydric alcohol. The polyhydric alcohol content in the liquid cosmetic composition is 0.3 mass % or less, preferably 0.1 mass % or less, more preferably 0.05 mass % or less.

The liquid cosmetic composition for use in the invention may further contain a surfactant, a powder imparting smoothness and silkiness to the hair, a deodorant other than ingredient (B-9), an antiseptic, a fragrance, a chelating agent, a warming agent, and so forth.

Figure 5:
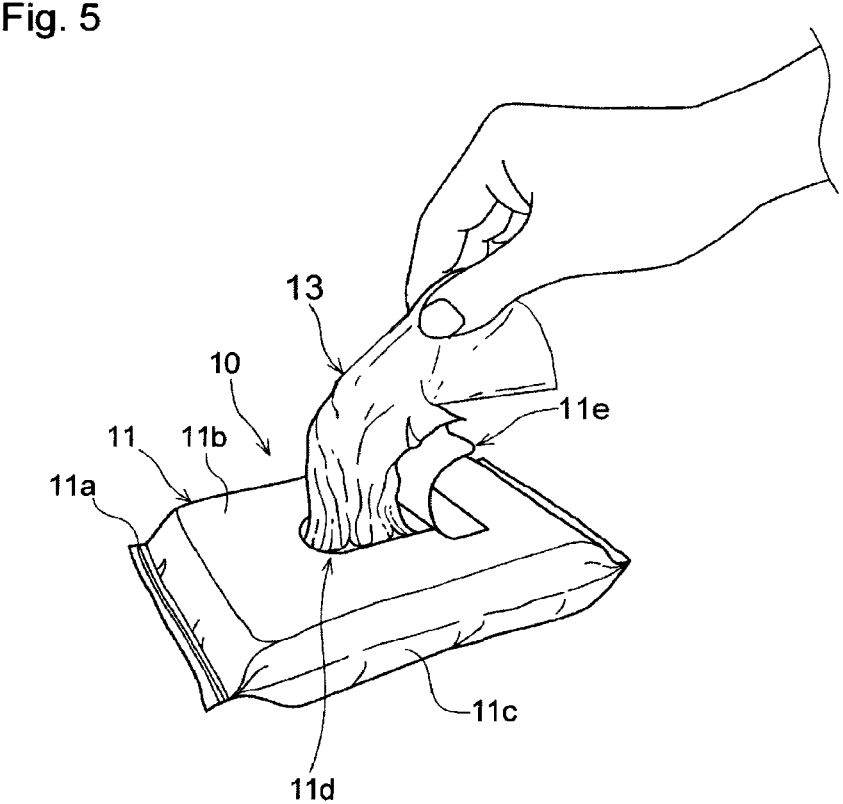
FIG. 5 is a perspective view illustrating a wet sheet-like hair care product being picked up and taken out of the hair care product shown in FIG. 1.

An exemplary usage of the sheet-like hair care products of the foregoing embodiments will then be described. A usage of the sheet-like hair care product of the first embodiment will be described first. In the case of using the hair care product 10 shown in FIG. 1, the peel-and-reseal label 11e attached to the upper surface 11b of the packaging container 11 is peeled to expose the access opening 11d. As shown in FIG. 5, the substrate sheet 12 is pinched by fingers and taken out of the packaging container 11 through the access opening 11d. While being taken out in that way, the sheet-like hair care product 13 gets caught on the edge of the access opening 11d and unfolded and spread out easily.

Figure 6:
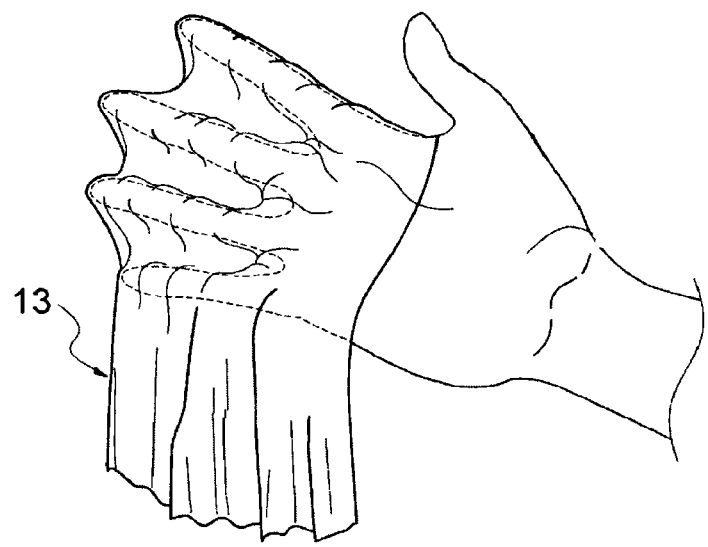
FIG. 6 is a perspective view illustrating the wet sheet-like hair care product spread out on the palmer side of a user's hand.

Since the sheet-like hair care product 13 has a high degree of drape with low bending resistance, when the thus spread out sheet is placed on the palmer side of a user's hand, it easily conforms to the shape of the hand as shown in FIG. 6 to get ready to conduct wiping operation on the hair and scalp. Since the sheet-like hair care product 13 retains the liquid cosmetic composition, it very easily deforms to the contour of the hand when allowed to hang under its own weight.

Figure 7:
FIG. 7 is a perspective view illustrating the start of treating/cleaning hair with the wet sheet-like hair care product.
Figure 8:
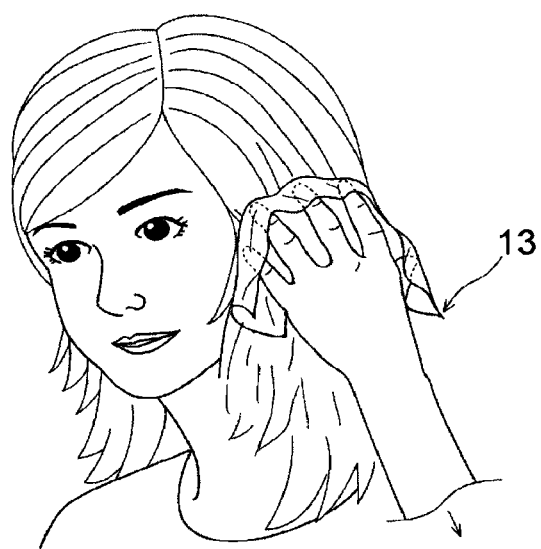
FIG. 8 is a perspective view illustrating the hair treating/cleaning operation.

As shown in FIG. 6, the sheet-like hair care product 13 is spread on the palmer side of a user's hand in such a manner that a part of the sheet-like hair care product 13 hangs over the fingertips, and the fingers with the sheet-like hair care product 13 on are applied to the roots of hair strands. For example, the tips of the fingers are placed on the roots of hair stands near the top of the head to bring the sheet-like hair care product 13 into contact with the hair strands as shown in FIG. 7. While keeping the contact, the hand is moved down from the roots to the tips of the hair strands to treat the hair as shown in FIG. 8. This operation may be carried out on the whole hair or part of the hair. The treating operation is preferably carried out repeatedly to treat the whole hair. In order to conduct the treating operation always with a clean surface of the sheet, each treating operation is preferably done while changing the position of the fingertips on the sheet-like hair care product 13.

When the manner of operation shown in FIGS. 7 and 8 is followed, the hair treatment is preferably carried out by placing the fingertips having the sheet-like hair care product 13 thereon on the roots of hair strands in such a manner that there be bunches of hair strands between adjacent fingers and running the fingers through the hair while holding the hair bunches therebetween. For example, it is a recommended manner of operation that the fingers with the sheet-like hair care product 13 thereon are curled into a claw shape, put on the roots of hair strands, and run through the hair with their tips in indirect contact with the scalp. In that way, the hair treating operation can be achieved more easily just like combing with fingers.

The hair treating operation may also be carried out as well by putting fingertips between the roots and tips of hair strands and moving the fingers to the ends of the strands in the same manner as described above. From the standpoint of applying the liquid cosmetic composition to the whole hair, the treating operation is preferably started from the roots of hair strands, though.

While FIG. 8 illustrates the operation of wiping clean the outer side of strands of hair, hair cleaning may also be performed by placing the palmer side of the hand on the inner side of hair strands (i.e., the side closer to the scalp), applying the fingertips with the sheet-like hair care product thereon to the roots or between the roots and tips of the hair strands to get bunches of hair strands in between adjacent fingers, and combing the hair by the fingers. By using the sheet-like hair care product 13 in that way, the liquid cosmetic composition can be applied evenly to those hairs that are not exposed to the exterior.

Figure 9A:
FIG. 9(a) and FIG. 9(b) are each a perspective view illustrating a hair treating/cleaning operation using the wet sheet-like hair care product.
Figure 9B:
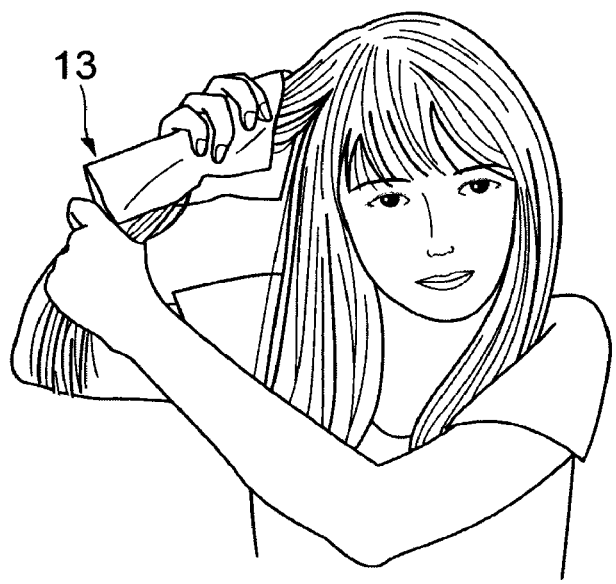

In FIGS. 9(a) and 9(b) is shown another usage of the hair care product 10. In the method shown, the sheet-like hair care product 13 is spread on the palmer side of a user's hand in such a manner that a part of the sheet-like hair care product 13 hangs over the fingertips as shown in FIG. 6. Simultaneously with or either before or after that, a portion of hair is taken out by the other hand to make a bunch of hair, and the bunch of hair is then grasped by the hand having the sheet-like hair care product 13 thereon. The position of the bunch of hair to be grasped by the hand is preferably near the roots. The hand having the bunch of hair grasped therein is moved toward the end of the bunch of hair as shown in FIG. 9(b). By so gliding the sheet-like hair care product 13 from the root to the end of the bunch of hair, the liquid cosmetic composition impregnating the substrate sheet 12 is allowed to penetrate the bunch of hair effectively. The operation may be carried out on the whole hair or a part of hair. The usage described is especially effective in making a straight hairstyle.

Figure 10A:
FIG. 10(a) and FIG. 10(b) are each a perspective view illustrating another hair treating/cleaning operation using the wet sheet-like hair care product.
Figure 10B:

Still another usage of the hair care product 10 is shown in FIGS. 10(a) and 10(b). In this method of use, the sheet-like hair care product 13 is spread on the palmer side of a user's hand in such a manner that part of the sheet-like hair care product 13 hangs over the fingertips as shown in FIG. 6. Simultaneously with or either before or after that, a portion of hair is taken out by the other hand to make a bunch of hair, which is grasped by the other hand preferably by almost the middle of its length or near the tips. Then, the tip of the bunch of hair and its vicinity are held in the hand with the sheet-like hair care product 13 thereon, and the hand having the bunch of hair therein is repeatedly opened and closed to knead the tips of the hair strands and their vicinity as shown in FIG. 10(b), whereby the kneaded hair strands are curled. This operation is preferably repeated while changing the place to take out a portion of hair. The operation may be carried out on the whole hair or part of it. The position of the taken out bunch of hair to be kneaded by the hand may be from the root to the tip or from the middle to the tip. The usage described above is especially effective in fixing naturally curly or chemically waved hair into a wavy hairstyle.

Figure 11:
FIG. 11 is a perspective view illustrating the beginning of scalp cleaning from the hairline at the nape of a user's neck.

FIG. 11 illustrates a usage differing from any of the above described usages. In the method of FIG. 11, fingers of a user's hand on which the sheet-like hair care product 13 is placed are inserted into hair along the hairline at the nape of the user's neck to contact the scalp indirectly. The hand kept in contact with the scalp is moved shortly to-and-fro vertically or horizontally to rub the scalp with fingers in a to-and-fro vertical or horizontal motion while moving the hand upward as a whole, whereby the dirt is removed from the scalp. The dirt may be removed from the inner side of hair strands by inserting the fingers having the sheet on from the side of the head to hold hair strands between adjacent fingers and moving the hand from the roots to the tips of the hair strands. It is only necessary that the fingertips be contacted with the hair via the substrate sheet 12 and glided vertically or horizontally. For example, a part is made in the hair to expose the scalp, which is contacted and rubbed vertically or horizontally by the fingers via the sheet-like hair care product 13. With the object of cleaning all over the head uniformly and efficiently, it is recommended to place the fingers with the sheet thereon first along the hairline.

Figure 12A:
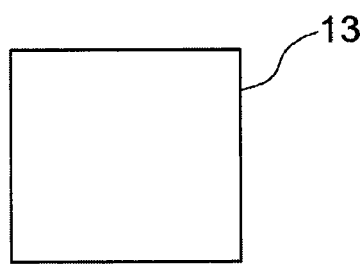
FIG. 12(a), FIG. 12(b), FIG. 12(c), FIG. 12(d), and FIG. 12(e) are perspective views illustrating another scalp cleaning operation using the wet sheet-like hair care product.
Figure 12B:
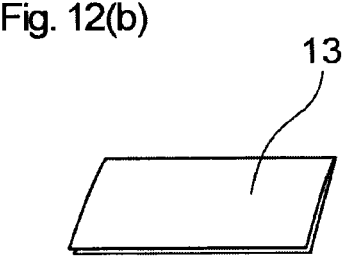
Figure 12C:
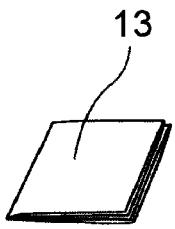
Figure 12D:
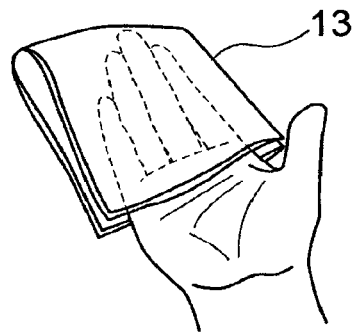
Figure 12E:
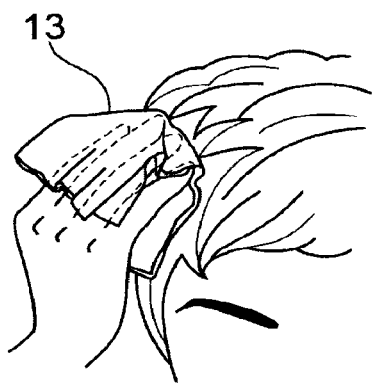

FIGS. 12(a) through 12(e) illustrate a method for cleaning scalp which is different from the method shown in FIG. 11. In this method, the spread out sheet-like hair care product 13 shown in FIG. 12(a) is folded in two as shown in FIG. 12(b), and then the folded hair care product 13 is folded in two so that the folded hair care product 13 is folded in four as shown in FIG. 12(c). User's fingers are inserted into the inside of the four-folded sheet-like hair care product 13 to hold the sheet-like hair care product 13 as shown in FIG. 12(d). The hand holding the sheet-like hair care product hair care product (13) is brought into contact with the scalp and rubbed against the scalp via the sheet-like hair care product 13 to clean the scalp as shown in FIG. 12(e). Placing the fingertips at a part of the hair helps the fingertips to reach the scalp. The way of folding the sheet-like hair care product 13 is not limited to that shown.

After completion of the hair and scalp cleaning, the hair may be fixed by bushing or finger combing if desired.

It is advisable not to rinse off the liquid cosmetic composition transferred from the sheet-like hair care product 13 to the hair or scalp until, for example, 3 hours, preferably 5 hours, more preferably 8 hours after completion of the hair and scalp cleaning.

In using the sheet-like hair care product of the second embodiment, the methods shown in FIGS. 5 through 10 are preferably adopted. In using the sheet-like hair care products of the third to sixth embodiments, the methods shown to FIGS. 5 through 9, 11, and 12 are preferred.

While the invention has been described based on its preferred embodiments, the invention is not deemed to be limited to the embodiments described. For instance, although the substrate sheet 12 shown in FIGS. 2 through 4 is preferred, the substrate sheet that can be used in the invention is not limited thereto.

The shape of the packaging container 11 is not limited to the pillow shape as described. For example, the packaging container may be a container having a hinged flip as a lid.

The liquid cosmetic composition impregnating the substrate sheet for use in the invention is not limited to those used in the first to sixth embodiments, and may be impregnated with another liquid cosmetic composition.

The following clauses are disclosed as further description of the sheet-like hair care product and methods for treating hair and/or cleaning scalp using the sheet-like hair care product according to the above described embodiments.

[1] A sheet-like hair care product comprising (A) a substrate sheet containing cellulosic fibers and having a bending resistance of 10 to 70 mm as measured by the 45° cantilever method in accordance with JIS L1096:2010 and (B) a liquid cosmetic composition, component (A) being impregnated with 1 g to 50 g of component (B) per sheet.

[2] The sheet-like care product according to clause [1], wherein the substrate sheet preferably has a three-dimensional textured surface.

[3] The sheet-like hair care product according to clause [2], wherein the substrate sheet has a first side and a second side located opposite to the first side, and
the first side and the second side have a three-dimensional textured surface having raised portions and recessed portions.

[4] The sheet-like hair care product according to clause [2] or [3], wherein the thickness of the substrate sheet at the raised portion on one of the first side and the second side is preferably larger than the thickness of the substrate sheet at the recessed portion on the same side, the one of the first side and the second side being the side having a larger difference in height from the bottom of the recessed portion to the top of the raised portion than that on the other side.

[5] The sheet-like hair care product according to any one of clauses [2] to [4], wherein, in a plan view, the locations of the raised portions on the first side are substantially coincident with those on the second side.

[6] The sheet-like hair care product according to any one of clauses [2] to [5], wherein the substrate sheet preferably has a higher basis weight in the raised portions than in the recessed portions.

[7] The sheet-like hair care product according to any one of clauses [2] to [6], wherein the recessed portions and the raised portions preferably extend in a given direction in the plane of the substrate sheet, the recessed portions being preferably grooves, the raised portions being preferably ridges, and the grooves and the ridges alternating each other over the entire area of the substrate sheet.

[8] The sheet-like hair care product according to any one of clauses [2] to [7], wherein the ridges are preferably of the same shape and size and are arranged at substantially regular intervals, and each ridge preferably has a width W1, in direction X, of 0.5 mm or more, more preferably 0.8 mm or more, and preferably 3.0 mm or less.

[9] The sheet-like hair care product according to any one of clauses [2] to [8], wherein, ridges are preferably formed as the raised portions, grooves are preferably formed as the recessed portions, the height difference at the top of the ridge on the first side is preferably 0.2 mm to 1.2 mm, more preferably 0.2 mm to 1.0 mm, and the height difference at the top of the ridge on the second side is preferably 0.1 mm to 1.2 mm, more preferably 0.1 mm to 1.0 mm.

[10] The sheet-like hair care product according to any one of clauses [2] to [9], wherein each recessed portion preferably has a perforation.

[11] The sheet-like hair care product according to clause [10], wherein the distance L1 between adjacent perforations, which are formed in the recessed portions, is preferably 4.0 mm or more, and is preferably 15.0 mm or less, more preferably 8.0 mm or less.

[12] The sheet-like hair care product according to clauses [10] or [11], wherein the ratio of the diameter L2 (see FIG. 2) of the perforation to the width W2 of the groove, L2×100/W2, is preferably 20% or more, more preferably 30% or more, and preferably 90% or less.

[13] The sheet-like hair care product according to any one of clauses [1] to [12], wherein the substrate sheet preferably has a bending resistance of 10 mm or more, and 70 mm or less, more preferably 65 mm or less, even more preferably 60 mm or less.

[14] The sheet-like hair care product according to any one of clauses [1] to [13], wherein the substrate sheet preferably has a thickness of more than 0.3 mm, more preferably 0.4 mm or more, even more preferably 0.5 mm or more, still even more preferably 0.7 mm or more, and 5 mm or less, more preferably 4 mm or less, even more preferably 3 mm or less, still even more preferably 1.5 mm or less as measured in accordance with JIS L1096:2010 under a load of 0.3 kPa.

[15] The sheet-like hair care product according to any one of clauses [1] to [14], wherein the substrate sheet preferably has an apparent area of 50 $cm^2$ or more, more preferably 100 $cm^2$ or more, even more preferably 200 $cm^2$ or more, and 1600 $cm^2$ or less, more preferably 900 $cm^2$ or less, even more preferably 700 $cm^2$ or less.

[16] The sheet-like hair care product according to any one of clauses [1] to [15], wherein the substrate sheet is preferably a nonwoven fabric sheet that retains the form of nonwoven fabric only through entanglement of constituent fibers, the nonwoven fabric sheet being preferably a sheet made by hydroentanglement.

[17] The sheet-like hair care product according to any one of clauses [1] to [16], wherein the substrate sheet preferably contains cellulosic fibers and thermoplastic resin fibers.

[18] The sheet-like hair care product according to clauses [17], wherein the proportion of the cellulosic fibers in the substrate sheet is preferably larger than that of the thermoplastic resin fibers.

[19] The sheet-like hair care product according to any one of clauses [1] to [18], wherein the proportion of the cellulosic fibers in the mass of the substrate sheet before impregnation with the liquid cosmetic composition is preferably 30 mass % or more, more preferably 35 mass % or more, even more preferably 40 mass % or more, still even more preferably 50 mass % or more, and preferably 99 mass % or less, more preferably 97 mass % or less, even more preferably 95 mass % or less, and
the proportion of the thermoplastic resin fibers in the mass of the substrate sheet before impregnation with the liquid cosmetic composition is preferably 1 mass % or more, more preferably 3 mass % or more, even more preferably 5 mass % or more, still even more preferably 10 mass % or more, and preferably 70 mass % or less, more preferably 65 mass % or less, even more preferably 60 mass % or less, still even more preferably 50 mass % or less.

[20] The sheet-like hair care product according to any one of clauses [1] to [19], wherein the impregnated amount of the liquid cosmetic composition is preferably 6 g or more, more preferably 7 g or more, even more preferably 8 g or more, and preferably 30 g or less, more preferably 25 g or less, even more preferably 20 g or less, still even more preferably 15 g or less, per sheet.

[21] The sheet-like hair care product according to any one of clauses [1] to [20], wherein the content of the liquid cosmetic composition is preferably 5 mass % or more, more preferably 10 mass % or more, even more preferably 20 mass % or more, and preferably 90 mass % or less, more preferably 85 mass % or less, even more preferably 80 mass % or less, still even more preferably 60 mass % or less, relative to the maximum water content of the substrate sheet.

[22] The sheet-like hair care product according to any one of clauses [1] to [21], wherein the substrate sheet preferably has a maximum water retention of 700 mass % or more, more preferably 800 mass % or more, even more preferably 900 mass % or more, still even more preferably 1000 mass % or more, and 2000 mass % or less, more preferably 1500 mass % or less, even more preferably 1300 mass % or less.

[23] The sheet-like hair care product according to any one of clauses [1] to [22], further comprising (C) a packaging container having an access opening, and an openable and closable lid covering the access opening to seal the contents, the access opening having an area of 25 mm$^2$ or more, preferably 100 mm$^2$ or more, more preferably 200 mm$^2$ or more, and preferably 4000 mm$^2$ or less, more preferably 3000 mm$^2$ or less, even more preferably 2500 mm$^2$ or less, and the substrate sheet (A) impregnated with the liquid cosmetic composition (B) being held in the packaging container (C).

[24] The sheet-like hair care product according to any one of clauses [1] to [23], wherein the liquid cosmetic composition (B) comprises: (B-1) a mono- or polyhydric alcohol having 1 to 6 carbon atoms; (B-2) a surfactant; and (B-3) water.

[25] The sheet-like hair care product according to clauses [24], wherein the content of ingredient (B-1) in the liquid cosmetic composition is preferably 1 mass % or more, more preferably 5 mass % or more, even more preferably 10 mass % or more, and preferably 45 mass % or less, more preferably 35 mass % or less, even more preferably 30 mass % or less.

[26] The sheet-like hair care product according to clause [24] or [25], wherein the content of ingredient (B-2) in the liquid cosmetic composition is preferably 0.1 mass % or more, more preferably 0.2 mass % or more, even more preferably 0.3 mass % or more, and preferably 5 mass % or less, more preferably 4 mass % or less, even more preferably 3 mass % or less, still even more preferably 2 mass % or less.

[27] The sheet-like hair care product according to any one of clauses [24] to [26], wherein ingredient (B-2) is preferably a cationic surfactant.

[28] The sheet-like hair care product according to any one of clauses [24] to [26], wherein ingredient (B-2) is preferably an amphoteric surfactant or a nonionic surfactant.

[29] The sheet-like hair care product according to any one of clauses [24] to [26], wherein ingredient (B-2) is preferably a combination of a cationic surfactant and an amphoteric surfactant or a combination of a cationic surfactant and a nonionic surfactant.

[30] The sheet-like hair care product according to any one of clauses [24] to [29], wherein the liquid cosmetic composition further comprises (B-4) a silicone.

[31] The sheet-like hair care product according to any one of clauses [1] to [23], which is used for hairstyling and wherein the liquid cosmetic composition (B) comprises (B-3) water and (B-5) a film-forming resin, the film-forming resin (B-5) being present in the liquid cosmetic composition in an amount of 0.01 mass % to 20 mass %.

[32] The sheet-like hair care product according to clause [31], wherein the amount of the liquid cosmetic composition (B) is 1 g to 50 g per sheet.

[33] The sheet-like hair care product according to clause [31] or [32], wherein the content of the film-forming resin (B-5) in the liquid cosmetic composition is preferably 0.05 mass % or more, more preferably 0.1 mass % or more, and preferably 10 mass % or less, more preferably 5 mass % or less, even more preferably 3 mass % or less, still even more preferably 1 mass % or less.

[34] The sheet-like hair care product according to any one of clauses [31] to [33], wherein the film-forming resin (B-5) is preferably a cationic resin, more preferably at least one cationic resin selected from a vinylpyrrolidone-dimethylaminoethyl methacrylate copolymer diethylsulfate, a vinylpyrrolidone-dimethylaminopropylmethacrylamide-lauryldimethylaminopropylmet hacrylamide copolymer, poly(dimethylmethylenepiperidinium chloride), a dimethyldiallylammonium chloride-acrylamide copolymer, vinylpyrrolidone-N,N-dimethylaminoethyl methacrylate copolymer diethylsulfate, a vinylpyrrolidone-dimethylaminoethyl methacrylate copolymer, an N,N-dimethylaminoethyl methacrylate diethylsulfate-N,N-dimethylacrylamide-polyethylene glycol dimethacrylate copolymer, ammonium-modified hydroxyethyl cellulose, and an N-propionylpolyethyleneimine methylpolysiloxane copolymer.

[35] The sheet-like hair care product according to any one of clauses [31] to [34], wherein the film-forming resin (B-5) is preferably a nonionic resin, more preferably at least one nonionic resin selected from polyvinylpyrrolidone, a vinylpyrrolidone-vinyl acetate copolymer, a vinyl methyl ether-alkyl maleate copolymer, a vinylpyrrolidone-methacrylamide-vinylimidazole copolymer, and polyvinylcaprolactam.

[36] The sheet-like hair care product according to any one of clauses [31] to [34], wherein the film-forming resin (B-5) is preferably an amphoteric resin, more preferably at least one amphoteric resin selected from an acrylates-lauryl acrylate-stearyl acrylate-ethylamine oxide methacrylate copolymer, a methacryloyloxyethylcarboxybetaine-alkyl methacrylate copolymer, an octylacrylamide-hydroxypropyl acrylate-butylaminoethyl methacrylate copolymer, and an octylacrylamide-hydroxypropyl acrylate-butylaminoethyl methacrylate copolymer.

[37] The sheet-like hair care product according to any one of clauses [31] to [36], wherein the liquid cosmetic composition (B) preferably further contains ingredient (B-4), the ingredient (B-4) being (B-4-1) an amino-modified silicone.

[38] The sheet-like hair care product according to clause [37], wherein the ratio of the amino-modified silicone content (g) to the film forming resin content (g), (B-4-1) (g)/(B-5) (g), is preferably 0.01 or higher, more preferably 0.02 or higher, even more preferably 0.045 or higher, and preferably 14 or lower, more preferably 5 or lower, even more preferably 3 or lower, still even more preferably 1.5 or lower.

[39] The sheet-like hair care product according to any one of clauses [31] to [38], wherein the liquid cosmetic composition (B) preferably further comprises ingredient (B-2).

[40] The sheet-like hair care product according to clause [39], wherein the concentration of ingredient (B-2) in the liquid cosmetic composition is preferably 0.1 mass % or more, more preferably 0.2 mass % or more, even more preferably 0.3 mass % or more, and preferably 5 mass % or less, more preferably 4 mass % or less, even more preferably 3 mass % or less, still even more preferably 2 mass % or less.

[41] The sheet-like hair care product according to any one of clauses [24] to [30], [39], and [40], wherein ingredient (B-2) preferably comprises (B-2-1) a cationic surfactant.

[42] The sheet-like hair care product according to any one of clauses [30] to [41], wherein the liquid cosmetic composition (B) preferably further comprises ingredient (B-1), more preferably at least one member selected from ethanol, propanol, isopropyl alcohol, 1,3-butylene glycol, dipropylene glycol, and glycerol.

[43] The sheet-like hair care product according to clause [42], wherein the concentration of ingredient (B-1) in the liquid cosmetic composition (B) is preferably 1 mass % or more, more preferably 5 mass % or more, even more preferably 10 mass % or more, and preferably 45 mass % or less, more preferably 35 mass % or less, even more preferably 30 mass % or less.

[44] The sheet-like hair care product according to any one of clauses [1] to [23], wherein the liquid cosmetic composition (B) comprises (B-1-1) ethanol, (B-3) water, and (B-6) a polysaccharide,
the concentration of ingredient (B-1-1) is 10 mass % to 45 mass % in the liquid cosmetic composition, and
the concentration of ingredient (B-6) is 0.01 mass % to 0.4 mass % in the liquid cosmetic composition.

[45] The sheet-like hair care product according to clause [44], wherein ingredient (B-6) preferably has a weight average molecular weight of more than 50,000, more preferably 100,000 or more, even more preferably 250,000 or more, still even more preferably 500,000 or more, yet still even more preferably 1,000,000 or more, and preferably 2,000,000 or less, more preferably 1,800,000 or less, even more preferably 1,700,000 or less.

[46] The sheet-like hair care product according to clause [44] or [45], wherein ingredient (B-6) is a cationic polysaccharide or a nonionic polysaccharide, preferably a cationic polysaccharide, more preferably at least one member selected from cationic guar gum, cationic cellulose, cationic starch, cationic locust bean gum, cationic tara gum, and cationic fenugreek gum.

[47] The sheet-like hair care product according to any one of clauses [44] to [46], wherein ingredient (B-6) preferably has a cationic charge density of 0.1 meq/g or more, more preferably 0.2 meq/g or more, even more preferably 0.5 meq/g or more, and preferably 3.0 meq/g or less, more preferably 2.5 meq/g or less, even more preferably 2.0 meq/g or less.

[48] The sheet-like hair care product according to any one of clauses [44] to [47], wherein the content of the polysaccharide (B-6) in the liquid cosmetic composition is preferably 0.01 mass % or more, more preferably 0.02 mass % or more, even more preferably 0.05 mass % or more, still even more preferably 0.07 mass % or more, yet even more preferably 0.1 mass % or more, and 0.4 mass % or less, more preferably 0.35 mass % or less, even more preferably 0.3 mass % or less, still even more preferably 0.25 mass % or less, yet even more preferably 0.15 mass % or less.

[49] The sheet-like hair care product according to any one of clauses [44] to [48], wherein the concentration of ingredient (B-1-1) in the liquid cosmetic composition is preferably 10 mass % or more, and 45 mass % or less, more preferably 35 mass % or less, even more preferably 30 mass % or less.

[50] The sheet-like hair care product according to any one of clauses [44] to [49], wherein the liquid cosmetic composition preferably has a viscosity at 30° C. of 5 mPa·s or more, more preferably 10 mPa·s or more, and 5,000 mPa·s or less, more preferably 2,000 mPa·s or less, even more preferably 1000 mPa·s or less.

[51] The sheet-like hair care product according to any one of clauses [44] to [50], wherein the liquid cosmetic composition (B) is preferably free from (B-2-2) an anionic surfactant or preferably contains the anionic surfactant in a concentration of 0.1 mass % or less, more preferably 0.05 mass % or less, even more preferably 0.01 mass % or less, and 0.00001 mass % or more.

[52] The sheet-like hair care product according to any one of clauses [1] to [23], wherein the liquid cosmetic composition comprises: (B-2-3) a polyoxyalkylene-added nonionic surfactant; (B-3) water; (B-4-1) an organopolysiloxane represented by following general formula (1); and (B-8) a fragrance, and
the concentration of ingredient (B-2-3) in the liquid cosmetic composition is 0.1 mass % to 2 mass %.

[Chem. 3]

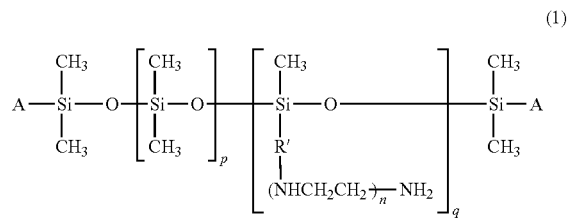

(1)

wherein A represents —R, —R—(NHCH$_2$CH$_2$)$_n$NH$_2$—, —OR, or a hydroxyl group; R represents an optionally substituted monovalent hydrocarbon group having 1 to 20 carbon atoms; R' represents a divalent hydrocarbon group having 1 to 8 carbon atoms; n represents an integer of 0 to 3; p and q each represent a number that satisfies the relationship: 50≤(p+q+2)≤20,000, wherein (p+q+2) is a number-average total number of silicon atoms; and the amino equivalent is 500 g/mol to 100,000 g/mol.

[53] The sheet-like hair care product according to clause [52], wherein ingredient (B-2-3) comprises at least one member selected from (B-2-3-1) and (B-2-3-2), preferably ingredient (B-2-3) comprises both ingredients (B-2-3-1) and (B-2-3-2),
(B-2-3-1) includes at least one member selected from polyoxyalkylene monoalkyl ethers and polyoxyalkylene monoalkenyl ethers and (B-2-3-2), and
(B-2-3-2) includes at least one member selected from polyoxyalkylene castor oils and polyoxyalkylene hydrogenated castor oils.

[54] The sheet-like hair care product according to clause [52] or [53], wherein the ratio of the sum of the content n$_A$ (mass %) of ingredient (B-4-1) and the content n$_{B8}$ (mass %) of ingredient (B-8) to the content n$_{Ca}$ (mass %) of ingredient (B-2-3), [n$_A$+n$_{B8}$]/n$_{Ca}$, is preferably 0.05 or higher, more preferably 0.075 or higher, even more preferably 0.1 or higher, and preferably 0.65 or lower, more preferably 0.5 or lower, even more preferably 0.3 or lower, and (B-4-1), (B-8) and (B-2-3) being included in the liquid cosmetic composition.

[55] The sheet-like hair care product according to any one of clauses [52] to [54], wherein the content n$_{B8}$ (mass %) of ingredient (B-8) in the liquid cosmetic composition is preferably 0.0001 mass % or more, more preferably 0.01 mass % or more, and preferably 0.5 mass % or less, more preferably 0.2 mass % or less, even more preferably 0.1 mass % or less.

[56] The sheet-like hair care product according to clause [53], wherein the ratio of the content n$_{C-1}$ (mass %) of ingredient (B-2-3-1) to the content n$_{C-2}$ (mass %) of ingredient (B-2-3-2), n$_{C-1}$/n$_{C-2}$, is preferably 0.1 or higher, more preferably 0.2 or higher, even more preferably or 0.5 or higher, and preferably 10 or lower, or more preferably 2 or lower, and (B-2-3-1) and ingredient (B-2-3-2) being included in the liquid cosmetic composition.

[57] The sheet-like hair care product according to any one of clauses [52] to [56], wherein the content n$_{Ca}$ of ingredient (B-2-3) in the liquid cosmetic composition is preferably 0.05 mass % or more, more preferably 0.1 mass % or more, even more preferably 0.5 mass % or more, and preferably 2 mass % or less, more preferably 1.5 mass % or less, even more preferably 1 mass % or less.

[58] The sheet-like hair care product according to any one of clauses [52] to [57], wherein the liquid cosmetic composition preferably further contains (B-2-1) a cationic surfactant.

[59] The sheet-like hair care product according to any one of clauses [52] to [58], wherein the liquid cosmetic composition contains as ingredient (B-2-3-1) a secondary alcohol alkoxylate and a primary alcohol alkoxylate.

[60] The sheet-like hair care product according to any one of clauses [53] to [59], wherein the content $n_A$ of ingredient (B-4-1) in the liquid cosmetic composition is preferably 0.01 mass % or more, more preferably 0.02 mass % or more, even more preferably 0.05 mass % or more, still even more preferably 0.07 mass % or more, yet even more preferably 0.1 mass % or more, and preferably 1 mass % or less, more preferably 0.5 mass % or less, even more preferably 0.2 mass % or less.

[61] The sheet-like hair care product according to any one of clauses [52] to [60], wherein the total number of silicon atoms (p+q+2) of ingredient (B-4-1) is preferably 100 or greater, more preferably 300 or greater, even more preferably 500 or greater, still even more preferably 800 or greater, and preferably 10000 or smaller, more preferably 5000 or smaller, even more preferably 3000 or smaller.

[62] The sheet-like hair care product according to any one of clauses [52] to [61], wherein the amino equivalent of ingredient (B-4-1) is preferably 500 g/mol or more, preferably 1000 g/mol or more, more preferably 2000 g/mol or more, and 100,000 g/mol or less, preferably 80,000 g/mol or less, more preferably 50,000 g/mol or less.

[63] The sheet-like hair care product according to any one of clauses [52] to [62], wherein the liquid cosmetic composition (B) preferably further contains ingredient (B-1), more preferably, as the ingredient (B-1), at least at least one member selected from ethanol, propanol, isopropyl alcohol, 1,3-butylene glycol, dipropylene glycol, and glycerol.

[64] The sheet-like hair care product according to clauses [63], wherein the concentration of ingredient (B-1) in the liquid cosmetic composition is preferably 1 mass % or more, more preferably 5 mass % or more, even more preferably 10 mass % or more, and preferably 50 mass % or less, more preferably 40 mass % or less, even more preferably 30 mass % or less.

[65] The sheet-like hair care product according to any one of clauses [1] to [23], wherein the liquid cosmetic composition (B) comprises: (B-2-3-1) at least one member selected from polyoxyalkylene monoalkyl ethers and polyoxyalkylene monoalkenyl ethers; (B-2-3-2) at least one member selected from polyoxyalkylene castor oils and polyoxyalkylene hydrogenated castor oils; (B-3) water; (B-4-1) an organopolysiloxane represented by following general formula (1); and (B-7) a cooling agent,

[Chem. 4]

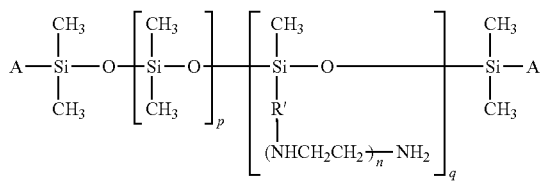

(1)

wherein A represents —R, —R—(NHCH$_2$CH$_2$)$_n$NH$_2$—, —OR, or a hydroxyl group; R represents an optionally substituted monovalent hydrocarbon group having 1 to 20 carbon atoms; R' represents a divalent hydrocarbon group having 1 to 8 carbon atoms; n represents an integer of 0 to 3; p and q each represent a number that satisfies the relationship: 50≤(p+q+2)≤20,000, wherein (p+q+2) is a number-average total number of silicon atoms; and the amino equivalent is 500 to 100,000 g/mol, and the ratio of the sum of the content $n_A$ (mass %) of ingredient (B-4-1) and the content $n_{B7}$ (mass %) of ingredient (B-7) to the sum of the content $n_C$ (mass %) of ingredient (B-2-3-1) and the content $n_D$ (mass %) of ingredient (B-2-3-2), $[n_A+n_{B7}]/[n_C+n_D]$, being 0.01 or higher, 0.05 or higher, or 0.1 or higher, and 1 or lower, 0.8 or lower, 0.6 or lower, 0.4 or lower, or 0.3 or lower.

[66] The sheet-like hair care product according to clause [65], wherein ingredient (B-7) is preferably l-menthol, menthyl acetate, menthyl lactate, l-menthyl glycerol ether, menthylpyrrolidone carboxylate, N-ethyl-p-menthane-carboxyamide, de-camphor, isopulegol, cineol, borneol, thymol, 3-l-methoxypropanediol, Japanese mint oil, and peppermint oil, more preferably l-menthol.

[67] The sheet-like hair care product according to clause [65] or [66], wherein the content $n_{B7}$ of ingredient (B-7) in the liquid cosmetic composition is preferably 0.01 mass % or more, more preferably 0.02 mass % or more, even more preferably 0.03 mass % or more, and preferably 0.5 mass % or less, more preferably 0.2 mass % or less, even more preferably 0.1 mass % or less.

[68] The sheet-like hair care product according to any one of clauses [65] to [67], wherein the ratio of the content $n_C$ (mass %) of ingredient (B-2-3-1) to the content $n_D$ (mass %) of ingredient (B-2-3-2), $n_C/n_D$, is preferably 0.01 or greater, more preferably 0.1 or greater, even more preferably 0.3 or greater, still even more preferably 0.5 or greater, yet even more preferably or 0.6 or greater, and preferably 0.95 or smaller, more preferably 0.9 or smaller, even more preferably 0.8 or smaller, still even more preferably or 0.75 or smaller.

[69] The sheet-like hair care product according to any one of clauses [65] to [68], wherein the content $n_C$ of ingredient (B-2-3-1) in the liquid cosmetic composition is preferably 0.01 mass % or more, more preferably 0.05 mass % or more, even more preferably 0.1 mass % or more, still even more preferably 0.2 mass % or more, yet even more preferably 0.4 mass % or more, and preferably 1 mass % or less, more preferably 0.8 mass % or less, even more preferably 0.7 mass % or less, still even more preferably 0.6 mass % or less.

[70] The sheet-like hair care product according to any one of clauses [65] to [69], wherein the content $n_D$ of ingredient (B-2-3-2) in the liquid cosmetic composition is preferably 0.01 mass % or more, more preferably 0.05 mass % or more, even more preferably 0.1 mass % or more, still even more preferably 0.5 mass % or more, and preferably 2 mass % or less, more preferably 1.5 mass % or less, even more preferably 1.0 mass % or less, still even more preferably 0.8 mass % or less.

[71] The sheet-like hair care product according to any one of clauses [1] to [22], wherein the liquid cosmetic composition comprises: (B-9) 0.01 to 2 mass % of a polyhydroxylamine represented by following general formula (2) and/or a salt thereof; (B-10) an anionic thickening polymer; (B-7) a cooling agent; and (B-3) water, and the liquid cosmetic composition has a pH of 6 to 9.5, and has a solution viscosity of 5 to 5,000 mPa·s at 30° C.

[Chem. 5]

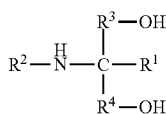

(2)

wherein $R^1$ represents a hydrogen atom, an alkyl group having 1 to 5 carbon atoms, or a hydroxyalkyl group having 1 to 5 carbon atoms; $R^2$ represents a hydrogen atom, an alkyl group having 1 to 6 carbon atoms, or a hydroxyalkyl group having 1 to 5 carbon atoms; $R^3$ and $R^4$, which may be the same or different, each represent an alkylene group having 1 to 5 carbon atoms.

[72] The sheet-like hair care product according to clause [71], wherein the polyhydroxylamine represented by general formula (2) as ingredient (B-9) is at least one compound selected from tris(hydroxymethyl)aminomethane, 2-amino-1,3-propanediol, 2-amino-2-methyl-1,3-p-propanediol, 2-amino-2-ethyl-1,3-propanediol, 2-amino-2-hydroxymethyl-1,3-propanediol, and 2-amino-2-hydroxyethyl-1,3-propanediol, more preferably tris(hydroxymethyl)aminomethane.

[73] The sheet-like hair care product according to clause [71] or [72], wherein the concentration of ingredient (B-9) in the liquid cosmetic composition is preferably 0.02 mass % or more, more preferably 0.05 mass % or more, even more preferably 0.07 mass % or more, and preferably 2 mass % or less, more preferably 1 mass % or less, even more preferably 0.5 mass % or less.

[74] The sheet-like hair care product according to any one of clauses [71] to [73], wherein the proportion of ingredient (B-10) in the liquid cosmetic composition is 0.01 mass % or more, preferably 0.02 mass % or more, more preferably 0.05 mass % or more, and preferably 1 mass % or less, more preferably 0.7 mass % or less, even more preferably 0.5 mass % or less.

[75] The sheet-like hair care product according to any one of clauses [71] to [74], wherein ingredient (B-10) is a thickening polymer having at least one monomer containing an anionic group selected from a carboxyl group and a sulfo group per molecule, preferably a polymer having at least one monomer selected from acrylic acid and methacrylic acid and crosslinked by at least one polyhydroxy compound allyl ether, more preferably a polymer comprising at least one polymer selected from acrylate polymers and taurate polymers.

[76] The sheet-like hair care product according to any one of clauses [71] to [75], wherein the liquid cosmetic composition has a viscosity, at 30° C., of 5 mPa·s or more, more preferably 10 mPa·s or more, even more preferably 50 mPa·s or more, still even more preferably 100 mPa·s or more, and preferably 5,000 mPa·s or less, more preferably 3,000 mPa·s or less, even more preferably 1000 mPa·s or less.

[77] The sheet-like hair care product according to any one of clauses [71] to [76], wherein the concentration of ingredient (B-7) in the liquid cosmetic composition is preferably 0.01 mass % or more, more preferably 0.05 mass % or more, even more preferably 0.1 mass % or more, and preferably 1.0 mass % or less, more preferably 0.5 mass % or less.

[78] The sheet-like hair care product according to any one of clauses [71] to [77], wherein the liquid cosmetic composition (B) preferably further contains ingredient (B-1), more preferably, the ingredient (B-1), at least one member selected from ethanol, propanol, isopropyl alcohol, 1,3-butylene glycol, dipropylene glycol, and glycerol.

[79] The sheet-like hair care product according to clause [78], wherein the concentration of ingredient (B-1) in the liquid cosmetic composition is 5 mass % or more, preferably 10 mass % or more, more preferably 20 mass % or more, and 60 mass % or less, preferably 50 mass % or less, more preferably 40 mass % or less, even more preferably 35 mass % or less.

[80] Use of the sheet-like product according to any one of clauses [1] to [79] as a hair care product.

[81] A method for treating hair using the sheet-like hair care product according to any one of clauses [1] to [79], including the steps of:
(i) when the sheet-like hair care product is held in a packaging container having an access opening, optionally picking up the sheet-like hair care product impregnated with the liquid cosmetic composition from the packaging container through the access opening,
(ii) spreading out the sheet-like hair care product on the palmer side of a user's hand in such a manner that a part of the sheet-like hair care product hangs over the fingertips, and
(iii) moving the user's hand with the sheet-like hair care product thereon from the roots to the tips of hair strands to treat the hair strands.

[82] The method for treating hair according to clause [81], wherein the step (iii) is carried out by applying the user's fingertips with the sheet-like hair care product thereon to the roots or between the roots and tips of hair strands so as to get bunches of the hair strands in between adjacent fingers and combing the hair strands by the fingers.

[83] A method for treating hair using the sheet-like hair care product according to any one of clauses [1] to [79], including the steps of:
(i) when the sheet-like hair care product is held in a packaging container having an access opening, optionally picking up the sheet-like hair care product impregnated with the liquid cosmetic composition from the packaging container through the access opening,
(ii) spreading out the picked up sheet-like hair care product on the palmer side of a user's hand in such a manner that a part of the sheet-like hair care product hangs over the fingertips,
(iii) grasping a portion of hair in the form of a bunch by the hand having the sheet-like hair care product thereon, and
(iv) moving the hand having the bunch of hair grasped therein toward the end of the bunch of hair.

[84] A method for treating hair using the sheet-like hair care product according to any one of clauses [1] to [79], including the steps of:
(i) when the sheet-like hair care product is held in a packaging container having an access opening, optionally picking up the sheet-like hair care product impregnated with the liquid cosmetic composition from the packaging container through the access opening,
(ii) spreading out the picked up sheet-like hair care product on the palmer side of a user's hand in such a manner that a part of the sheet-like hair care product hangs over the fingertips,
(iii) taking out a portion of hair in the form of a bunch and holding the end of the bunch of hair and its vicinity in the hand with the sheet-like hair care product thereon, and
(iv) repeatedly opening and closing the hand having the bunch of hair therein to knead the hair strands of the bunch of hair.

[85] A method for cleaning scalp using the sheet-like hair care product according to any one of clauses [1] to [79], including the steps of:
(i) when the sheet-like hair care product is held in a packaging container having an access opening, optionally picking up the sheet-like hair care product impregnated with the liquid cosmetic composition from the packaging container through the access opening,
(ii) spreading out the picked up sheet-like hair care product on the palmer side of a user's hand in such a manner that a part of the sheet-like hair care product hangs over the fingertips, and
(iii) applying the fingertips of the hand the sheet-like hair care product thereon to the scalp and rubbing the fingers against the scalp in a to-and-fro vertical or horizontal motion.

[86] A method for cleaning scalp using the sheet-like hair care product according to any one of clauses [1] to [79], including the steps of:
when the sheet-like hair care product is held in a packaging container having an access opening, optionally picking up the sheet-like hair care product impregnated with the liquid cosmetic composition from the packaging container through the access opening,
(i) folding the sheet-like hair care product impregnated with the liquid cosmetic composition,
(ii) inserting user's fingers into the inside of the folded sheet-like hair care product to hold the sheet-like hair care product in the user's hand, and
(iii) applying the hand holding the sheet-like hair care product to the scalp and rubbing the fingertips against the scalp via the sheet-like hair care product.

EXAMPLES

The invention will now be shown in greater detail with reference to Examples, but it should be understood that the invention is not limited thereto. Unless otherwise noted, all the percents are by mass. The contents of ingredients in the liquid cosmetic compositions shown in Tables hereinafter given are active quantities in spite that the raw materials of the liquid cosmetic compositions are touched or not. Polysilicone-9 (1) and polysilicone-9 (2) used in Examples A to F were synthesized as follows.

Synthesis Example 1

Synthesis of Polysilicone 9-(1)

In 203.0 g of dry ethyl acetate were dissolved 19.0 g (0.12 mol) of diethyl sulfate and 81.0 g (0.82 mol) of 2-ethyl-2-oxazoline, and the solution was heated under reflux in a nitrogen atmosphere for 8 hours to synthesize terminal-reactive poly(N-propionylethyleneimine), the number average molecular weight of which was found by GPC to be 1100. To the product was added at once a 33% ethyl acetate solution of 300 g of branched primary aminopropyl-modified polydimethylsiloxane (weight average molecular weight: 32,000; amine equivalent: 2000), followed by heating under reflux for 10 hours. The reaction mixture was concentrated under reduced pressure to give 390 g (yield: 97%) of N-propionylethyleneimine-dimethylsiloxane copolymer as a pale yellow rubbery solid. The resulting product was found to have a silicone segment content of 75 mass % and a weight average molecular weight of 40,000. Neutralization titration with hydrochloric acid using methanol as a solvent revealed that about 20 mol % of amino group remained.

Synthesis Example 2

Synthesis of Polysilicone-9(2)

In 29 g of dry ethyl acetate were dissolved 0.8 g (0.005 mol) of diethyl sulfate and 12.8 g (0.14 mol) of 2-ethyl-2-oxazoline, and the solution was heated under reflux in a nitrogen atmosphere for 8 hours to synthesize terminal-reactive poly(N-propionylethyleneimine), the number average molecular weight of which was found by GPC to be 2700. To the product was added at once a 33% ethyl acetate solution of 100 g of branched primary aminopropyl-modified polydimethylsiloxane (weight average molecular weight: 100,000; amine equivalent: 20,000), followed by heating under reflux for 10 hours. The reaction mixture was concentrated under reduced pressure to yield 111 g (98%) of N-propionylethyleneimine-dimethylsiloxane copolymer as a pale yellow rubbery solid. The resulting product was found to have an organopolysiloxane segment content of 88 mass % and a weight average molecular weight of 114,000. Neutralization titration with hydrochloric acid using methanol as a solvent revealed that no amino group remained.

Examples A

Test of Spreadability, Fittability, and Liquid Cosmetic Composition Retentivity of Sheet Examples A1

(1) Preparation of Substrate Sheet
Substrate sheet A was prepared as follows.
A nonwoven fabric sheet 12 having the form shown in FIGS. 2 to 4 was made by a hydroentanglement process as follows. As described in Table 1 below, the nonwoven fabric sheet 12 was made of 70% rayon (2.2 dtex; fiber length: 38 mm) and 30% polyester fiber (2.2 dtex; fiber length: 38 mm) and had a basis weight of 60 g/m². The angle α between the extending direction of the ridges and grooves of the nonwoven fabric sheet 12 and the parallel opposite sides of the sheet 12 was 60°. The width W1 of each ridge was 2.0 mm. The width W2 of each groove was 3.2 mm. The thickness T was 1.2 mm. The height difference $D_a$ at the top of the ridge on the first side 21a was 0.7 mm, and the height difference $D_b$ of the ridge on the second side 21b was 0.2 mm. The distance L1 between adjacent perforations 24 was 6.3 mm. The individual perforations had a diameter L2 of 3 mm and an area of 7 mm². The diamond-shaped, perforated portion groups 30a forming the first perforated subregions 41a each had a dimension L3 in direction Y of 28 mm and a dimension L4 in direction X of 53 mm. The V-shaped, perforated portion groups 30b forming the second perforated subregions 41b each had a width W3 of 9 mm. One of the two diagonal portions of the V-shaped, perforated portion group 30b made an angle β of 30° with a straight line extending in direction X. One of the two diagonal portions of each V-shaped, non-perforated portion group 31a, which formed the first non-perforated subregion 42a, made an angle β of 30° with a straight line extending in direction X. The first non-perforated subregion 42a and the second non-perforated subregion 42b both had a width W4 of 8 mm. The nonwoven fabric sheet 12 had a size of 200 mm by 200 mm, a mass of 2.4 g, an overall basis weight of 60 g/m², the basis weight of the ridges was 84 g/m² and the basis weight of the grooves was 59 g/m².

(2) Preparation of Cosmetic Composition and Impregnation into Nonwoven Fabric Sheet A cosmetic composition was prepared according to the formulation shown in Table 2 below. The cosmetic composition prepared was infiltrated into the substrate sheet A prepared in (1) above in the amount shown in Table 3 below. The maximum water content shown in Table 3 was calculated by multiplying the maximum water retention determined by the method described below by the mass of the substrate sheet.

(3) Packaging in Packaging Container

A pillow bag made of a PET film having an aluminum deposit on the inner side was used as a packaging container. The shape of the packaging container was as shown in FIG. 1. The access opening of the packaging container was generally oblong rectangular with an area of 1200 mm² (40 mm by 30 mm). Five sheet-like hair care products prepared in (2) above were individually Z-folded to have a plan view area of 70 cm². A stack of the thus folded sheet-like hair care products was put in the packaging container in a manner such that the folded edge of the sheet-like hair care product might be seen through the access opening. A desired hair care product was thus obtained.

Example A2

A substrate sheet having the same fiber composition as the substrate sheet used in Example A1 was prepared in the same manner as in Example A1, except for changing the basis weight and the thickness (see Table 1). The resulting sheet had an overall basis weight of 45 g/m². The basis weight of the ridges was 63 g/mm² and the basis weight of the grooves was 44 g/m². A hair care product was made otherwise in the same manner as in Example A1.

Examples A3 to A5 and Comparative Examples A1 and A2

Substrate sheets were prepared using the fiber compositions and the process described in Table 1. Each of the substrate sheets was impregnated with the cosmetic composition shown in Table 2 in the amount shown in Table 3. Hair care products were made otherwise in the same manner as in Example A1.

Substrate sheet F had a three-dimensional textured surface shown in FIGS. 2 and 3 similarly to substrate sheet A. That is, the locations of the raised portions on the first side and those of the raised portions on the second side were substantially coincide with each other. The three-dimensional texture of substrate sheet C was such that the locations of the raised portions on the first side and those of the recessed portions on the second side were substantially coincide with each other, with no difference in basis weight between the recessed portions and the raised portions.

Method for Calculating Basis Weights of Raised Portions and Recessed Portions:

A 10 cm by 10 cm piece was cut out of the substrate sheet before impregnation of the cosmetic composition. The cut piece was cut into raised portions and recessed portions. The total mass (g) of the raised portions and the total mass (g) of the recessed portions were measured precisely to the tenth of a milligram. All the cutout raised portions of the substrate sheet were duplicated on a copier, and the image of the individual cutout raised portions were cut out from the copy. The total weight of the cutout pieces of the copy of individual raised portions was weighed precisely to the tenth of a milligram. A 10 cm by 10 cm square sheet of mounting paper was provided for use as a standard area sheet. The standard area sheet was copied, the image of the copy was cut out, and the cutout copy was weighed to the tenth of a milligram in the same manner as for the cutout raised portions. The total area of all the cutout raised portions was calculated from expression:

[Total area (m²) of all cutout raised portions]=
[weight (g) of all pieces cut out of the copy of raised portions]/[weight (g) of cut out copy of standard area sheet]/100.

Finally, the basis weight of the raised portions was calculated from expression:

[Basis weight (g/m²) of raised portions]=[total weight (g) of raised portions]/[total area (m²) of all cutout raised portions].

The same procedures were repeated for the recessed portions. That is, all cutout recessed portions of the nonwoven fabric sheet were copied, the images of the individual recessed portions were cut out of the copy, and the total weight of the cutout pieces of the copy was measured. The total area of all the cutout recessed portions was calculated from the ratio to the weight of the standard area sheet, from which the basis weight of the recessed portions was calculated.

Evaluation:

The hair care products obtained in Examples and Comparative Examples were evaluated in terms of bending resistance, thickness, and maximum water retention of the substrate sheet, spreadability of the sheet when taken out of the packaging container, fittability on fingers, cosmetic composition retentivity of the substrate sheet, delivery of the cosmetic composition to hair, ease of running fingers through hair in wiping operation, fixing effect on unruly hair (sticking-out hairs), ease of wiping scalp, and abrasion resistance during wiping operation according to the methods described below. The results of evaluation are shown in Tables 2 and 3.

Method of Evaluation:

(a) Bending Resistance, Thickness, and Maximum Water Retention of Substrate Sheet The substrate sheet before being impregnated with the cosmetic composition was used as a sample to be evaluated. Concrete methods are as follows.

(a-1) Bending Resistance

Bending resistance of sheet was measured by the 45° cantilever method in accordance with the following procedure, which is specified in JIS L1096:2010 ("Testing methods for woven and knitted fabrics", 8.21 Method A for bending resistance).

Measurement Procedures (i) Five specimens measuring 20 mm by about 150 mm were cut out of a sample sheet along each of direction Y and direction X. A cantilever softness tester having a horizontal platform with a smooth surface and a 45° slope face on one side thereof was used. The specimen was supported on the platform with one of its ends (short sides) even with the baseline of the scale.

(ii) The specimen was slowly slid towards the slope face using a motor at a constant speed (0.3 cm/sec). When the center of the leading edge of the specimen came in contact with the slope face, the moving distance of the tail end of the specimen was read on the scale. The bending resistance was expressed in terms of the moving distance (mm) of the specimen. The specimen was reversed and tested in the same manner. The specimens had been conditioned at 20° C. and 65% RH for 24 hours and then tested at 20° C. and 65% RH.

(iii) Measurement values for each of the longitudinal direction (machine direction) and the lateral direction (cross-machine direction) were averaged, and the average was rounded off to the closest whole number. Because the upper limit of the measuring range in this method was 110 mm, a specimen having an unmeasurable stiffness was regarded to have a bending resistance of 110 mm in the averaging.

(a-2) Thickness

The thickness of the substrate sheet before impregnation with the cosmetic composition was measured in accordance with JIS L1096:2010, "Method for measuring thickness of fabrics and textile products". A thickness gauge FS-60DS available from Daiei Kagaku Seiki was used. Measurement was taken on five specimens per sample with an area of 20 cm$^2$ after applying a load of 0.3 kPa to the specimen for 10 seconds using a pressure foot with a diameter of 50.5 mm. An average of the five measurement values was calculated.

(a-3) Maximum Water Retention

The maximum water retention was determined in accordance with the following procedures specified in JIS L1913: 2010, 6.9.2 "Test methods for nonwovens".

Measurement Procedures (i) Three specimens measuring 100 mm by 100 mm were cut out of a sample sheet and were each weighed to 1 mg.

(ii) About 1 liter of purified water was put in a 2-liter beaker, and the specimen was immersed therein for 15 minutes. The specimen was taken out of water by pinching one corner with tweezers, allowed to drain for 5 minutes without contacting with the wall of the beaker, and weighed to 1 mg.

(iii) The water retention was calculated from the following expression. The average was obtained as rounded off to the nearest tenth.

$$m=(m2-m1)/m1\times 100$$

wherein m is a water retention (%); m1 is the mass (mg) of the specimen in a standard state; and m2 is the mass (mg) of the specimen having been immersed in water and drained.

(b) Spreadability of Sheet when Taken out of Packaging Container

The sheet-like hair care product prepared in Examples and Comparative Examples as described in (1) and (2) above and packaged in the packaging container was taken out of the container through the access opening. The sheet was taken out by fingertips of a tester and spread out by shaking the wrist 5 times. The spread out sheet was placed on the palm in such a manner that a part of the sheet hangs over the fingertips. The spreadability of the sheet was rated by a panel of ten expert testers according to the following 1 to 5 scale. The scores by the ten testers were added up.

5: The sheet spreads out easily when taken out of the packaging container.
4: The sheet spreads out slightly easily when taken out of the packaging container.
3: The sheet hardly spreads out when taken out of the packaging container.
2: The sheet is able to be taken out from the packaging container but does not spread out due to clinging to itself
1: The sheet is unable to be taken out of the packaging container.

(c) Fittability over Fingers

The sheet-like hair care product prepared in (1) and (2) above and packaged in the packaging container as obtained in Examples and Comparative Examples was taken out of the container through the access opening and spread out on the palmer side of a tester's hand that was held horizontally in such a manner that a part of it hung over the fingertips. The hand with the sheet on was then raised vertically to make the sheet hang so as to cover the palmer and dorsal sides of the hand to evaluate "0° fittability". Then, the hand was held horizontally again, and the sheet on the hand was turned 45° clockwise, raised vertically in the same manner as above, and evaluated for "45° fittability". The same procedure was repeated after the sheet was turned 90° and 135° to evaluate "90° fittability" and "135° fittability". The common degree of fittability observed in the series of tests in varied directions of the sheet was rated according to the following scale. The evaluation was made by a panel of ten expert testers, and the scores given by them were added up.

5: The hanging sheet is in contact with the fingers.
4: The hanging sheet almost conforms to the shape of the fingers.
3: The hanging sheet conforms to the shape of the fingers but with a slight gap therebetween.
2: The hanging sheet conforms to the fingers but with a gap therebetween.
1: The sheet does not conform to the fingers.

(d) Cosmetic Composition Retentivity of the Substrate Sheet, Delivery of the Cosmetic Composition to Hair, Ease of Running Fingers Through Hair in Wiping Operation, and Fixing Effect on Unruly Hair (Sticking-out Hairs)

These performance properties were evaluated in treating hair as follows.

Each of the sheet-like hair care products of Examples and Comparative Examples was taken out of the packaging container and spread out on the palmer side of a tester's hand in such a manner that a part of it hung over the fingertips. The fingertips with the sheet on were applied to the roots of strands of hair at the top of the head in such a manner that bunches of hair strands got in between adjacent fingers and moved to the tip of the hair strands as if to comb with the fingers thereby to treat the hair. The similar hair treatment by finger combing was repeated five times at the same part of the head without changing the positions of the fingertips on the sheet.

(d-1) Cosmetic Composition Retentivity of Sheet

Liquid retentivity of the substrate sheet was evaluated by a panel of ten expert members in the above described hair treatment by finger combing. Evaluation was made according to the following scale, and the scores given by the panel were added up.

5: No drip is observed during use.
4: No drip is observed, but liquid drops sometimes spatter during use.
3: No drip is observed, but liquid drops often spatter during use.
2: Drip is observed during use.
1: Drip is observed before use.

(d-2) Delivery of Cosmetic Composition to Hair

Liquid delivery or transfer from the substrate sheet to hair was evaluated by a panel of ten expert testers in the above described hair treatment by finger combing. After the whole hair was treated, the state of the hair was scored according to the following scale, and the scores awarded by the panel were added up.

5: Thoroughly wet.
4: Wet to an insufficient extent.
3: Only partly wet.
2: Feels wet.
1: Not wet.

(d-3) Ease of Running Fingers Through Hair in Wiping Operation

The ease of wiping hair in the above described hair treatment by finger combing (referred to as "ease of finger combing" in Tables 3 and 4) was evaluated by a panel of ten expert testers and rated according to the following scale. The scores given by the panel were added up.
5: Easy
4: Slightly easy
3: Neither
2: Slightly difficult
1: Difficult (d-4) Fixing Effect on Unruly Hair (Sticking-out Hairs)

The above described hair treatment by finger combing was followed by combing with a paddle brush ten times to smooth out the hair. The wholehair was treated. After allowing the hair to dry spontaneously for 10 minutes, ease of fixing the unruly sticking-out hairs (referred to as "hair fixing properties" in Tables 3 and 4) was rated by a panel of ten expert testers according to the following rating scale. The scores by the testers were added up.
5: Fix unruly sticking-out hair easily
4: Fix unruly sticking-out hair slightly easily
3: Neither
2: Fix unruly sticking-out hair with slight difficulty
1: Fix unruly sticking-out hair with difficulty (e) Ease of Wiping Scalp and Abrasion Resistance of Sheet during Wiping Scalp (e-1) Ease of Wiping Scalp After the above described scalp treatment by wiping, the effect of the treatment in removing dirt on the scalp, such as sebum and sweat, was evaluated by a panel of ten expert testers according to the following scale. The scores awarded by the testers were added up.
5: The fingers sufficiently contact the scalp, and wiping the scalp is easy.
4: The fingers contact the scalp, and wiping the scalp is easy.
3: The fingers slightly contact the scalp and are able to wipe the scalp.
2: The fingers partly contact the scalp, and wiping the scalp is slightly difficult.
1: The fingers slightly contact the scalp and are unable to wipe the scalp.

(e-2) Abrasion Resistance in Wiping

The above described scalp treatment by wiping was repeated 35 more times (40 times in total). After that, the wear of the nonwoven fabric sheet was evaluated by a panel ten expert testers according to the following scale. The scores by the ten testers were added up.
5: The surface of the sheet shows no change.
4: The surface of the sheet shows slight twists of fibers.
3: The surface of the sheet shows twists of fibers.
2: The surface of the sheet shows fuzz or ravel.
1: The sheet breaks.

TABLE 1

Substrate Sheet

| | Evaluation Item | | | | | |
|---|---|---|---|---|---|---|
| | A | B | C | D | E | F |
| | Fiber Composition | | | | | |
| Process of Making | 70% rayon 30% PET hydroentanglement | 40% Tencel 50% hydrophilic PET 10% PP/PE hydroentanglement | 85% pulp 15% PET/PE (two-ply sheet) wet papermaking | 100% cotton hydroentanglement | 100% PET hydroentanglement | 70% rayon 30% PET hydroentanglement |
| Bending resistance (mm) | 42 | 50 | 74 | 35 | 33 | 34 |
| Basis Weight (g/m$^2$) | 60 | 45 | 56 | 30 | 90 | 45 |
| Max. Water Retention (%) | 1035 | 993 | 504 | 1245 | 574 | 1075 |
| Thickness @0.3 kPa (mm) | 1.19 | 0.54 | 0.28 | 0.29 | 0.92 | 0.89 |
| 3D Texture | yes | no | yes (embossing) | no | no | yes |
| Basis Weight of Raised Portions (g/m$^2$) | 84 | — | — | — | — | 63 |
| Basis Weight of Recessed Portions (g/m$^2$) | 59 | — | — | — | — | 44 |
| Perforation Size (mm$^2$) | 7 | 0.2 | non-perforated | 0.75 | non-perforated | 7 |

These performance properties were evaluated through hair treatment carried out as follows.

The sheet-like hair care product of Examples and Comparative Examples was taken out of the packaging container and spread out on the palmer side of a tester's hand in such a manner that a part of it hung over the fingertips. The fingertips with the sheet-like hair care product thereon were applied to the scalp along the hairline at the nape of the neck, and the hand was moved generally toward the top of the head while moving the fingers shortly to-and-fro horizontally to wipe the scalp. This treatment operation was repeated five times without changing the positions of the fingertips on the sheet.

TABLE 2

| Ingredient | Content (%) |
|---|---|
| Ethanol | 20.0 |
| Dipropylene glycol | 1.0 |
| Polyoxyethylene (60) hydrogenated castor oil[*1] | 1.0 |
| Polyoxyethylene (9) C12-14 alkyl ether[*2] | 0.20 |
| Ceteareth-7 | 0.028 |
| Ceteareth-25 | 0.006 |
| Cetyltrimethylammonium chloride[*3] | 0.24 |
| Polysilicone-9(2) | 0.30 |
| Amodimethicone | 0.14 |

TABLE 2-continued

| Ingredient | Content (%) |
|---|---|
| Methyl paraben | 0.15 |
| 2-Amino-2-hydroxymethyl-1,3-propanediol | 0.10 |
| C-Menthol | 0.05 |
| Lactic acid | 0.09 |
| Phenoxyethanol | 0.002 |
| Fragrance | 0.1 |
| Water | balance |
| Total | 100.0 |
| pH | 7 |

Note that *1 to *3 in Table 2 are as follows.
*[1]Emanon CH-60, from Kao Corp.
*[2]Softanol 90, from Kao Corp.
*[3]Quartamin 60W, from Kao Corp.

TABLE 3

| | Example A1 | Example A2 | Example A3 | Comp. Example A1 | Example A4 | Example A5 | Comp. Example A2 |
|---|---|---|---|---|---|---|---|
| Substrate Sheet | A | F | B | C | A | D | E |
| Size of substrate sheet (cm$^2$) | 400 | 400 | 400 | 400 | 400 | 600 | 267 |
| Mass of substrate sheet (g/sheet) | 2.4 | 1.8 | 1.8 | 2.2 | 2.4 | 1.8 | 2.4 |
| Max. Water Content | 24.8 | 19.4 | 17.9 | 11.1 | 24.8 | 22.4 | 13.8 |
| Amount of Cosmetic Composition (g) | 9.6 | 9.6 | 9.6 | 8.5 | 14.0 | 7.2 | 9.6 |
| Ratio of Cosmetic Composition to Max. Water Content | 39% | 50% | 54% | 77% | 56% | 32% | 70% |
| Sheet Spreadability when taken out of packaging container | 49 | 48 | 49 | 47 | 45 | 27 | 21 |
| Fittability on hand | 47 | 48 | 48 | 23 | 48 | 48 | 10 |
| Cosmetic Composition Retentivity of sheet | 48 | 47 | 41 | 45 | 40 | 48 | 38 |
| Delivery of Cosmetic Composition to Hair | 45 | 47 | 48 | 28 | 46 | 42 | 24 |
| Ease of Finger Combing | 48 | 49 | 42 | 14 | 42 | 47 | 10 |
| Hair Fixing Properties | 47 | 48 | 48 | 22 | 47 | 44 | 17 |
| Ease of Wiping Scalp | 45 | 47 | 47 | 18 | 46 | 48 | 14 |
| Abrasion Resistance in Wiping | 45 | 41 | 39 | 43 | 42 | 18 | 50 |

As is apparent from the results in Table 3, the hair care products of Examples proved to spread out more easily when taken out of the packaging container and exhibit better fittability on the hand and fingers than those of Comparative Examples. The sheet-like hair care products of Examples also proved excellent in cosmetic composition retentivity and smooth transfer of the cosmetic composition to the hair, easy to glide on hair strands in finger combing, and capable of fixing unruly, sticking-out hairs. Furthermore, they also proved easy to use in wiping the scalp therewith and highly resistant to abrasion in wiping operation.

Examples A6 to A24

The same substrate sheet as used in Example A1 was impregnated with each of the cosmetic compositions shown in Table 4 below in the same amount as in Example A1. A hair care product was obtained otherwise in the same manner as in Example A1 and evaluated in the same manner as in Example A1. The results obtained are shown in Table 4.

TABLE 4

| Formulation of Cosmetic | | Example A | | | | | | | | | |
|---|---|---|---|---|---|---|---|---|---|---|---|
| Composition (mass %) | | 6 | 7 | 8 | 9 | 10 | 11 | 12 | 13 | 14 | 15 | 16 |
| Ethanol | | 30 | 20 | 20 | 20 | 20 | 20 | 20 | 20 | 13 | | 20 |
| Isopropyl alcohol | | | | | | | | 1 | | | 10 | |
| Glycerol | | | | | | | | | 1 | | | |
| Propylene glycol | | | | | | | | | | 8 | | |
| 1,3-Butanediol | | | | | | | | | | | 11 | |
| Diglycerol | | | | | | | | | | | | 1 |
| Ethoxydiglycol | | | | | | | | | | | | |
| Dipropylene glycol | | | 1 | 1 | 1 | 1 | 1 | | | | | |
| Anionic surfactant | Ammonium laureth sulfate*4 | | 1.44 | | | | | | | | | |
| Canionic surfactant | Cetrimonium chloride*3 | | | 1.44 | | | | 2.4 | 0.24 | 0.24 | 0.24 | 0.24 |

TABLE 4-continued

| | | | | | | | | | | | | |
|---|---|---|---|---|---|---|---|---|---|---|---|---|
| Nonionic surfactant | Polyoxyethylene(9) C12-14 alkyl ether*2 | | | | 1.44 | 2.6 | 0.2 | 0.2 | 0.2 | 0.2 | 0.2 | |
| | Polyoxyethylene(60) hydrogenated castor oil*1 | 0.2 | | | | | 0.75 | 0.75 | 0.75 | 0.75 | 0.75 | |
| | Polyoxyethylene(40) cetyl ether*5 | | | | | | 0.25 | 0.25 | 0.25 | 0.25 | 0.25 | |
| Amphoteric surfactant | Lauramidopropyl betaine*6 | | | | 1.44 | | | | | | | |
| | Polysilicone-9(1) | | 0.01 | 0.01 | 0.01 | 0.01 | 0.01 | 0.03 | 0.01 | 0.01 | 0.01 | 0.01 |
| | Polysilicone-9(2) | | 0.25 | 0.25 | 0.25 | 0.25 | 0.25 | 0.83 | 0.25 | 0.25 | 0.25 | 0.25 |
| | Amodimethicone | | 0.14 | 0.14 | 0.14 | 0.14 | 0.14 | 0.35 | 0.14 | 0.14 | 0.14 | 0.14 |
| Acrylates/C10-30 alkyl acrylate crosspolymer*7 | | 0.04 | | | | | | | | | | |
| | C-Menthol | 0.2 | 0 | 0 | 0 | 0 | 0 | 0 | 0 | 0 | 0 | 0 |
| | EDTA-2Na | | 0.05 | 0.05 | 0.05 | 0.05 | 0.05 | 0.05 | 0.05 | 0.05 | 0.05 | 0.05 |
| | Methyl p-hydroxybenzoate | 0.2 | 0 | 0 | 0 | 0 | 0 | 0 | 0 | 0 | 0 | 0 |
| | Tromethamine | | 0.2 | 0.2 | 0.2 | 0.2 | 0.2 | 0.2 | 0.2 | 0.2 | 0.2 | 0.2 |
| | Lactic acid | | 0.08 | 0.08 | 0.08 | 0.08 | 0.08 | 0.08 | 0.08 | 0.08 | 0.08 | 0.08 |
| | Fragrance | | 0.08 | 0.08 | 0.08 | 0.08 | 0.08 | 0.08 | 0.08 | 0.08 | 0.08 | 0.08 |
| | AMP | 0.0011 | | | | | | | | | | |
| | Purified water | | | | | balance | | | | | | |
| | Total | 100 | 100 | 100 | 100 | 100 | 100 | 100 | 100 | 100 | 100 | 100 |
| | Spreadability | 48 | 48 | 49 | 49 | 47 | 46 | 49 | 48 | 49 | 48 | 49 |
| | Fittability over fingers | 47 | 48 | 48 | 47 | 47 | 47 | 49 | 47 | 48 | 47 | 47 |
| | Cosmetic composition Retentivity | 49 | 49 | 48 | 48 | 49 | 49 | 49 | 49 | 48 | 49 | 47 |
| | Delivery of cosmetic composition to hair | 45 | 43 | 46 | 41 | 40 | 45 | 44 | 45 | 43 | 42 | 46 |
| | Ease of finger combing | 43 | 39 | 49 | 42 | 38 | 46 | 48 | 43 | 49 | 45 | 47 |
| | Hair fixing properties | 39 | 39 | 41 | 45 | 42 | 40 | 46 | 41 | 44 | 45 | 46 |
| | Ease of wiping scalp | 45 | 41 | 45 | 44 | 41 | 40 | 45 | 43 | 45 | 46 | 45 |
| | Abrasion resistance in wiping | 46 | 43 | 46 | 42 | 43 | 42 | 45 | 46 | 46 | 45 | 45 |

| Formulation of Cosmetic | | Example A | | | | | | | |
|---|---|---|---|---|---|---|---|---|---|
| Composition (mass %) | | 17 | 18 | 19 | 20 | 21 | 22 | 23 | 24 |
| | Ethanol | 20 | | | 20 | 20 | 20 | 20 | 20 |
| | Isopropyl alcohol | | 20 | | 2 | | | | |
| | Glycerol | | | | 2 | | | | |
| | Propylene glycol | | | | 2 | | | | |
| | 1,3-Butanediol | | | 1 | 15 | | | | |
| | Diglycerol | | | | 2 | | | | |
| | Ethoxydiglycol | 1 | | | 2 | | | | |
| | Dipropylene glycol | | 1 | | | 1 | 1 | 1 | 1 |
| Anionic surfactant | Ammonium laureth sulfate*4 | | | | | 0.24 | | | 0.24 |
| Canionic surfactant | Cetrimonium chloride*3 | 0.24 | 0.24 | 0.24 | | | | 0.07 | |
| Nonionic surfactant | Polyoxyethylene(9) C12-14 alkyl ether*2 | 0.2 | 0.2 | 0.2 | 0.2 | 0.2 | | | |
| | Polyoxyethylene(60) hydrogenated castor oil*1 | 0.75 | 0.75 | 0.75 | 0.75 | 0.75 | | | |
| | Polyoxyethylene(40) cetyl ether*5 | 0.25 | 0.25 | 0.25 | 0.25 | 0.25 | | | |

TABLE 4-continued

| | | | | | | | | | |
|---|---|---|---|---|---|---|---|---|---|
| Amphoteric surfactant | :Lauramidopropyl betaine*6 | | | | | | 0.24 | 1.2 | 1.2 |
| | Polysilicone-9(1) | 0.01 | 0.01 | | 0.01 | 0.03 | 0.01 | 0.01 | 0.03 |
| | Polysilicone-9(2) | 0.25 | 0.25 | | 0.25 | 0.83 | 0.25 | 0.25 | 0.83 |
| | Amodimethicone | 0.14 | 0.14 | 0.14 | 0.14 | 0.35 | 0.14 | 0.14 | 0.14 |
| | Acrylates/C10-30 alkyl acrylate crosspolymer*7 | | | | | | | | |
| | C-Menthol | 0 | 0 | 0 | 0 | 0 | 0 | 0 | 0 |
| | EDTA-2Na | 0.05 | 0.05 | 0.05 | 0.05 | 0.05 | 0.05 | 0.05 | 0.05 |
| | Methyl p-hydroxybenzoate | 0 | 0 | 0 | 0 | 0 | 0 | 0 | 0 |
| | Tromethamine | 0.2 | 0.2 | 0.2 | 0.2 | 0.2 | 0.2 | 0.2 | 0.2 |
| | Lactic acid | 0.08 | 0.08 | 0.08 | 0.08 | 0.08 | 0.08 | 0.08 | 0.08 |
| | Fragrance | 0.08 | 0.08 | 0.08 | 0.08 | 0.08 | 0.08 | 0.08 | 0.08 |
| | AMP | | | | | | | | |
| | Purified water | balance | | | | | | | |
| | Total | 100 | 100 | 100 | 100 | 100 | 100 | 100 | 100 |
| | Spreadability | 49 | 49 | 47 | 47 | 48 | 49 | 49 | 47 |
| | Fittability over fingers | 48 | 49 | 47 | 48 | 48 | 49 | 48 | 47 |
| | Cosmetic composition Retentivity | 49 | 49 | 48 | 46 | 48 | 47 | 48 | 49 |
| | Delivery of cosmetic composition to hair | 45 | 46 | 43 | 48 | 43 | 44 | 42 | 41 |
| | Ease of finger combing | 46 | 47 | 45 | 46 | 38 | 39 | 40 | 39 |
| | Hair fixing properties | 46 | 43 | 46 | 41 | 39 | 41 | 42 | 40 |
| | Ease of wiping scalp | 47 | 46 | 42 | 40 | 40 | 42 | 41 | 41 |
| | Abrasion resistance in wiping | 46 | 45 | 45 | 45 | 43 | 45 | 44 | 42 |

Note that *1 to *7 in Table 4 are as follows.
*1: Emanon CH-60, from Kao
*2: Softanol 90, from Kao
*3: Quartamin 60W, from Kao
*4: Emal 125A, from Kao
*5: Nikkol BC-40TX, from Nihon Surfactant Kogyo K.K.
*6: Amphitol 20AB, from Kao
*7: Carbopol ETD2020, from Lubrizol Advanced Materials Substrate sheets that representatively exhibited excellent effects were chosen from those evaluated in Examples A and further subjected to tests in Examples B through F to evaluate additional effects obtainable by altering the formulation of the liquid cosmetic composition.

Examples B

Test on Sticky Feel and Unpleasant Feeling of Film-forming Resin

Example B1

The N-propionylpolyethyleneimine-methylpolysiloxane copolymer described in Tables 5, 7, and 8 below was the polymer synthesized in Synthesis Example 2.
(1) Preparation of Substrate Sheet
Substrate sheet A used in Example A1 was used.
(2) Preparation of Cosmetic Composition and Impregnation into Nonwoven Fabric Sheet
A hair cosmetic composition was prepared in a usual manner according to the formulation shown in Table 5. The resulting cosmetic composition was infiltrated into the substrate sheet in the amount shown in Table 6.
(3) Packaging in a Packaging Container
The sheet-like hair care products were packaged in a packaging container in the same manner as in Example A1.

Examples B2 to B4 and Comparative Examples B1 and B2

Sheet-like hair care products were made in the same manner as in Example B1, except for changing the amount of the cosmetic composition to be infiltrated and the size of the substrate sheet as shown in Table 6.
Evaluation:
The sheet-like hair care products obtained in Examples and Comparative Examples were tested for bending resistance, thickness, and maximum water retention in the same manner as in Example A1. The sheet-like hair care products were evaluated in terms of scratch hardness (by pencil test) of the film-forming resin, ease of delivery of the cosmetic composition to hair, freedom from drip from the sheet, freedom from sticky feeling on hand and fingers during use of the hairstyling cosmetic product, freedom from unpleasant feeling due to a residue of the cosmetic composition after use of the hairstyling cosmetic product, and hair fixing performance after drying. The results are shown in Tables 5 and 6.
(a) Scratch Hardness (by Pencil Test) of Film-forming Resin
The scratch hardness was determined in accordance with JIS 5600-5-4:1999, "Testing methods for paints—scratch hardness (Pencil method)". The coating to be tested was prepared by applying 2 g of a 10 mass % ethanolic solution of the film-forming resin over an area of 3 cm by 4 cm of a PET film, followed by drying at 25° C. and 50% RH for at least 24 hours. A pencil was pushed to the coating at a fixed angle of 45 degrees and constant load of 750 g to determine the scratch hardness (by pencil test).
(b) Ease of Delivery of Cosmetic Composition to Hair
The sheet-like hair care products of Examples and Comparative Examples were taken out of the packaging container and each spread out on the palmer side of a tester's hand in such a manner that a part of it hung over the fingertips. The fingertips with the sheet on were applied to the roots of a handful of hair strands at the top of the head in such a manner that bunches of hair strands got in between adjacent fingers and moved to the tip of the hair strands as if to comb with the fingers thereby to treat the hair. The delivery or transfer of the liquid cosmetic composition to the handful of hair strands treated in the above operation was rated by a panel of ten testers as to whether the hair strands were thoroughly wetted from roots to tips according to the following scale. The scores awarded were added up.

5: Thoroughly wet
4: Wholly wet but to an insufficient extent
3: Only partly wet
2: Feels wet
1: Not wet (c) Freedom from Drip Liquid retentivity of the substrate sheet was evaluated by a panel of ten testers in the above described hair treatment by finger combing according to the following scale. The scores given by the panel were added up.

5: No drip is observed during use.
4: No drip is observed, but liquid drops sometimes spatter during use.
3: No drip is observed, but liquid drops often spatter during use.
2: Drip is observed during use.
1: Drip is observed before use.

(d) Freedom from Sticky Feel on Hand and Fingers during Use of Sheet-like Hair Care Product The sticky feel of the hand and fingers during and after the above described hair treatment by finger combing was evaluated by a panel of ten testers in according to the following rating scale. The scores given by the panel were added up.

5: Not sticky during and after use
4: Slightly not sticky during and after use
3: Slightly sticky during use and slightly not sticky after use
2: Slightly sticky during and after use
1: Sticky during and after use (e) Freedom from Unpleasant Feeling due to Residue of Cosmetic Composition after Use of Sheet-like Hair Care Product After the above described hair treatment by finger combing and after the hand and fingers dried, an unpleasant feeling of the hand and fingers due to residue of the cosmetic composition left thereon was rated by ten testers according to the following scale. The scores were added up.

5: No feeling of residue after use, causing no unpleasant feeling.
4: Slightly no feeling of residue after use, causing no unpleasant feeling.
3: Slight feeling of residue after use, not causing an unpleasant feeling.
2: Feeling of residue after use, causing an unpleasant feeling.
1: Heavy feeling of residue after use, causing an unpleasant feeling.

(f) Hair Fixing Properties after Drying of Cosmetic Composition

After the above described hair treatment by finger combing and after allowing the treated hair to dry spontaneously for 5 minutes, the manageability of unruly hair having sticking-out hairs or flyaway hairs was evaluated by a panel of ten testers according to the following scale. The scores awarded by the testers were added up.

5: Manageable to tame sticking-out hairs.
4: Slightly manageable to tame sticking-out hairs.
3: Slightly manageable but not to tame sticking-out hairs.
2: Slightly unmanageable not to tame sticking-out hairs.
1: Unmanageable not to tame sticking-out hairs.

TABLE 5

| Ingredient | Content (%) |
| --- | --- |
| Cationic film-forming resin: N-propionylpolyethyleneimine-methylpolysiloxane copolymer[*1] | 0.3 |
| Ethanol | 20.0 |
| Dipropylene glycol | 1.0 |
| Cetrimonium chloride[*2] | 0.24 |
| Polyoxyethylene (9) C12-14 alkyl ether[*3] | 0.20 |
| Polyoxyethylene (60) hydrogenated castor oil[*4] | 0.75 |
| Polyoxyethylene (40) cetyl ether[*5] | 0.25 |
| EDTA-Na | 0.05 |
| tromethamine | 0.20 |
| Lactic acid | 0.08 |
| Water | balance |
| Total | 100.0 |

Note that *1 to *5 in Table 5 are as follows.
[*1] Polysilicone-9 (2) synthesized in Synthesis Example 2
[*2] Quartamin 60W, from Kao
[*3] Softanol 90, from Kao
[*4] Emanon CH-60, from Kao
[*5] Nikkol BC-40TX, from Nikko Chemicals

TABLE 6

| | Example B1 | Example B2 | Example B3 | Example B4 | Comp. Example B1 | Comp. Example B2 |
| --- | --- | --- | --- | --- | --- | --- |
| Size (cm$^2$)of Substrate Sheet | 400 | 900 | 1225 | 64 | 64 | 1225 |
| Mass of Substrate Sheet (g/sheet) | 2.4 | 5.4 | 7.4 | 0.4 | 0.4 | 7.4 |
| Max. Water Content | 24.8 | 55.8 | 76.0 | 4.0 | 4.0 | 76.0 |
| Amount of Cosmetic Composition (g) | 10 | 30 | 45 | 1.0 | 0.5 | 60.0 |
| Ratio of Cosmetic Composition to Max. Water content | 40% | 54% | 60% | 25% | 13% | 79% |
| Pencil Hardness of Coating of Film-forming Resin | 6B | 6B | 6B | 6B | 6B | 6B |
| Freedom from Sticky Feel of Hand & Fingers during Use of Hairstyling Cosmetic Product | 48 | 46 | 44 | 49 | 49 | 42 |
| Freedom from Unpleasant Feeling of Residue of Cosmetic Composition after Use of Hairstyling Cosmetic Product | 47 | 46 | 45 | 49 | 49 | 39 |
| Hair Fixing Properties after Drying | 47 | 48 | 46 | 45 | 35 | 38 |
| Ease of Delivery of Cosmetic Composition to Hair | 45 | 47 | 48 | 40 | 23 | 49 |
| Freedom from Drip from Sheet | 48 | 44 | 40 | 49 | 50 | 21 |

As is apparent from the results in Table 6, the sheet-like hair care products obtained in Examples cause little sticky feel on the hand and fingers during use and little unpleasant feeling due to a residue of the cosmetic composition on the hand and fingers after use. The sheet-like hair care product of Examples also prove to provide excellent hair fixing effect after the cosmetic composition dries. Furthermore, as is obvious from the comparison between Examples B1 through B4 and Comparative Examples B1 to B2, the cosmetic composition is smoothly delivered to hair without drip from the substrate sheet by properly adjusting the amount of the liquid cosmetic composition to be infiltrated into the substrate sheet.

Examples B5 to B23

A substrate sheet used in Example B1 was used, and a cosmetic composition shown in FIG. 7 was infiltrated into the substrate sheet in the same amount as used in Example B1. A hair care product was made otherwise in the same manner as in Example E1. The resulting products were evaluated in the same manner as in Example B1. The results of evaluation are shown in Table 7.

TABLE 7

| Formulation of Cosmetic Composition (mass %) | | 5 | 6 | 7 | 8 | 9 | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|---|---|---|---|---|
| Cationic film-forming resin | N-propionylpolyethyleneimine-methylpolysiloxane copolymer*1 | 5 | 7.5 | 10 | 15 | 20 | — | — | — | — | — | — | — | — | — | — | — | — | — | — |
| | poly(dimethylmethylenepiperidinium chloride)*6 | — | — | — | — | — | 0.5 | — | — | — | — | — | — | — | — | — | — | — | — | — |
| | ammonium-modified hydroxyethyl cellulose*7 | — | — | — | — | — | — | 0.5 | — | — | — | — | — | — | — | — | — | — | — | — |
| | vinylpyrrolidone-N,N-dimethylaminoethyl methacrylate copolymer diethylsulfate*8 | — | — | — | — | — | — | — | 0.1 | — | — | — | — | — | — | — | — | — | — | — |
| | N,N-dimethylaminoethyl methacrylate diethylsulfate-N,N-dimethylacrylamide-polyethylene glycol dimethacrylate copolymer*9 | — | — | — | — | — | — | — | — | 0.1 | — | — | — | — | — | — | — | — | — | — |
| Nonionic film-forming resin | vinyl methyl ether-alkyl maleate copolymer*10 | — | — | — | — | — | — | — | — | — | 0.1 | — | — | — | — | — | — | — | — | — |
| | vinylpyrrolidone-vinyl acetate copolymer*11 | — | — | — | — | — | — | — | — | — | — | 1.5 | — | — | — | — | — | — | — | — |
| | polyvinylpyrrolidone*12 | — | — | — | — | — | — | — | — | — | — | — | 3 | — | — | — | — | — | — | — |
| Amphoteric film-forming resin | methacryloyloxyethylcarboxybetaine-alkyl methacrylate copolymer*13 | — | — | — | — | — | — | — | — | — | — | — | — | 0.03 | — | — | — | — | — | — |
| | acrylates-lauryl acrylate-stearyl acrylate-ethylamine oxide methacrylate copolymer*14 | — | — | — | — | — | — | — | — | — | — | — | — | — | 2 | — | — | — | — | — |
| | octylacrylamide-hydroxypropyl acrylate-butylaminoethyl methacrylate copolymer*15 | — | — | — | — | — | — | — | — | — | — | — | — | — | — | 3.4 | — | — | — | — |
| Anionic film-forming resin | alkyl acrylate-diacetoneacrylamide copolymer*16 | — | — | — | — | — | — | — | — | — | — | — | — | — | — | — | 0.1 | — | — | — |
| | vinyl acetate-crotonic acid-vinyl neodecanoate copolymer*17 | — | — | — | — | — | — | — | — | — | — | — | — | — | — | — | — | 0.45 | — | — |
| Non-film-forming resin: (acrylates/C10-30 alkyl acrylate) crosspolymer*19 | 4,4′-isopropylidenediphenol copolymer*18 | — | — | — | — | — | — | — | — | — | — | — | — | — | — | — | — | — | 0.45 | 0.04 |
| | Ethanol | 30 | 30 | 30 | 30 | 28 | 20 | 30 | 20 | 20 | 20 | 20 | 20 | 20 | 20 | 40 | 20 | 30 | 20 | 30 |
| | Dipropylene glycol | 1 | 1 | 1 | 1 | 1 | 1 | 1 | 1 | 1 | 1 | 1 | 1 | 1 | 1 | 1 | 1 | 1 | 1 | — |
| | Cetrimonium chloride*2 | 0.24 | 0.24 | 0.24 | 0.24 | 0.24 | 0.24 | 0.24 | 0.24 | 0.24 | 0.24 | 0.24 | 0.24 | 0.24 | 0.24 | 0.24 | 0.24 | 0.24 | 0.24 | — |
| | Polyoxyethylene (9) C12-14 alkyl ether*3 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | — |
| | Polyoxyethylene (60) hydrogenated castor oil*4 | 0.75 | 0.75 | 0.75 | 0.75 | 0.75 | 0.75 | 0.75 | 0.75 | 0.75 | 0.75 | 0.75 | 0.75 | 0.75 | 0.75 | 0.75 | 0.75 | 0.75 | 0.75 | 0.2 |
| | Polyoxyethylene (40) cetyl ether*5 | 0.25 | 0.25 | 0.25 | 0.25 | 0.25 | 0.25 | 0.25 | 0.25 | 0.25 | 0.25 | 0.25 | 0.25 | 0.25 | 0.25 | 0.25 | 0.25 | 0.25 | 0.25 | — |
| | EDTA-2Na | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | 0.05 | — |
| | Tromethamine | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 | — |
| | Lactic acid | 0.08 | 0.08 | 0.08 | 0.08 | 0.08 | 0.08 | 0.08 | 0.08 | 0.08 | 0.08 | 0.08 | 0.08 | 0.08 | 0.08 | 0.08 | 0.08 | 0.08 | 0.08 | — |
| | Amodimethicone | — | — | — | — | — | — | — | — | — | 0.14 | 0.14 | 0.14 | 0.14 | 0.14 | 0.14 | 0.14 | 0.14 | — | — |
| | AMP | — | — | — | — | — | — | — | — | — | 0.18 | — | — | — | — | 0.55 | — | — | — | 0.001 |

TABLE 7-continued

| Formulation of Cosmetic Composition (mass %) | Example B | | | | | | | | | | | | | | | | | | |
|---|---|---|---|---|---|---|---|---|---|---|---|---|---|---|---|---|---|---|---|
| | 5 | 6 | 7 | 8 | 9 | 10 | 11 | 12 | 13 | 14 | 15 | 16 | 17 | 18 | 19 | 20 | 21 | 22 | 23 |
| Purified water | balance | | | | | | | | | | | | | | | | | | |
| Total | 100 | 100 | 100 | 100 | 100 | 100 | 100 | 100 | 100 | 100 | 100 | 100 | 100 | 100 | 100 | 100 | 100 | 100 | 100 |
| Pencil hardness of film-forming resin coating | 6B | 6B | 6B | 6B | 6B | 2B | HB | F | 6B | H | H | H | 3H | 6B | 3H | H | H | F | Coating-non-formed |
| Freedom from sticky feel of hand and fingers during use of hairstyling product | 35 | 37 | 34 | 32 | 30 | 39 | 44 | 42 | 47 | 44 | 40 | 37 | 46 | 37 | 31 | 42 | 37 | 45 | 46 |
| Freedom from unpleasant feeling of hand and fingers after use of hairstyling product and after drying | 37 | 35 | 34 | 30 | 30 | 46 | 44 | 45 | 48 | 46 | 39 | 36 | 48 | 40 | 39 | 46 | 40 | 45 | 47 |
| Hair fixing properties after drying | 46 | 46 | 46 | 47 | 47 | 43 | 42 | 43 | 41 | 44 | 47 | 49 | 40 | 43 | 47 | 40 | 43 | 42 | 22 |
| Ease of delivery of cosmetic composition to hair | 48 | 48 | 47 | 45 | 45 | 49 | 49 | 50 | 49 | 50 | 48 | 48 | 49 | 48 | 47 | 50 | 49 | 48 | 49 |
| Freedom from drip from sheet | 49 | 49 | 48 | 47 | 46 | 48 | 47 | 46 | 49 | 48 | 49 | 49 | 48 | 47 | 47 | 49 | 48 | 47 | 47 |

Note that *1 to *19 in Table 7 are as follows.
*1: Polysilicone-9 (2) synthesized in Synthesis Example 2
*2: Quartamin 60W, from Kao Corp.
*3: Softanol 90, from Kao
*4: Emanon CH-60, from Kao
*5: Nikkol BC-40TX, from Nikko Chemicals
*6: Marquat 550, from Nalco Co.
*7: SofCat SL-30 polymer, from Kao
*8: Gafquat 734, from ISP
*9: Sofcare KG-101W-E, from Kao
*10: Gantrez ES-225, from ISP
*11: Luviskol VA73E, from BASF
*12: Lubiskol K90, from BASF
*13: Yukaformer M75, from Mitsubishi Chemical
*14: Diaformer Z651, from Mitsubishi Chemical
*15: Amphomer 28-4910, from Akzo Nobel
*16: Plascize L-9540B, from Goo Chemical Co., Ltd.
*17: RESYN 28-2930, from Akzo Nobel
*18: DynamX, from Akzo Nobel
*19: Carbopol ETD2020, from Lubrizol Advanced Material

Examples B24 to B28

Out of the cosmetic composition-impregnated substrate sheets shown in Table 5, representative samples were chosen and further evaluated in terms of ease of glide between the sheet and hair during use of the hair care product, a clean feeling of hair being cleaned during use of the hair care product, a moist and soft feel of hair after use of the hair care product, the body and bounce of hair after use of the hair care product, and a hair bunch texture of hair after use of the hair care product in accordance with the methods described below.

(a) Glide between Hair and the Sheet during Use of the Sheet-like Hair Care Product In treating hair by finger combing, the smoothness of the glide of the sheet on hair was evaluated by a panel of ten testers and rated according to the following scale in comparison with the same substrate sheet as used in Example B1 that was impregnated with the same amount as in Example B1 of ion-exchanged water. The scores awarded by the testers were added up.
5: Glide more easily than water-impregnated-sheet
4: Glide slightly more easily than water-impregnated-sheet
3: Glide equally to water-impregnated-sheet
2: Glide slightly harder than water-impregnated-sheet
1: Glide harder than water-impregnated-sheet (b) Clean Feeling of Hair during Use of Sheet-like Hair Care Product In treating hair by finger combing, the clean feeling of hair during the treatment was evaluated by a panel of ten testers and rated in comparison with the same substrate sheet as used in Example B1 that was impregnated with the same amount as used in Example B1 of ion-exchanged water according to the following scale. The scores awarded by the panel were added up.
5: Cleaner feeling than water-impregnated-sheet
4: Slightly cleaner feeling than water-impregnated-sheet
3: Equal to water-impregnated-sheet
2: Slightly less clean feeling than water-impregnated-sheet
1: Less clean feeling than water-impregnated-sheet (c) Moist and Soft Feel of Hair after Use of Sheet-like Hair Care Product After treating hair by finger combing, the moist and soft feel of the treated hair after the hair dried was evaluated and rated by a panel of ten testers in comparison with the same substrate sheet as used in Example B1 that was impregnated with the same amount as used in Example B1 of ion-exchanged water according to the following scale. The scores awarded by the panel were added up.
5: Moister and softer than water-impregnated-sheet
4: Slightly moister and softer than water-impregnated-sheet
3: Equal to water-impregnated-sheet
2: Slightly less moist and less soft than water-impregnated-sheet
1: Less moist and less soft than water-impregnated-sheet (d) Body and Bounce of Hair after Use of Sheet-like Hair Care Product After hair was treated by finger combing, and after the treated hair dried, the body and bounce of the hair was evaluated and rated by a panel of ten testers in comparison with the same substrate sheet as used in Example B1 that was impregnated with the same amount as used in Example B1 of ion-exchanged water according to the following scale. The scores awarded by the panel were added up.
5: Improved body and bounce compared with water-impregnated-sheet
4: Slightly improved body and bounce compared with water-impregnated-sheet
3: Equal body and bounce to water-impregnated-sheet
2: Slightly less improved body and bounce compared with water-impregnated-sheet
1: Not improved body and bounce compared with water-impregnated-sheet (e) Hair Bunch Texture of Hair after Use of Sheet-like Hair Care Product After the hair treatment by finger combing and after drying the treated hair dried, the hair bunch texture of hair was evaluated by a panel of ten testers in comparison with the same substrate sheet as used in Example B1 that was impregnated with the same amount as used in Example B1 of ion-exchanged water according to the following scale. The scores awarded by the testers were added up.
5: Wispier compared with water-impregnated-sheet
4: Slightly wispier compared with water-impregnated-sheet
3: Equal to water-impregnated-sheet
2: Slightly less wispier compared with water-impregnated-sheet
1: Less wispier compared with water-impregnated-sheet

TABLE 8

| Formulation of Cosmetic Composition (mass %) | | Example B 24 | 25 | 26 | 27 | 28 |
|---|---|---|---|---|---|---|
| Cationic film-forming resin | N-Propionylpolyethyleneimine-methylpolysiloxane copolymer*1 | 5 | — | — | — | — |
| | Vinylpyrrolidone-N,N-dimethylaminoethyl methacrylate copolymer diethylsulfate*8 | — | 0.1 | — | — | — |
| Nonionic film-forming resin | Vinyl methyl ether-alkyl maleate copolymer*10 | — | — | 0.1 | — | — |
| Amphoteric film-forming resin | Methacryloyloxyethylcarboxybetaine-alkyl methacrylate copolymer*13 | — | — | — | 0.03 | — |
| Anionic film-forming resin | Alkyl acrylate-diacetoneacrylamide copolymer*16 | — | — | — | — | 0.1 |
| Ethanol | | 20 | 20 | 20 | 20 | 20 |
| Dipropylene glycol | | 1 | 1 | 1 | 1 | 1 |
| Cetrimonium chloride *2 | | 0.24 | 0.24 | 0.24 | 0.24 | 0.24 |
| Polyoxyethylene (9) C12-14 alkyl ether*3 | | 0.2 | 0.2 | 0.2 | 0.2 | 0.2 |
| Polyoxyethylene (60) hydrogenated castor oil*4 | | 0.75 | 0.75 | 0.75 | 0.75 | 0.75 |
| Polyoxyethylene (40) cetyl ether*5 | | 0.25 | 0.25 | 0.25 | 0.25 | 0.25 |
| EDTA-2Na | | 0.05 | 0.05 | 0.05 | 0.05 | 0.05 |
| Trometamine | | 0.2 | 0.2 | 0.2 | 0.2 | 0.2 |
| Lactic acid | | 0.08 | 0.08 | 0.08 | 0.08 | 0.08 |

TABLE 8-continued

| | Example B | | | | |
|---|---|---|---|---|---|
| Formulation of Cosmetic Composition (mass %) | 24 | 25 | 26 | 27 | 28 |
| Amodimethicone | — | 0.14 | 0.14 | 0.14 | 0.14 |
| AMP | — | — | 0.18 | — | — |
| Purified water | | | balance | | |
| Total | 100 | 100 | 100 | 100 | 100 |
| Pencil hardness of film-forming resin coating | 6B | F | H | 3H | H |
| Glide between hair and sheet during use of hairstyling cosmetic product | 43 | 42 | 46 | 32 | 37 |
| Feeling of hair being cleaned during use of hairstyling cosmetic product | 29 | 28 | 25 | 40 | 20 |
| Moist and soft feel of hair after use of hairstyling cosmetic product | 47 | 42 | 28 | 17 | 15 |
| Hair bunch texture of hair after use of hairstyling cosmetic product | 12 | 11 | 30 | 31 | 45 |
| Body and bounce of hair after use of hairstyling cosmetic product | 12 | 11 | 30 | 31 | 45 |
| Freedom of sticky feeling of hand and fingers during use of hairstyling cosmetic product | 38 | 42 | 44 | 46 | 42 |
| Freedom of unpleasant feeling of residue on hand and fingers after use and drying | 37 | 45 | 46 | 48 | 46 |
| Hair fixing properties after drying | 46 | 43 | 44 | 40 | 40 |
| Ease of delivery of cosmetic composition to hair | 48 | 50 | 50 | 49 | 50 |
| Freedom of drip from sheet | 49 | 46 | 48 | 48 | 49 |

Examples C

Test on Glide between Sheet and Hair

In a series of Examples C, the sheet-like hair care products obtained in Examples were tested by testers having finer hair than those who carried out the tests in Examples A. Therefore, the evaluations in Examples C were conducted under severer conditions than those adopted in Examples A.

Example C1

(1) Preparation of Substrate Sheet
Substrate sheet A used in Example A1 was used.
(2) Preparation of Cosmetic Composition and Impregnation into Nonwoven Fabric Sheet A hair cosmetic composition was prepared in a usual manner according to the formulation shown in Table 9. Twelve grams of the resulting cosmetic composition was infiltrated into the substrate sheet so that the ratio of the liquid cosmetic composition to the maximum water content of the substrate sheet [(amount of liquid cosmetic composition/maximum water content of substrate sheet)×100] was 48%.
(3) Packaging in a Packaging Container The sheet-like hair care products were packaged in a packaging container in the same manner as in Example A1.

Examples C2 to C16

A substrate sheet used in Example C1 was used, and a cosmetic composition shown in FIG. 9 was infiltrated into the substrate sheet in the same manner as in Example C1. A hair care product was made otherwise in the same manner as in Example C1.

Evaluation:

The sheet-like hair care products obtained in Examples were tested for bending resistance of sheet, thickness, and maximum water retention in the same manner as in Example A1. The viscosity and pH of the sheet-like hair care products were determined by the methods described below. The sheet-like hair care products were evaluated in terms of glide between the sheet-like hair care product and hair in wiping, ease of running fingers through hair in wiping, a clean feeling of hair and scalp after wiping, a fluffy feeling of hair after wiping and drying, and the touch of hair after wiping and drying. The results are shown in Table 9.

(a) Measurement of Viscosity and pH of Liquid Cosmetic Composition

The viscosity and pH of the liquid cosmetic composition before infiltration into the substrate sheet were measured. The pH was measured using a pH meter METERHM-30R from DKK Toa Corp.

The viscosity was measured using a Brookfield viscometer TOKIMEC VISCOMETER TV-20 from Toki Sangyo Co., Ltd. Measurements were made using a rotor No. M2 up to viscosities of 1,000 mPa·s and a rotor No. M3 for viscosities above 1,000 mPa·s. The number of rotation of the rotor was 60 rpm up to viscosities of 500 mPa·s, 30 rpm between 500 mPa·s and 4,000 mPa·s, and 12 rpm for viscosities above 4,000 mPa·s.

(b) Evaluation of Glide between the Sheet-like Hair Care Product and Hair in Wiping, Ease of Running Fingers Through Hair in Wiping, Clean Feeling of Hair and Scalp after Wiping, Fluffy Feeling of Hair after Wiping and Drying, and the Touch of Hair after Wiping and Drying These performance properties were evaluated in treating hair as follows.

The sheet-like hair care product was taken out of the packaging container and spread out on the palmer side of a tester's hand in such a manner that a part of it hung over the fingertips. The fingertips with the sheet on were applied to the roots of strands of hair at the top of the head in such a manner that bunches of hair strands got in between adjacent fingers, and moved to the tips of the hair strands while wiping the scalp and hair as if to comb with the fingers thereby to treat the hair. The similar hair treatment by finger combing was repeated ten times at the same part of the head without changing the positions of the fingertips on the sheet.

(b-1) Evaluation of Glide between the Sheet-like Hair Care Product and Hair in Wiping The smoothness of the glide of the sheet-like hair care product on the hair strands in the above-described combing operation was rated by a panel of ten testers having fine hair according to the following rating scale. The scores awarded by the testers were added up.

5: Glide very well.
4: Glide well.
3: Glide slightly well.
2: Glide slightly poorly.
1: Glide poorly.

(b-2) Evaluation of Ease of Running Fingers Through Hair in Wiping

Ease or smoothness of running fingers between hair strands in the above described treatment by finger combing was evaluated by a panel of ten testers having fine hair according to the following scale. The scores given by the panel were added up.

5: Run fingers very easily
4: Run fingers easily
3: Run fingers slightly easily
2: Run fingers slightly uneasily
1: Run fingers uneasily (b-3) Evaluation of Clean Feeling of Hair and Scalp after Wiping The clean feeling of the scalp and hair after the above-described treatment by finger combing was evaluated by a panel of ten testers having fine hair according to the following scale. The scores given by the panel were added up.

5: Very clean feeling.
4: Clean feeling.
3: Slightly clean feeling.
2: Not very clean feeling.
1: No clean feeling.

(b-4) Evaluation of Fluffy Feeling of Hair in Dry State after Wiping

The above described hair treatment by finger combing was followed by combing with a paddle brush ten times to fix the hair. After allowing the hair to dry spontaneously for 10 minutes, the apparent fluffy feeling of the hair in a dry state was evaluated by a panel of ten testers having fine hair according to the following scale. The scores by ten testers were added up.

5: Very fluffy
4: Fluffy
3: Slightly fluffy
2: Not so fluffy
1: Not fluffy (b-5) Evaluation of Touch (Moist Feeling) of Hair in Dry State after Wiping The above described hair treatment by finger combing was followed by combing with a paddle brush ten times to fix the hair. After allowing the hair to dry spontaneously for 10 minutes, the touch (moist feeling) of the dried hair was evaluated by ten testers having fine hair according to the following scale. The scores given by the ten testers were added up.

5: Very moist
4: Moist
3: Slightly moist
2: Not so moist
1: Not moist (b-6) Evaluation of Touch (Silky Feeling) of Hair in Dry State after Wiping Clean The above described hair treatment by finger combing was followed by combing with a paddle brush ten times to fix the hair. After allowing the hair to dry spontaneously for 10 minutes, the touch (silky feeling) of the dried hair was evaluated by ten testers having fine hair according to the following scale. The scores given by the ten testers were added up.

5: Very silky.
4: Silky.
3: Slightly silky.
2: Not so silky.
1: Not silky.

TABLE 9

| Formulation of Cosmetic Composition (mass %) | | | Example C | | | | | | | | | | | | | | |
|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 | 16 |
| Poly-saccharide | Cationic gum | Cationic guar gum Guar hydroxypropyltrimonium chloride*1 | 0.10 | — | — | — | — | — | — | — | — | — | — | — | — | — | — | — |
| | | Guar hydroxypropyltrimonium chloride*2 | — | 0.10 | — | — | — | — | — | — | — | — | — | — | — | — | — | — |
| | Cationic cellulose | Polyquaternium-10*3 | — | — | 0.10 | — | — | — | — | — | — | — | — | — | — | — | — | — |
| | | Polyquaternium-10*4 | — | — | — | 0.20 | — | — | — | — | — | — | — | — | — | — | — | — |
| | Nonionic Hydroxyalkyl cellulose | Hydroxyethylcellulose*5 | — | — | — | — | 0.10 | — | — | — | — | — | — | — | — | — | — | — |
| | | Hydroxypropylcellulose*6 | — | — | — | — | — | 0.20 | — | — | — | — | — | — | — | — | — | — |
| | | Methyl hydroxyethylcellulose*7 | — | — | — | — | — | — | 0.20 | — | — | — | — | — | — | — | — | — |
| | | Methyl hydroxyethylcellulose*7 | — | — | — | — | — | — | — | 0.10 | — | — | — | — | — | — | — | — |
| | | | — | — | — | — | — | — | — | — | 0.50 | — | — | — | — | — | — | — |
| | | | — | — | — | — | — | — | — | — | — | 0.50 | — | — | — | — | — | — |
| | | | — | — | — | — | — | — | — | — | — | — | 1.00 | — | — | — | — | — |
| | | | — | — | — | — | — | — | — | — | — | — | — | 1.00 | — | — | — | — |
| | | | — | — | — | — | — | — | — | — | — | — | — | — | 0.50 | — | — | — |
| | | | — | — | — | — | — | — | — | — | — | — | — | — | — | 0.50 | — | — |
| | | | — | — | — | — | — | — | — | — | — | — | — | — | — | — | 0.50 | — |
| Ethanol | | | 30.00 | 30.00 | 30.00 | 30.00 | 30.00 | 30.00 | 30.00 | 30.00 | 30.00 | 30.00 | 30.00 | 30.00 | 30.00 | 30.00 | 30.00 | 30.00 |
| Methyl p-hydroxybenzoate | | | 0.20 | 0.20 | 0.20 | 0.20 | 0.20 | 0.20 | 0.20 | 0.20 | 0.20 | 0.20 | 0.20 | 0.20 | 0.20 | 0.20 | 0.20 | 0.20 |
| Menthol JP (TABCOS) | | | 0.20 | 0.20 | — | — | — | — | — | — | — | — | — | — | — | — | — | 0.20 |
| Polyoxyethylene (60) hydrogenated castor oil*8 | | | — | — | — | — | — | — | — | 0.01 | — | — | — | — | — | — | — | — |
| Purified water | | | balance | | | | | | | | | | | | | | | |
| Total | | | 100 | 100 | 100 | 100 | 100 | 100 | 100 | 100 | 100 | 100 | 100 | 100 | 100 | 100 | 100 | 100 |
| Viscosity | | | 47 | 21 | 22 | 60 | 11 | 10 | 42 | 22 | 355 | 286 | 1900 | 350 | 150 | 38 | 600 | 15 |
| pH | | | 7.3 | 7.2 | 5.6 | 6.2 | 8.4 | 8.4 | 8.3 | 6.1 | 7.9 | 7.8 | 6.0 | 6.1 | 8.4 | 8.3 | 8.4 | 15 |
| Glide between sheet and hair in wiping | | | 40 | 42 | 35 | 40 | 30 | 35 | 38 | 35 | 45 | 47 | 45 | 47 | 34 | 38 | 40 | 50 |
| Ease of running fingers between hair strands in wiping | | | 41 | 42 | 36 | 36 | 25 | 35 | 38 | 35 | 43 | 46 | 45 | 47 | 34 | 38 | 40 | 40 |
| Clean feeling of hair and scalp after wiping | | | 36 | 34 | 46 | 40 | 36 | 30 | 26 | 43 | 28 | 25 | 13 | 17 | 28 | 30 | 17 | 15 |
| Fluffy feeling of dry hair after wiping | | | 37 | 38 | 35 | 35 | 35 | 30 | 30 | 35 | 33 | 35 | 40 | 40 | 25 | 30 | 30 | 40 |
| Touch (moist feeling) of dry hair after wiping | | | 37 | 38 | 30 | 25 | 33 | 35 | 34 | 32 | 37 | 39 | 38 | 32 | 35 | 37 | 37 | 15 |
| Touch (silky feeling) of dry hair after wiping | | | 42 | 40 | 43 | 39 | 35 | 37 | 40 | 46 | 33 | 34 | 34 | 36 | 26 | 38 | 37 | 50 |

Note that *1 to *7 in Table 9 are as follows.
*1: Jaguar EXCEL C-17, from Rhodia
*2: Jaguar C-14S, from Rhodia
*3: Poise C-150L, from Kao
*4: Poise C-80M, from Kao
*5: HEC Daicel SE850, from Daicel Chemical
*6: HPC-H, from Nippon Soda
*7: Structure Cell 12000M, from Akzo Nobel
*8: Quartamin 60W, from Kao As is apparent from the results in Table 9, the sheet-like hair care products obtained in Examples C1 to C8 proved to have an excellent glide on hair in wiping hair and to provide ease of running fingers between hair strands in wiping hair and scalp as compared with those obtained in Examples C9 to C16. The sheet-like hair care products obtained in Examples C1 to C8 provide a high clean feeling to hair and scalp after wiping and adds a fluffy look to the hairstyle after drying as compared with those obtained in Examples C9 to C16. The sheet-like hair care products obtained in Examples C1 to C8 also provide a pleasant touch to the hair after drying. Examples C1 through C16 show a tendency that the use of cationic guar gum as a polysaccharide gives an increased moist feeling, while the use of cationic cellulose gives an increased non-greasy like silky feeling, as compared with those obtained in Examples C9 to C16.

The sheet-like hair care product of Example C16 was found highly irritating to the eyes while the testers were wiping their hair and scalp for evaluation. The sheet-like hair care products of Examples C1 to C8 were not irritating to the eyes while in use.

Examples D

Test on Smell Emission

Example D1

(1) Preparation of Substrate Sheet

Substrate sheet A used in Example A1 was used.

(2) Synthesis of Polysilicone-9 for Use in Cosmetic Composition

Synthesized in the same manner as in Synthesis Example 2.

(3) Preparation of Cosmetic Composition and Impregnation into Nonwoven Fabric Sheet A hair cosmetic composition was prepared in a usual manner according to the formulation shown in Table 10 below. Ten grams of the resulting cosmetic composition was infiltrated into the substrate sheet so that the ratio of the liquid cosmetic composition to the maximum water content of the substrate sheet was 40%.

(4) Packaging in a Packaging Container

The sheet-like hair care product was packaged in a packaging container in the same manner as in Example A1.

Examples D2 to D8

A substrate sheet used in Example D1 was used, and a cosmetic composition shown in FIG. was infiltrated into the substrate sheet in the same manner as in Example D1. A hair care product was made otherwise in the same manner as in Example D1.

Evaluation:

The bending resistance of sheet, thickness, and maximum water retention of the hair care products obtained in Examples were determined in the same manner as in Example A1. The sheet-like hair care products were evaluated for the smell emitted therefrom while in use, the smell of hair after the cosmetic composition dried, the touch of hair while in use, manageability of hair after the cosmetic composition dried, and the stability of the cosmetic composition according to the methods describe below. The results of measurement and evaluation are shown in Table 10.

(a) Evaluation of Smell of Sheet-like Hair Care Product during Use

The sheet-like hair care product was taken out of the packaging container, spread out, and sniffed by a panel of ten members from a distance of 5 cm from their nose. The intensity of the smell was rated according to the following rating scale. The scores awarded by the panel were added up.
5: Too strong
4: Slightly strong
3: Neutral
2: Slightly weak
1: Too weak The closer to 30 the total score is, the more ideal the smell the sheet-like hair care product emitted when spread out.

(b) Evaluation of Smell of Treated Hair after Cosmetic Composition Dries

Four grams of Japanese damaged hair was wiped with the sheet-like hair care product taken out of the packaging container so that 0.8 g of the liquid cosmetic composition was left on the hair (liquor ratio: 0.2). Thirty minutes later, the treated hair was sniffed by a panel of ten testers, and the intensity of the smell was rated according to the following scale. The scores given by the panel were added up.
5: Too strong
4: Slightly too strong
3: Neutral
2: Slightly weak
1: Too weak The closer to 30 the total score is, the more ideal the smell of the treated hair after drying is.

(c) Evaluation of Ease of Running Fingers Through Hair while Wet after Treatment with Sheet-like Hair Care Product The sheet-like hair care product was taken out of the packaging container and spread out on the palmer side of a tester's hand in such a manner that a part of it hung over the fingertips. The fingertips with the sheet on were applied to the roots of strands of hair at the top of the head in such a manner that bunches of hair got in between adjacent fingers and moved to the ends of the hair strands while combing with the fingers thereby to treat the hair. Ease of running fingers through the wet strands of hair immediately after the treatment was rated by a panel of 10 testers according to the following scale. The scores by the testers were added up.
5: Run fingers very easily
4: Run fingers easily
3: Run fingers lightly easily
2: Run fingers slightly uneasily
1: Run fingers uneasily (d) Evaluation of Smoothness of Hair after Cosmetic Composition Dries Smoothness of hair after the above described hair treatment by finger combing and drying was evaluated and rated by a panel of ten testers according to the following scale. The scores awarded by the panel were added up.
5: Very smooth
4: Smooth
3: Slightly smooth
2: Slightly unsmooth
1: Unsmooth (e) Evaluation of Manageability of Hair after Cosmetic Composition Dries Manageability of hair after the above described hair treatment and drying was evaluated and rated by a panel of ten testers according to the following scale. The scores awarded by the panel were added up.
5: Very manageable
4: Manageable 3: Slightly manageable
2: Slightly unmanageable
1: Unmanageable (f) Evaluation of Storage Stability of Cosmetic Composition The cosmetic compositions described in Table 10 were stored at 50° C. for one month. The state of the cosmetic composition after the storage was visually observed and graded "pass (P)" when no phase separation was observed or "fail (F)" when phase separation was observed.

for 6 hours. After the cold storage, the sheet-like hair care product was taken out of the container, spread out, and sniffed by a panel of ten testers from a distance of 5 cm from their nose.

Evaluation of the smell at a high temperature was similarly performed by sealing the sheet-like hair care products of Examples in the respective packaging containers shown in FIG. 1 and storing the containers at 35° C. for 6 hours. After the hot storage, the sheet-like hair care product was

TABLE 10

| | | Example D | | | | | | | |
|---|---|---|---|---|---|---|---|---|---|
| | | 1 | 2 | 3 | 4 | 5 | 6 | 7 | 8 |
| (B-4-1) (%) | Amino-modified silicone oil (*1) | 0.14 | 0.14 | 0.14 | 0.14 | 0.14 | 0.14 | 0 | 0.14 |
| (B-8) | Fragrance | 0.08 | 0.08 | 0.08 | 0.08 | 0.08 | 0.08 | 0.08 | 0.08 |
| (B-2-3) (B-2-3-1) (%) | Polyoxyethylene (9) C12-14 alkyl ether (*2) | 0.2 | 0.2 | 0.2 | 0.2 | 0.2 | 0.2 | 0.2 | 0 |
| | Ceteth-40 (*3) | 0.25 | 0 | 0 | 0.5 | 1 | 0 | 0 | 0 |
| | Ceteareth-7 (*4) | 0.07 | 0.07 | 0.07 | 0.07 | 0.07 | 0.07 | 0.07 | 0.07 |
| | Ceteareth-25 (*4) | 0.01 | 0.01 | 0.01 | 0.01 | 0.01 | 0.01 | 0.01 | 0.01 |
| | Sum of (B-2-3-1) | 0.53 | 0.28 | 0.28 | 0.78 | 1.28 | 0.28 | 0.28 | 0.08 |
| B-2-3-2 | Polyoxyethylene (60) hydrogenated castor oil(C2) (*5) | 0.75 | 1 | 1 | 0.5 | 0 | 5 | 1 | 0 |
| | Sum of (B-2-3) (%) | 1.28 | 1.28 | 1.28 | 1.28 | 1.28 | 5.28 | 1.28 | 0.08 |
| (B-3) (%) | Purified water | | | | balance | | | | |
| (B-1) (%) | Ethanol | 20 | 20 | 20 | 20 | 20 | 20 | 20 | 20 |
| | Dipropylene glycol | 1 | 1 | 1 | 1 | 1 | 1 | 1 | 1 |
| Others (%) | Polysilicone-9 disclosed in Synthesis Example | 0.25 | 0.5 | 0.25 | 0.25 | 0.25 | 0.25 | 0.25 | 0.25 |
| | Cetrimonium chloride (*6) | 0.24 | 0.24 | 0.24 | 0.24 | 0.24 | 0.24 | 0.24 | 0.24 |
| | Methyl p-hydroxybenzoate | 0.15 | 0.15 | 0.15 | 0.15 | 0.15 | 0.15 | 0.15 | 0.15 |
| | EDTA-2Na (*7) | 0.05 | 0.05 | 0.05 | 0.05 | 0.05 | 0.05 | 0.05 | 0.05 |
| | Total (%) | 100 | 100 | 100 | 100 | 100 | 100 | 100 | 100 |
| | $[n_A + n_{B7}]/[n_{Ca}]$ | 0.17 | 0.17 | 0.17 | 0.17 | 0.17 | 0.04 | 0.06 | 2.75 |
| | $n_{C-1}/n_{C-2}$ | 0.71 | 0.28 | 0.28 | 1.56 | | 0.06 | 0.28 | |
| Smell of hair care product in use (exclusive of ethanolic smell) | | 32 | 25 | 28 | 31 | 25 | 18 | 26 | * |
| Smell of hair after cosmetic composition dries | | 33 | 35 | 31 | 32 | 28 | 42 | 28 | * |
| Ease of running fingers through treated hair while wet | | 48 | 38 | 39 | 46 | 40 | 37 | 21 | * |
| Smoothness of treated hair after cosmetic composition dries | | 49 | 40 | 42 | 48 | 47 | 15 | 25 | * |
| Manageability of treated hair after cosmetic composition dries | | 47 | 50 | 48 | 46 | 38 | 50 | 32 | * |
| Storage stability of cosmetic composition | | P | P | P | P | P | P | P | F |

Note that *1 to *7 in Table 10 are as follows.
*1: Amino-modified silicone of formula (1), wherein A is methyl; R' is —CH$_2$CH$_2$CH$_2$—; n is 1; total number of silicon atoms (p + q + 2) is 1500 in number average; and amino equivalent is 13000 g/mol), emulsified.
*2: Softanol 90, from Kao
*3: Nikkol BC-40TX, form Nikko Chemicals
*4: Carryover from ingredient *1
*5: Emanon CH-60, from Kao
*6: Quartamin 60W, from Kao
*7: Clewat N, from Nagase Chemtex As is apparent from the results in Table 10, the sheet-like hair care products obtained in Examples D1 to D5 give off a good smell while in use and also after the cosmetic composition applied to the hair dries, provide a good touch to the hair while in use, and make the hair manageable after drying. It is also seen that the cosmetic compositions used in these products exhibit high stability. In contrast, it is seen that the sheet-like hair care product of Example D6 containing an increased amount of the polyoxyalkylene-added nonionic surfactant is inferior to those of Examples D1 to D5 in the touch of hair after drying.

(g) Emission of Smell under Different Environmental Conditions

Out of the sheet-like hair care products of Table 10, those of Examples D1, D3, D4, and D5 were further evaluated for emission of smell in a low and a high temperature environment as follows.

Evaluation of the smell at a low temperature was performed by sealing the sheet-like hair care products of Examples D1, D3, D4, and D5 in the respective packaging containers shown in FIG. 1 and storing the package at 5° C.

taken out of the container, spread out, and sniffed by a panel of ten testers from a distance of 5 cm from their nose.

As a result, the testers reported that the products of Examples D1 and D4 smelled obviously of the fragrance when stored at 5° C. as compared with those of Examples D3 and D5 and that the products of Examples D1 and D4 smelled of the fragrance when stored at 35° C. as compared with those of Examples D3 and D5.

Examples E

Test on Fresh Feeling and Irritation to Eyes and Nose

Example E1

(1) Preparation of Substrate Sheet
Substrate sheet A used in Example A1 was used.
(2) Synthesis of Polysilicone-9 for Use in Cosmetic Composition
Synthesized in the same manner as in Synthesis Example 2.

(3) Preparation of Cosmetic Composition and Impregnation into Nonwoven Fabric Sheet A cosmetic composition was prepared in a usual manner according to the formulation shown in Table 11 below. Ten grams of the resulting cosmetic composition was infiltrated into the substrate sheet so that the ratio of the liquid cosmetic composition to the maximum water content of the substrate sheet was 40%.

(4) Packaging in a Packaging Container

The sheet-like hair care product hair care products were packaged in a packaging container in the same manner as in Example A1.

Examples E2 to E11

A substrate sheet used in Example E1 was used, and a cosmetic composition shown in FIG. 11 was infiltrated into the substrate sheet in the same manner as in Example E1. A hair care product was made otherwise in the same manner as in Example E1.

Evaluation:

The bending resistance of sheet, thickness, and maximum water retention of the hair care products obtained in Examples were determined in the same manner as in Example A1. The sheet-like hair care products taken out of the packaging containers were evaluated for freedom from irritating odor, duration of a cooling sensation in use, the touch of hair in use (while the hair was wet and after the cosmetic composition dried), the manageability of hair after the cosmetic composition dried, and stability of the cosmetic composition in accordance with the following methods. The results obtained are shown in Table 11.

(a) Evaluation of Freedom from Irritating Odor of Sheet-like Hair Care Product Taken Out of container The sheet-like hair care product obtained in Examples were each taken out of the container, spread out, and sniffed by a panel of ten testers from a distance of 5 cm from their nose. Freedom from irritating odor was rated according to the following scale. The scores given by the testers were added up.
5: No irritating odor
4: Almost no irritating
3: Slight irritating odor
2: Irritating odor
1: Strong irritating odor (b) Evaluation of Cooling Sensation Immediately after Use and with Time Thereafter The sheet-like hair care product impregnated with the cosmetic composition was taken out of the container, spread out on the palmer side of a tester in such a manner that a part of it hung over the fingertips, and applied and rubbed to the scalp to wipe clean the scalp in such a manner that strands of hairs got in between adjacent fingers. A panel of ten testers assessed the cooling sensation they felt immediately after the wiping and also after 30 minutes from the end of the wiping operation according to the following scale. The scores by the panel were added up.
5: Very strong cooling sensation
4: Strong cooling sensation
3: Slightly strong cooling sensation
2: Slightly weak cooling sensation
1: Weak cooling sensation (c) Evaluation of Ease of Running Fingers Through Wet Hair after Use of Sheet-like Hair Care Product The sheet-like hair care products of Examples were each taken out of the container, spread out on the palmer side of a tester in such a manner that a part of it hung over the fingertips. The fingertips with the sheet on were applied to the roots of strands of hair at the top of the head in such a manner that strands of hair got in between adjacent fingers and moved to the tip of the hair strands as if to comb with the fingers thereby to treat the hair. While the hair was wet immediately after the treatment, fingers were run therethrough, and the smoothness of running fingers through the hair was rated by a panel of ten testers according to the following rating system. The scores given by the panel were added up.
5: Run fingers very smoothly
4: Run fingers smoothly
3: Run fingers slightly smoothly
2: Run fingers slightly unsmoothly
1: Run fingers unsmoothly (d) Evaluation of Smoothness of Hair after Cosmetic Composition Dries After the above-described hair treatment by finger combing and after the hair dried, the smoothness of the treated hair was rated by a panel of ten testers according to the following scale. The scores awarded by the panel were added up.
5: Very smooth
4: Smooth
3: Slightly smooth
2: Slightly unsmooth
1: Unsmooth (e) Evaluation of Manageability of Hair after Cosmetic Composition Dries After the above-described hair treatment by finger combing and after the hair dried, manageability of the treated hair was rated by a panel of ten testers according to the following scale. The scores awarded by the panel were added up.
5: Very manageable
4: Manageable
3: Slightly manageable
2: Slightly unmanageable
1: Unmanageable (f) Evaluation of Storage Stability of Cosmetic Composition The cosmetic compositions described in Table 11 were stored at 50° C. for one month. The state of the cosmetic composition after the storage was visually observed and graded "pass (P)" when no phase separation was observed or "fail (F)" when phase separation was observed.

TABLE 11

|  | (%) | Example E ||||||||||| 
|  |  | 1 | 2 | 3 | 4 | 5 | 6 | 7 | 8 | 9 | 10 | 11 |
| --- | --- | --- | --- | --- | --- | --- | --- | --- | --- | --- | --- | --- |
| (B-4-1) (%) | Amino-modified silicone oil*1 | 0.14 | 0.14 | 0.14 | 0.14 | 0.14 | 0.14 | 0.14 | 0 | 0.14 | 0.14 | 1.00 |
| (B-7) (%) | C-Menthol | 0.05 | 0.1 | 0.1 | 0.15 | 0.15 | 0.15 | 0 | 0.1 | 0.15 | 0.15 | 0.2 |
| (B-2-3-1) (%) | Ceteth-40 (*2) | 0.25 | 0.25 |  |  |  |  |  | 0.25 | 0.25 |  |  |
|  | Steareth-5 (*3) |  |  |  | 0.25 |  |  |  |  |  |  |  |
|  | Laureth-23 (*4) |  |  |  |  |  | 0.25 |  |  |  |  |  |

TABLE 11-continued

| (%) | | Example E 1 | 2 | 3 | 4 | 5 | 6 | 7 | 8 | 9 | 10 | 11 |
|---|---|---|---|---|---|---|---|---|---|---|---|---|
| | Laureth-4 (*5) | | | | | | 0.25 | | | | | |
| | Polyoxyethylene (9) C12-14 alkyl ether (*6) | 0.2 | 0.2 | 0.2 | 0.2 | 0.2 | 0.2 | 0.2 | 0.2 | 0.2 | 0.2 | |
| | Ceteareth-7 (*7) | 0.07 | 0.07 | 0.07 | 0.07 | 0.07 | 0.07 | 0.07 | 0.07 | 0.07 | 0.07 | 0.20 |
| | Ceteareth-25 (*7) | 0.01 | 0.01 | 0.01 | 0.01 | 0.01 | 0.01 | 0.01 | 0.01 | 0.01 | 0.01 | 0.04 |
| | Sum of (B-2-3-1) | 0.53 | 0.53 | 0.28 | 0.53 | 0.53 | 0.53 | 0.53 | 0.53 | 0.28 | 0.28 | 0.24 |
| (B-2-3-2) (%): | Polyoxyethylene (60) hydrogenated castor oil (*8) | 0.75 | 0.75 | 1 | 0.75 | 0.75 | 0.75 | 0.75 | 0.75 | 0 | 0 | 0.16 |
| | Sum of (B-2-3-1) and (B-2-3-2) | 1.28 | 1.28 | 1.28 | 1.28 | 1.28 | 1.28 | 1.28 | 1.28 | 0.28 | 0.28 | 0.40 |
| (B-3) (%) | Water | | | | | | balance | | | | | |
| (B-1) (%) | Ethanol | 20 | 20 | 20 | 20 | 20 | 20 | 20 | 20 | 20 | 20 | 20 |
| | Dipropylene glycol | 1 | 1 | 1 | 1 | 1 | 1 | 1 | 1 | 1 | 1 | 1 |
| | Sum of (B-1) | 21 | 21 | 21 | 21 | 21 | 21 | 21 | 21 | 21 | 21 | 21 |
| (B-2-3-1') (%) | Polyoxyethylene (20E.O.) sorbitan palm oil fatty acid ester (*9) | | | | | | | | | | 0.25 | |
| | Polyoxyethylene (20E.O.) sorbitan monostearate (*10) | | | | | | | | | 1 | 0.75 | |
| Others (%) | Polysilicone-9 disclosed in Synthesis Example | 0.25 | 0.25 | 0.50 | 0.25 | 0.25 | 0.25 | 0.25 | 0.25 | 0.50 | 0.50 | 0.50 |
| | Cetyltrimethylammonium chloride (*11) | 0.24 | 0.24 | 0.24 | 0.24 | 0.24 | 0.24 | 0.24 | 0.24 | 0.24 | 0.24 | 0.24 |
| | EDTA (*12) | 0.05 | 0.05 | 0.05 | 0.05 | 0.05 | 0.05 | 0.05 | 0.05 | 0.05 | 0.05 | 0.05 |
| | Methyl p-hydroxybenzoate | 0.15 | 0.15 | 0.15 | 0.15 | 0.15 | 0.15 | 0.15 | 0.15 | 0.15 | 0.15 | 0.15 |
| | $[n_A + n_{B7}]/[n_C + n_D]$ | 0.15 | 0.19 | 0.19 | 0.23 | 0.23 | 0.23 | 0.11 | 0.08 | 1.04 | 1.04 | 2.99 |
| | $n_C/n_D$ | 0.71 | 0.71 | 0.28 | 0.71 | 0.71 | 0.71 | 0.71 | 0.71 | | | 1.50 |
| | Freedom from irritating odor when spread out | 48 | 46 | 44 | 38 | 39 | 38 | 49 | 34 | 32 | 30 | 24 |
| | Cooling sensation immediately after use | 42 | 43 | 47 | 45 | 44 | 42 | 26 | 43 | 45 | 44 | 48 |
| | Cooling sensation after lapse of time | 45 | 44 | 41 | 46 | 44 | 43 | 12 | 42 | 44 | 45 | 47 |
| | Ease of running fingers through wet treated hair | 48 | 47 | 43 | 42 | 41 | 42 | 45 | 13 | 34 | 32 | 50 |
| | Smoothness of treated hair after drying | 45 | 45 | 41 | 44 | 42 | 39 | 46 | 23 | 29 | 33 | 49 |
| | Manageability of treated hair after drying | 44 | 46 | 48 | 41 | 38 | 38 | 44 | 28 | 37 | 38 | 15 |
| | Storage stability of cosmetic composition | P | P | P | P | P | P | P | P | F | F | F |

Note that *1 to *12 in Table 11 are as follows.
*1: Amino-modified silicone of formula (1), wherein A is methyl; R' is —CH$_2$CH$_2$CH$_2$—; n is 1; total number of silicon atoms (p + q + 2) is 1500 in number average; and amino equivalent is 13000 g/mol; emulsified.
*2: Nikkol BC-40TX, form Nikko Chemicals
*3: Emulgen 305, from Kao
*4: Emulgen 123P, from Kao
*5: Emulgen 105, from Kao
*6: Softanol 90, from Kao
*7: Carryover from ingredient *1
*8: Emanon CH-60, from Kao
*9: Leodor TW-L120, from Kao
*10: Leodor TW-S120, from Kao
*11: Quartamin 60W, from Kao
*12: Clewat N, from Nagase Chemtex As is apparent from the results in Table 11, the sheet-like hair care products of Examples E1 through E6 provide a long-lasting cooling sensation ascribed to C-menthol while controlling the irritating odor of C-menthol. They also provide a good touch to hair while in use (while the hair is wet and after the cosmetic composition dries) and make the dried hair manageable. The cosmetic compositions used in these sheet-like hair care products prove highly stable in storage. In contrast, the sheet-like hair care product of Example E7, which is free of l-menthol, does not give a cooling sensation during use. The sheet-like hair care product of Example E8, which is free of an amino-modified silicone, is not good in terms of touch of hair during use (while the hair is wet). The sheet-like hair care products of Examples E9 and E10, which are free of ingredient (B-2-3-2), give off a strong irritating odor of C-menthol and provide a rough touch to the hair after drying the cosmetic composition. The cosmetic composition of Examples E9 and E10 lack stability. In Example E11, in which the contents of ingredients are out of the specific ratio, the cosmetic composition lacks stability and emits a strong irritating odor of l-menthol.

Example E12

A sheet-like hair care product was prepared in the same manner as in Example E1, except that the same substrate sheet as used in Example E1 was impregnated with a liquid cosmetic composition shown in Table 12 below in the same quantity as in Example E1. When the resulting sheet-like hair care product was used in finger combing, it provided a long-lasting cooling sensation without emitting a perceptible irritating odor of menthol and without giving irritation to the users' eyes. It was also capable of making the hair manageable.

TABLE 12

Example E12

| | | |
|---|---|---|
| (B-4-1) (%) | Amino-modified silicone oil*1 | 0.14 |
| (B-7) (%) | C-Menthol | 0.10 |
| (B-2-3-1) (%) | Ceteth-40*2 | 0.75 |
| | Polyoxyethylene (9) C12-14 alkyl ether*6 | 0.20 |
| | Ceteareth-7*7 | 0.07 |
| | Ceteareth-25*7 | 0.01 |
| (B-2-3-2) (%) | Polyoxyethylene (60) hydrogenated castor oil*8 | 0.25 |
| (B-3) (%) | Purified water | balance |
| (B-1) (%) | 95% Synthetic alcohol | 20.00 |
| | Dipropylene glycol | 1.00 |
| Others (%) | Polysilicone-9 of Synthesis Example | 0.25 |
| | Cetyltrimethylammonium chloride*11 | 0.24 |
| | EDTA*12 | 0.05 |
| | Methyl p-hydroxybenzoate | 0.15 |

Note that *1 to *12 in Table 12 are as follows.
*1Amino-modified silicone of formula (1), wherein A is methyl; R' is —$CH_2CH_2CH_2$—; n is 1; total number of silicon atoms (p + q + 2) is 1500 in number average; and amino equivalent is 13000 g/mol), emulsified.
*2Nikkol BC-40TX, form Nikko Chemicals
*6Softanol 90, from Kao
*7Carryover from ingredient *1
*8Emanon CH-60, from Kao
*11Quartamin 60W, from Kao
*12Clewat N, from Nagase Chemtex Examples F Test on Deodorant Performance Example F1

(1) Preparation of Substrate Sheet

Substrate sheet A used in Example A1 was used.

(2) Preparation of Cosmetic Composition and Impregnation into Nonwoven Fabric Sheet A hair cosmetic composition was prepared in a usual manner according to the formulation shown in Table 13 below. Twelve grams of the resulting cosmetic composition was infiltrated into the substrate sheet so that the ratio of the liquid cosmetic composition to the maximum water content of the substrate sheet [(amount of liquid cosmetic composition/maximum water content of substrate sheet)×100] was 48%.

(3) Packaging in a Packaging Container

The sheet-like hair care product was packaged in a packaging container in the same manner as in Example A1.

Examples F2 to F12

A substrate sheet used in Example F1 was used, and a cosmetic composition shown in FIG. 13 was infiltrated into the substrate sheet in the same manner as in Example F1. A hair care product where the sheet-like hair care products were packaged in a packaging container was made otherwise in the same manner as in Example A1.

Evaluation:

The sheet-like hair care products obtained in Examples were tested for bending resistance of sheet, thickness, and maximum water retention in the same manner as in Example A1. The viscosity and pH of the cosmetic compositions were measured by the methods described below. The sheet-like hair care products were evaluated in terms of glide on hair in wiping, ease of running fingers through hair in wiping, the smell of hair and scalp and a clean feeling of hair and scalp after wiping, a fluffy feeling of hair after wiping and drying, and the touch of hair after wiping and drying. The results are shown in Table 13.

(a) Measurement of Viscosity and pH of Liquid Cosmetic Composition

The viscosity and pH of the liquid cosmetic composition before infiltration into the substrate sheet were measured. The pH was measured using a pH METERHM-30R from DKK Toa Corp. The viscosity was measured using a Brookfield viscometer TV-20 from Toki Sangyo Co., Ltd. Measurements were made using a rotor No. M2 up to viscosities of 1,000 mPa·s and a rotor No. M3 for viscosities above 1,000 mPa·s. The number of rotation of the rotor was 60 rpm up to viscosities of 500 mPa·s, 30 rpm between 500 mPa·s and 4,000 mPa·s, and 12 rpm for viscosities above 4,000 mPa·s.

(b) Evaluation of Glide between the Sheet-like Hair Care Product and Hair in Wiping, Ease of Running Fingers Through Hair in Wiping, Smell of Hair and Scale after Wiping, Clean Feeling of Hair and Scalp after Wiping, Fluffy Feeling of Hair after Wiping and Drying, and the Touch of Hair after Wiping and Drying Evaluation of these performance properties was conducted through the treatment of hair as follows.

The sheet-like hair care product was taken out of the packaging container and spread out on the palmer side of a tester's hand with a part of it hanging over the fingertips. The fingertips with the sheet on were applied to the roots of strands of hair at the top of the head in such a manner that strands of hair got in between adjacent fingers and moved to the tip of the hair strands while wiping the scalp and hair as if to comb with the fingers thereby to treat the hair. The similar hair treatment by finger combing was repeated ten times at the same part of the head without changing the positions of the fingertips on the sheet.

(b-1) Evaluation of Glide between the Sheet-like Hair Care Product and Hair in Wiping The smoothness of the glide of the sheet-like hair care product on the hair strands in the above-described combing operation was evaluated by a panel of ten testers according to the following rating scale. The scores awarded by the testers were added up.

5: Glide very well.
4: Glide well.
3: Glide slightly well.
2: Glide slightly poorly.
1: Glide poorly.

(b-2) Evaluation of Ease of Running Fingers Through Hair in Wiping

Ease or smoothness of running fingers between hair strands in the above described treatment by finger combing was evaluated by a panel of ten testers according to the following scale. The scores given by the testers were added up.

5: Run fingers very easily
4: Run fingers easily
3: Run fingers slightly easily
2: Run fingers slightly uneasily
1: Run fingers uneasily (b-3) Evaluation of Clean Feeling of Scalp and Hair after Wiping The clean feeling of the scalp and hair after the above-described treatment by finger combing was evaluated and rated by a panel of ten testers having fine hair according to the following scale. The scores given by the testers were added up.

5: Very clean feeling
4: Clean feeling

3: Slightly clean feeling
2: Not very clean feeling
1: No clean feeling (b-4) Evaluation of Fluffy Feeling of Hair in Dry State after Wiping The above described hair treatment by finger combing was followed by combing with a paddle brush ten times to fix the hair. After allowing the hair to dry spontaneously for 10 minutes, the apparent fluffy feeling of the hair in a dry state was evaluated by ten testers having fine hair according to the following scale. The scores by ten testers were added up.

5: Very fluffy
4: Fluffy
3: Slightly fluffy
2: Not so fluffy
1: Not fluffy (b-5) Evaluation of Touch (Moist Feeling) of Hair in Dry State after Wiping The above described hair treatment by finger combing was followed by combing with a paddle brush ten times to fix the hair. After allowing the hair to dry spontaneously for 10 minutes, the touch (moist feeling) of the dried hair was evaluated by ten testers having fine hair according to the following scale. The scores given by the ten testers were added up.

5: Very moist
4: Moist
3: Slightly moist
2: Not so moist
1: Not moist (b-6) Evaluation of Touch (Silky Feeling) of Hair in Dry State after Wiping Clean The above described hair treatment by finger combing was followed by combing with a paddle brush ten times to fix the hair. After allowing the hair to dry spontaneously for 10 minutes, the touch (silky feeling) of the dried hair was evaluated by ten testers having fine hair according to the following scale. The scores given by the ten testers were added up.

5: Very silky
4: Slightly silky
3: Neither
2: Not so silky
1: Not silky (b-7) Evaluation of Fresh Feeling Immediately after Wiping and with Time Thereafter The above-described hair treatment by finger combing was performed by a panel of ten testers having fine hair. After the treatment, the panel evaluated and rated the fresh feeling on their scalp immediately after the treatment and after an elapse of 10 minutes from the treatment in accordance with the following scale. The scores given by the panel were added up.

5: Very fresh
4: Slightly fresh
3: Neither
2: Not so fresh
1: Poor

TABLE 13

| Formulation of Cosmetic Composition (mass %) | | Example F | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Polyhydroxylamine compound | Tris(hydroxymethyl)aminomethane | 0.1 | 0.1 | 0.1 | 0.1 | 0.1 | 0.1 | 0.1 | 0.1 | 0.1 | 0.1 | 0.1 | 0.1 |
| Thickening polymer | Anionic | Acrylates/C10-30 alkyl acrylate crosspolymer*1 | 0.1 | | | | | | | | 0.3 | | | |
| | | Acrylates/C10-30 alkyl acrylate crosspolymer*2 | | 0.1 | | | | | | | | 1 | | |
| | | Carbomer*3 | | | 0.1 | | | | | | | | | |
| | | Acrylates/steareth-20 methacrylate copolymer*4 | | | | 0.2 | | | | | | | | |
| | | Acrylate/vinyl neodecanoate crosspolymer*5 | | | | | 0.05 | | | | | | | |
| | | Ammonium acryloyldimethyltaurate/beheneth-25 methacrylate crosspolymer*6 | | | | | | 0.05 | | | | | | |
| Anionic polysaccharide | | Hydroxypropylxanthan gum*7 | | | | | | | 0.2 | | | | | |
| Nonionic | | PEG-150/decyl alcohol/SMDI crosspolymer*8 | | | | | | | | | | | 0.2 | |
| Cationic | | Polyquaternium-86*9 | | | | | | | | | | | | 0.1 |
| 95% Synthetic alcohol | | | 30 | 30 | 30 | 30 | 30 | 30 | 30 | 30 | 30 | 30 | 30 | 30 |
| Menthol JP (TAB)COS | | | 0.2 | 0.2 | 0.2 | 0.2 | 0.2 | 0.2 | 0.2 | 0.2 | 0.2 | 0.2 | 0.2 | 0.2 |
| Methyl p-hydroxybenzoate | | | 0.2 | 0.2 | 0.2 | 0.2 | 0.2 | 0.2 | 0.2 | 0.2 | 0.2 | 0.2 | 0.2 | 0.2 |
| Purified water | | | balance | | | | | | | | | | | |
| Total | | | 100 | 100 | 100 | 100 | 100 | 100 | 100 | 100 | 100 | 100 | 100 | 100 |
| Viscosity | | | 145 | 2000 | 1650 | 11 | 6 | 5 | 80 | 5 | 8080 | 6890 | 5 | 6 |

TABLE 13-continued

| Formulation of Cosmetic Composition (mass %) | Example F | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| PH | 8.11 | 7.5 | 7.47 | 8.1 | 8.4 | 8.38 | 6.6 | 8 | 6.64 | 7.2 | 8.4 | 8.24 |
| Glide between sheet and hair in wiping | 35 | 37 | 36 | 35 | 21 | 30 | 40 | 15 | 40 | 40 | 24 | 23 |
| Ease of running fingers through hair in wiping | 39 | 38 | 30 | 30 | 30 | 28 | 40 | 15 | 40 | 45 | 24 | 23 |
| Clean feeling of hair and scalp after wiping | 50 | 45 | 47 | 30 | 36 | 30 | 30 | 50 | 25 | 16 | 36 | 32 |
| Fluffy feeling of hair in dry state after wiping | 40 | 36 | 40 | 37 | 37 | 27 | 35 | 40 | 34 | 30 | 30 | 25 |
| Touch (moist feeling) of hair in dry state after wiping | 20 | 23 | 24 | 37 | 38 | 30 | 34 | 15 | 27 | 10 | 39 | 37 |
| Touch (silky feeling) of hair in dry state after wiping | 45 | 36 | 40 | 37 | 37 | 27 | 35 | 50 | 35 | 30 | 28 | 38 |
| Fresh feeling immediately after wiping | 45 | 40 | 40 | 44 | 44 | 45 | 43 | 45 | 23 | 25 | 44 | 44 |
| Fresh feeling after 10 minutes from wiping | 44 | 44 | 45 | 34 | 32 | 30 | 36 | 24 | 28 | 33 | 24 | 23 |

Note that *1 to *9 in Table 13 are as follows.
*1: Carbopol ETD2020, from Lubrizol Advanced Materials, Inc.
*2: Pemulen TR-1, from Lubrizol Advanced Materials
*3: Carbopol 981, from Lubrizol Advanced Materials
*4: Aculyn 22, from The Dow Chemical
*5: Aculyn 38, from The Dow Chemical
*6: Aristoflex HMB, from Clariant
*7: Rhaball Gum EX, from DSP Gokyo Food & Chemical
*8: Aculyn 44, from The Dow Chemical
*9: Luvigel Advanced, from BASF As is apparent from the results in Table 13, the sheet-like hair care products obtained in Examples F1 through F7 have an excellent glide on hair and provide ease in running fingers in wiping hair and scalp as compared with those of Examples F8 through F12. They provide a high deodorant effect and a clean feeling on the hair and scalp after wiping and give a fluffy finish to the treated hair after drying. They also provide a pleasant touch to hair in a dry state after wiping and a long-lasting fresh feeling after use.

The invention claimed is:

1. A method for treating hair with a sheet-like hair care product, the method comprising:
   dispensing the sheet-like hair care product from an access opening of a packaging container, thereby spreading out the sheet-like hair care product and retaining from 6 g to 25 g of a liquid cosmetic composition component (B) in the sheet-like hair care product, and then
   contacting hair strands with the sheet-like hair care product,
   wherein the sheet-like hair care product comprises:
   (A) a substrate sheet having an area of from 50 $cm^2$ to 1600 $cm^2$, comprising cellulosic fibers, and having a bending resistance of 10 mm to 70 mm as measured by the 45° cantilever method in accordance with JIS L1096:2010 and
   (B) a liquid cosmetic composition,
   wherein said substrate sheet is impregnated with from 6 g to 25 g of said liquid cosmetic composition per sheet, in an amount of from 0.012 g to 0.037 g of said liquid cosmetic composition per $cm^2$ of said substrate sheet,
   wherein the substrate sheet has a mass before impregnation with the liquid cosmetic composition of from 0.5 g to 8.0 g,
   wherein a proportion of the cellulosic fibers in the substrate sheet before impregnation with the liquid cosmetic composition is 30 mass % or more,
   wherein the packaging container comprises the access opening, having an area of 25 $mm^2$ to 4000 $mm^2$, and an openable and closable lid covering the access opening, configured to seal contents of the packaging container,
   and wherein the substrate sheet (A) impregnated with the liquid cosmetic composition (B) is in the packaging container prior to dispensing.

2. The method for treating hair according to claim 1, wherein the substrate sheet has a first side and a second side located opposite to the first side,
   both the first side and the second side have a three-dimensional textured surface having raised portions and recessed portions, and
   in a plan view, the locations of the raised portions on the first side are substantially coincident with those on the second side.

3. The method for treating hair according to claim 2, wherein the substrate sheet has a higher basis weight in the raised portions than in the recessed portions.

4. The method for treating hair according to claim 1, wherein the substrate sheet has a thickness of more than 0.3 mm and not more than 5 mm as measured in accordance with JIS L1096:2010 under a load of 0.3 kPa.

5. The method for treating hair according to claim 1, wherein the substrate sheet has a first side and a second side located opposite to the first side,
   both the first side and the second side have a three-dimensional textured surface having raised portions and recessed portions, and
   the substrate sheet has a perforation at the recessed portion.

6. The method for treating hair according to claim 1, wherein the liquid cosmetic composition (B) comprises: (B-1) a mono- or polyhydric alcohol having 1 to 6 carbon atoms; (B-2) a surfactant; and (B-3) water.

7. The method for treating hair according to claim 1, wherein the liquid cosmetic composition (B) comprises (B-3) water and (B-5) a film-forming resin, the film-forming resin (B-5) being present in the liquid cosmetic composition in an amount of 0.01 mass % to 20 mass %.

8. The method for treating hair according to claim 1, wherein the liquid cosmetic composition (B) comprises (B-1-1) ethanol, (B-3) water, and (B-6) a polysaccharide,
the concentration of ingredient (B-1-1) is 10 mass % to 45 mass % in the liquid cosmetic composition, and
the concentration of ingredient (B-6) is 0.01 mass % to 0.4 mass % in the liquid cosmetic composition.

9. The method for treating hair according to claim 1, wherein the liquid cosmetic composition comprises: (B-2-3) a polyoxyalkylene-added nonionic surfactant; (B-3) water; (B-4-1) an organopolysiloxane represented by following general formula (1); and (B-8) a fragrance, and
the concentration of ingredient (B-2-3) in the liquid cosmetic composition is 0.1 mass % to 2 mass %,

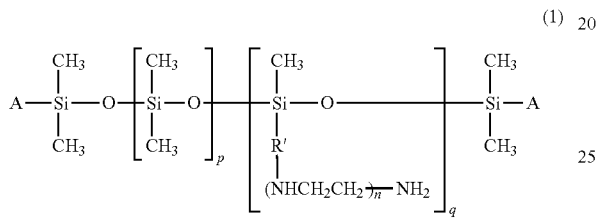

(1)

wherein A represents —R, —R—(NHCH$_2$CH$_2$)$_n$NH$_2$—, —OR, or a hydroxyl group; R represents an optionally substituted monovalent hydrocarbon group having 1 to 20 carbon atoms; R' represents a divalent hydrocarbon group having 1 to 8 carbon atoms; n represents an integer of 0 to 3; p and q each represent a number that satisfies the relationship: 50≤(p+q+2)≤20,000, wherein (p+q+2) is a number-average total number of silicon atoms; and the amino equivalent is 500 g/mol to 100,000 g/mol.

10. The method for treating hair according to claim 1, wherein the liquid cosmetic composition (B) comprises: (B-2-3-1) at least one member selected from polyoxyalkylene monoalkyl ethers and polyoxyalkylene monoalkenyl ethers; (B-2-3-2) at least one member selected from polyoxyalkylene castor oils and polyoxyalkylene hydrogenated castor oils; (B-3) water; (B-4-1) an organopolysiloxane represented by following general formula (1); and (B-7) a cooling agent,

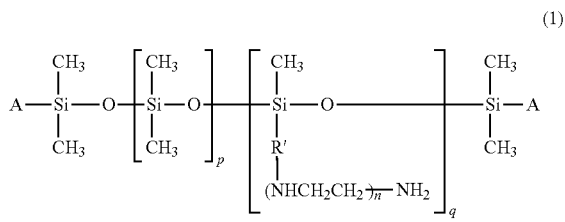

(1)

wherein A represents —R, —R—(NHCH$_2$CH$_2$)$_n$NH$_2$—, —OR, or a hydroxyl group; R represents an optionally substituted monovalent hydrocarbon group having 1 to 20 carbon atoms; R' represents a divalent hydrocarbon group having 1 to 8 carbon atoms; n represents an integer of 0 to 3; p and q each represent a number that satisfies the relationship: 50≤(p+q+2)≤20,000, wherein (p+q+2) is a number-average total number of silicon atoms; and the amino equivalent is 500 to 100,000 g/mol, and the ratio of the sum of the content n$_A$ (mass %) of ingredient (B-4-1) and the content n$_{B7}$ (mass %) of ingredient (B-7) to the sum of the content n$_C$ (mass %) of ingredient (B-2-3-1) and the content n$_D$ (mass %) of ingredient (B-2-3-2), [n$_A$+n$_{B7}$]/[n$_C$+n$_D$], being 0.01 or higher, 0.05 or higher, or 0.1 or higher, and 1 or lower, 0.8 or lower, 0.6 or lower, 0.4 or lower, or 0.3 or lower.

11. The method for treating hair according to claim 1, wherein the liquid cosmetic composition comprises: (B-9) 0.01 to 2 mass % of at least one of a polyhydroxyamine represented by general formula (2) and a salt thereof; (B-10) an anionic thickening polymer; (B-7) a cooling agent; and (B-3) water, and
the liquid cosmetic composition has a pH of 6 to 9.5, and has a solution viscosity of 5 to 5,000 mPa·s at 30° C.,

(2)

wherein R$^1$ represents a hydrogen atom, an alkyl group having 1 to 5 carbon atoms, or a hydroxyalkyl group having 1 to 5 carbon atoms; R$^2$ represents a hydrogen atom, an alkyl group having 1 to 6 carbon atoms, or a hydroxyalkyl group having 1 to 5 carbon atoms; R$^3$ and R$^4$, which may be the same or different, each represent an alkylene group having 1 to 5 carbon atoms.

12. The method for treating hair according to claim 1, wherein
the substrate sheet has a first side and a second side located opposite to the first side,
both the first side and the second side have a three-dimensional textured surface having raised portions and recessed portions,
in a plan view, the locations of the raised portions on the first side are substantially coincident with those on the second side,
the substrate sheet has a higher basis weight in the raised portions than in the recessed portions, and
the substrate sheet has a thickness of more than 0.3 mm and not more than 5 mm as measured in accordance with JIS L1096:2010 under a load of 0.3 kPa.

13. The method for treating hair according to claim 12, wherein the liquid cosmetic composition (B) comprises (B-3) water and (B-5) a film-forming resin, the film-forming resin (B-5) being present in the liquid cosmetic composition in an amount of 0.01 mass % to 20 mass %.

14. The method for treating hair using the sheet-like hair care product according to claim 1, wherein said treating is carried out by moving said user's hand with the sheet-like hair care product thereon from the roots to the tips of hair strands to treat the hair strands.

15. The method for treating hair according to claim 14, wherein said treating is carried out by contacting the roots of hair strands or between the roots of the hair strands and tips of hair strands with fingertips of said user's hand, said fingertips having the sheet-like hair care product thereon, thereby getting bunches of the hair strands in between adjacent fingers, and combing the hair strands with the fingers.

16. The method for treating hair according to claim 1, wherein said contacting comprises treating hair strands with the sheet-like hair care product at least partially on a user's hand.

17. The method for treating hair according to claim 1, wherein said contacting comprises wiping roots of hair strands with the sheet-like hair care product that is at least partially in contact with fingers of a user's hand.

18. The method for treating hair according to claim 1, wherein
   said contacting comprises bunching a plurality of hair strands together to form a group of hair strands; and
   wiping the group of hair strands with the sheet-like hair care product at least partially in contact with fingers of a user's hand.

19. The method for treating hair according to claim 1, wherein
   said contacting comprises bunching a plurality of hair strands to form a group of hair strands and wiping the group of hair strands with the sheet-like hair care product at least partially in contact with fingers of a user's hand; and
   wherein said wiping begins at a central portion of the group of hair strands or at outer tips of the hair of said group of hair strands.

20. The method for treating hair according to claim 1, wherein the access opening is oblong rectangular, oblong elliptic, square, generally square, circular, or generally circular, and is configured for spreading out the sheet-like hair care product and retaining from 6 g to 25 g of a liquid cosmetic composition component (B) in the sheet-like hair care product.

21. The method for treating hair according to claim 1, wherein a viscosity of the liquid cosmetic composition is from 5 mPa·s to 5,000 mPa·s.

22. The method for treating hair according to claim 1, wherein the proportion of the cellulosic fibers in the substrate sheet before impregnation with the liquid cosmetic composition is 40 mass % or more.

23. The method for treating hair according to claim 1, wherein the proportion of the cellulosic fibers in the substrate sheet before impregnation with the liquid cosmetic composition is 30 mass % to 99 mass %.

24. The method for treating hair according to claim 1, wherein the proportion of the cellulosic fibers in the substrate sheet before impregnation with the liquid cosmetic composition is 35 mass % to 97 mass %.

25. The method for treating hair according to claim 1, wherein the proportion of the cellulosic fibers in the substrate sheet before impregnation with the liquid cosmetic composition is 40 mass % to 95 mass %.

* * * * *